Figure 1:
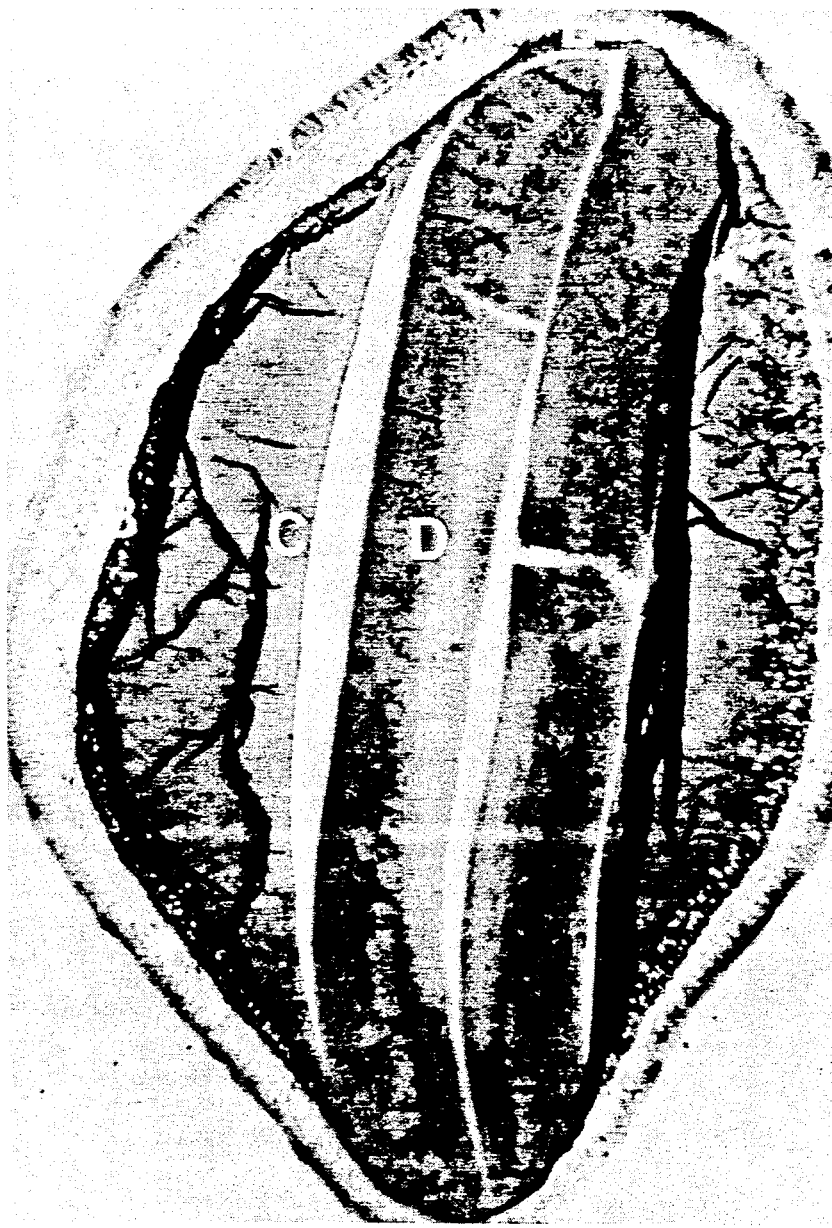

United States Patent [19]

Overbeeke et al.

[11] Patent Number: 5,296,365

[45] Date of Patent: * Mar. 22, 1994

[54] PRODUCTION OF GUAR ALPHA-GALACTOSIDASE BY HOSTS TRANSFORMED WITH RECOMBINANT DNA METHODS

[75] Inventors: Nicholaas Overbeeke, Maasland; Arthur Fellinger, Hoogvliet, both of Netherlands; Stephen G. Hughes, Chelveston, Great Britain

[73] Assignee: Unilever Patent Holdings B.V., Rotterdam, Netherlands

[*] Notice: The portion of the term of this patent subsequent to Jan. 21, 2009 has been disclaimed.

[21] Appl. No.: 721,409

[22] Filed: Jun. 26, 1991

Related U.S. Application Data

[62] Division of Ser. No. 165,995, Feb. 2, 1988, Pat. No. 5,082,772, which is a continuation of PCT/EP87/00296, Jun. 2, 1987.

[30] Foreign Application Priority Data

| Jun. 3, 1986 | [EP] | European Pat. Off. | 86200975 |
| Dec. 18, 1986 | [GB] | United Kingdom | 8630255 |
| Dec. 23, 1986 | [GB] | United Kingdom | 8630719 |
| Apr. 29, 1987 | [GB] | United Kingdom | 8710139 |
| May 11, 1987 | [GB] | United Kingdom | 8711061 |
| May 20, 1987 | [EP] | European Pat. Off. | 87200955 |
| May 26, 1987 | [GB] | United Kingdom | 8712318 |

[51] Int. Cl.$^5$ ............ C12N 9/40; C12N 15/56; C12N 15/80; C12N 15/74
[52] U.S. Cl. ............ 435/208; 435/69.1; 435/69.8; 435/252.31; 435/252.3; 435/240.4; 435/172.3; 435/320.1; 435/254.11; 435/254.2; 435/254.21; 435/254.23; 435/254.3; 536/23.2; 536/23.6; 935/14; 935/23; 935/28; 935/29; 935/37; 935/38; 935/55
[58] Field of Search ............ 435/69.1, 69.8, 208, 435/172.3, 320.1, 240.1, 240.2, 240.4, 252.3, 252.31, 254–256; 935/14, 23, 28, 29, 51, 38, 55; 536/27, 23.2, 23.6

[56] References Cited

U.S. PATENT DOCUMENTS 4,548,904 10/1985 Kent et al. ............ 436/89

FOREIGN PATENT DOCUMENTS 0121960 1/1984 European Pat. Off. .
0120516 10/1984 European Pat. Off. .

OTHER PUBLICATIONS

Wallace et al. "The use of synthetic oligonucleotides as ... " Nuc. Acids Res. 9:879–894 (Feb. 1981).
Maniahs et al. "Molecular Cloning: A Laboratory Manual" Cold Spring Harbor Laboratory, pp. 187–198, 211–246, 390–401 (Jul. 1982).
Bitter et al. "Expression of heterologous genes in ... " Gene 32:263–274 (Dec. 1984).

Primary Examiner—Robert A. Wax
Assistant Examiner—Rebecca Prouty
Attorney, Agent, or Firm—Cushman, Darby & Cushman

[57] ABSTRACT

The gene encoding an alpha-galactosidase from guar seed has been isolated and identified. It has been expressed in yeasts, e.g. Saccharomyces, Kluyveromyces and Hansenula, in bacteria, e.g. Bacillus, and in plants, e.g. Nicotiana. The resulting alpha-galactosidase is able to decrease the galactose content of galactomannans such a guar gum by splitting off 1-6 linked alpha-D-galactopyranosyl units attached to a main chain of 1–4 lined beta-mannopyranosyl units. Thus a commercially feasible process becomes available for producing alpha-galactosidases suitable for providing galactomannans having improved properties, which can meet the increasing demand for good quality polysaccharides. It has further been demonstrated that other alphagalactosidases, which show a positive immunological cross-reaction with an antibody raised against the alpha-galactosidase from guar, are also effective in decreasing the galactose content of galactomannans such as guar.

13 Claims, 35 Drawing Sheets

Fig. 3

A   D - Y - L - K - Y - D - N
MP33: 3'-CTUATUAAVTTVATUCTUTTU

B   NH$_2$-A - E - N - G - L$^5$ - G - Q - T - P - P$^{10}$ - M - G - W - N -
MP42
MP44 3'-C G Y C T Y T T G C C Y G A T C C Y G T T T G Y   3'-G G X T A C C C X A C C T T
                                                          G G G Y T A C C C Y A C C T T
?$^{15}$ - W - N - H - F - G$^{20}$ -?- D - I - N
MP43    3'-ACCTTUGTUAAUCC

Fig. 6(1/4)

```
CTGCAGGGGGGGGGGATCCATCACACACCTTTCTAAGTCTTTTACACTTAGCT
         10        20        30        40        50        60

TATTGTTTCATCAATTGATAACAATAAGTCTTATATACTTATTTGATTTGATACACATA
         70        80        90       100       110       120

-47
                                                   M  A  T  H  Y
CATTATTAATTATTACATTATTCATTCATTCTATATATAAATTAAGATGGCAACGCATTAT
        130       140       150       160       170       180

-42                                              -23
  S  I  I  G  G  M  I  I  V  V  L  L  M  I  N  G  S  E  G  G
TCAATTATAGGTGGGATGATTATAGTGGTGTTGTTGATGATTAATGGAAGTGAAGGTGGT
        190       200       210       220       230       240

-22                                              -3
  R  L  L  E  K  K  N  R  T  S  A  E  A  E  H  Y  N  V  R  R
AGATTATTAGAGAAGAAGAACAGAACAAGTGCAGAGGCAGAGCATTATAATGTTAGGAGA
        250       260       270       280       290       300

-2  1                                            18
  Y  L  A  E  N  G  L  G  Q  T  P  P  M  G  W  N  S  W  N  H
TATCTGGCTGAAAATGGACTAGGCCAGACACCTCCCATGGGTGGAATAGCTGGAATCAC
        310       320       330       340       350       360

20                                               38
  F  G  C  D  I  N  E  N  V  V  R  E  T  A  D  A  M  V  S  T
TTTGGCTGTGATATTAATGAAAACGTAGTTCGAGAAACAGCTGATGCAATGGTTTCAACG
        370       380       390       400       410       420
```

Fig. 6(2/4)

```
        40                                                            58
    L   A   A   L   G   Y   Q   Y   I   N   L   D   D   C   W   A   E   L   N
GGGCTTGCTGCTTAGGCTACCAATATATCAATTAGATGACTGCTGGGCCGAACTTAAT
            430             440             450             460             470             480

60                                                            78
    R   D   S   E   G   N   M   V   P   N   A   A   A   F   P   S   G   I   K   A
CGAGACAGTGAGGGAAATATGGTTCCAAATGCTGCAGCATTCCTTCAGGAATTAAGGCT
            490             500             510             520             530             540

80                                                            98
    L   A   D   Y   V   H   S   K   G   L   K   L   G   V   Y   S   D   A   G   N
CTAGCTGATTATGTTCACAGCAAAGGTTTAAAGTTGGGAGTCTATTCAGATGCTGGAAAT
            550             560             570             580             590             600

100                                                           118
    Q   T   C   S   K   R   M   P   G   S   L   G   H   E   E   Q   D   A   K   T
CAAACATGTAGTAAACGTATGCCTGGATCACTTGGACACGAAGAACAAGATGCAAAAACA
            610             620             630             640             650             660

120                                                           138
    F   A   S   W   G   V   D   Y   L   K   Y   D   N   C   E   N   L   G   I   S
TTTGCCTCATGGGGAGTTGATTATTTGAAGTATGATAACTGTGAGAATTTGGGTATAAGC
            670             680             690             700             710             720

140                                                           158
    V   K   E   R   Y   P   P   M   G   K   A   L   L   S   S   G   R   P   I   F
GTCAAAGAAAGGTACCCACCAATGGGTAAAGCATTATTAAGTTCTGGAAGGCCAATCTTC
            730             740             750             760             770             780

160                                                           178
    F   S   M   C   E   W   G   W   E   D   P   Q   I   W   A   K   S   I   G   N
TTCTCCATGTGTGAATGGGGATGGGAAGACCCACAAATTTGGGCCAAAAGTATAGGAAAT
            790             800             810             820             830             840
```

Fig. 6(3/4)

```
        180
        S  W  R  T  T  G  D  I  E  D  N  W  N  S  M  T  S  I  A  D    198
        AGTTGGAGAACAACTGGAGATATTGAGGACAACTGGAATGGACAACTGGAATGACTTCCATAGCAGAT
           850       860       870       880       890       900

200
        S  N  D  K  W  A  S  Y  A  G  P  G  G  W  N  D  P  D  M  L    218
        TCAAATGATAAATGGGCATCTTATGCTGGACCTGGAGGATGGAATGATCCTGACATGCTT
           910       920       930       940       950       960

220
        E  V  G  N  G  G  M  T  T  E  E  Y  R  S  H  F  S  I  W  A    238
        GAAGTTGGAAATGGAGGGATGACCACAGAAGAATATCGTTCCCATTTCAGCATTTGGGCA
           970       980       990      1000      1010      1020

240
        L  A  K  A  P  L  L  V  G  C  D  I  R  A  M  D  D  T  T  H    258
        TTAGCTAAGGCTCCTCTGCTGGTTGGTTGTGATATTAGAGCAATGGATGACACCACTCAT
          1030      1040      1050      1060      1070      1080

260
        E  L  I  S  N  A  E  V  I  A  V  N  Q  D  K  L  G  V  Q  G    278
        GAACTGATTAGCAATGCTGAAGTTATTGCAGTAAACCAAGATAAACTAGGAGTTCAAGGA
          1090      1100      1110      1120      1130      1140

280
        K  K  V  K  S  T  N  D  L  E  V  W  A  G  P  L  S  D  N  K    298
        AAGAAAGTAAAAAGCACTAATGATTTGGAGGTATGGGCCAGGTCCTCTAAGTGATAACAAG
          1150      1160      1170      1180      1190      1200

300
        V  A  V  I  L  W  N  R  S  S  S  R  A  T  V  T  A  S  W  S    318
        GTGGCAGTGATCTTATGGAATAGAAGTTCTTCAAGAGCAACAGTCACTGCATCCTGGTCT
          1210      1220      1230      1240      1250      1260
```

Fig. 6(4/4)

```
        320
    D   I   G   L   Q   Q   G   T   T   V   D   A   R   D   L   W   E   H   S   T   338
   GACATAGGCCTACAACAAGGAACTACAGTTGATGCAAGAGATTTATGGGAGCACTCAACA
         1270        1280        1290        1300        1310        1320

340
    Q   S   L   V   S   G   E   I   S   A   E   I   D   S   H   A   C   K   M   Y   358
   CAATCATTAGTTTCTGGAGAGAATATCTGCTGAAATAGATTCACATGCTTGCAAGATGTAT
         1330        1340        1350        1360        1370        1380

360                     364
    V   L   T   P   R   S   *   *
   GTTCTGACTCCAAGGAGCTGATGATTTCTGTAGTGGCAGAGAAGTAGATGAACAAGAGAA
         1390        1400        1410        1420        1430        1440

GACAGGATTCAATTTATGGGAACTGCATTGGTTACTACTCATTCTTTCTCTGAGGAAAG
         1450        1460        1470        1480        1490        1500

ATAAATAAACACTGAGAATTTAATTTCAATAAGAATTAACAGAATAAATGTATGTGCTA
         1510        1520        1530        1540        1550        1560

GATTGCCATTGAGCTTCTATTTGTATTTGCGGTTGGCACTTTGAGGCCCATTTGATTTCA
         1570        1580        1590        1600        1610        1620

ATAAATAAATCTTTCAATTAAA   -Poly adenyl
         1630        1640
```

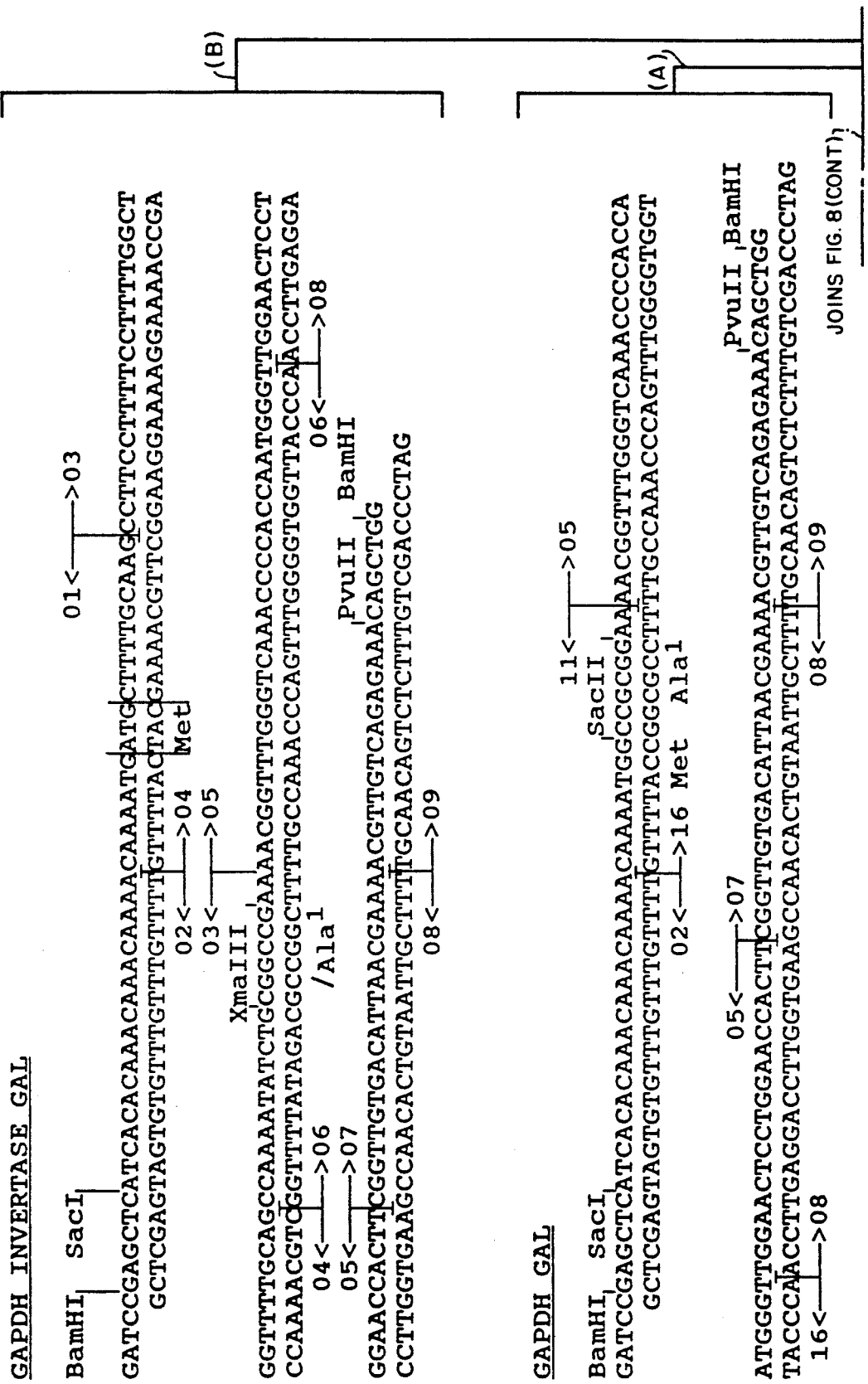

Fig. 16-1(a)

```
BamHI  |  XmnI          |                    1<—T—>3
  GATCCGAAGTTCTTCAAGAGCAACAGTCACTGCATCCTGGTCTGACATAG
       GCTTCAAGAAGTTCTCGTTGTCAGTGACGTAGGACCAGACTGTATC
                       2<—T—>4                              4

3<—T—>5
  GCCTACAACAAGGAACTACA
       CGGATGTTGTTCCTTGATGT
       <—T—>6

5<—T—>7
  GTTGATGCAAGAGATTTATGGAGCACTCAACACAATCATTAGTTTCTGG
       CAACTACGTTCTCTAAATACCCTCGTGAGTTGTGTTAGTAATCAAAGACC
                6<—T—>8                              8<—T—>

7<—T—>9
  AGAAATATCTGCTGAAATAG

TCTTTATAGACGACTTTATC
  10

9<—T—>11                          |----|●
  ATTCACATGCTTGCAAGATGTATGTTCTGACTCCAAGGAGCTGATGAGT
       TAAGTGTACGAACGTTCTACATACAAGACTGAGGTTCCTCGACTACTCA
       10<—T—>12                              12<—T—>13   | S

CGACA

GCTGTTCGA
  alI | HindIII
```

● 
---- translation stop

Fig. 16-2(a)

```
Hgi Al                          0<—T—>1  Met
   |                               |      |  |
     CGGTGGTGACATCAATCTAAAGTACAAAACAAAATGCTGCTCGAG
     ACGTGCCACCACTGTAGTTAGATTTCATGTTTTGTTTTACGACGAGCTC
                                              2<—T—>4

GCCTTCCTGTTCCTCCTG

CGGAAGGACAAGGAGGAC

1<—T—>3              Ala|
                               |
     GCCGGTTTCGCCGCCAAGATCTCCGCCGCCGAGAACGGACTCGGACAGAC
     CGGCCAAAGCGGCGGTTCTAGAGGCGGCGGCTCTTGCCTGAGCCTGTCTG
                              4<—T—>5

| NcoI |
CCCTCCCATGG

GGGAGGGTACCTTAA
         | EcoR1
```

Fig. 18-2(a)

```
EcoRI || BglII |              01<——┬——>02
   AATTCAGAT CTAGCTATAC  TTCGGAGCAC TGTTGAGCGA
                                 ┴
   cttaaGTCTA GATCGATATG  AAGCCTCGTG ACAACTCGCT

AGGCTCATTA GATATATTTT
            ┬
   TCCGAGTAAT CTATATAAAA
   09<——┴——>30

02<——┬——>23
   CTGTCATTTT CCTTAACCCA AAAATAAGGG AGAG
        ┴
   GACAGTAAAA GGAATTGGGT TTTTATTCCC TCTCCTAG
                                    | BamHI
```

Fig. 18-2(b)

```
                                                              GATCCA      AAAAGGCGCTC  GGACAACTGT
                                                                  GT      TTTTCGCGAG   CCTGTTGACA
                                                              BamHI|
TGACCGTGAT  CCGAAGGACT                                24<――――>05
ACTGGCACTA  GGCTTCCTGA  GGCTATACAG  TGTTCACAAA  ATAGCCAAGC  TGAAAATAAT
31<――――>12
05<――――>06
GTGTAGCCTT  TAGCTATGTT  CCGATATGTC  ACAAGTGTTT  TATCGGTTCG  ACTTTTATTA
                                                12<――――>13
                                                06<――――>07
CACATCGGAA  ATCGATACAA  CAGTTAGTTT  GGCTAGCAAA  GATATAAAAG  CAGGTCGGAA
                        GTCAATCAAA
                        13<――――>14
                        07<――――>08
ATATTATGC   GCATTATTAT  GCAGAGCATC  AACATGATAA  CTATATTTC   GTCCAGCCTT
TATAAATACC  CGTAATAATA  CGTCTCGTAG  TTGTACTATT  AAAAAACAGT  TGAATATTCC
14<――――>15                                                  TTTTTGTCA   ACTTATAAGG
|SacI|HindIII                                               15<――――>16
GAGCTCA
CTCGAGTTCG
```

PRODUCTION OF GUAR ALPHA-GALACTOSIDASE BY HOSTS TRANSFORMED WITH RECOMBINANT DNA METHODS

This is a division of application Ser. No. 07/165,995, filed Feb. 2, 1988, now U.S. Pat. No. 5,082,778, which is a continuation of PCT/EP87/00296, filed Jun. 2, 1987.

The present invention relates to a new production method for a specific class of enzymes from the group of alpha-galactosidase enzymes. The latter have the capability of splitting galactose from saccharides containing galactose alpha-linked to other parts of the saccharide. Although alpha-galactosidase enzymes are known from a great variety of organisms (ranging from micro-organisms to human), for only some of them has the structure been elucidated recently, e.g. for *Saccharomyces carlsbergensis* (Liljeström, 1985; Sumner-Smith et al., 1985), a human enzyme (Bishop et al., 1986) and the mel gene from *E. coli* (Liljeström and Liljeström, 1987). The latter two were published after the first claimed priority date of the present specification.

During the investigations resulting in the present invention, it was found that the *S. carlsbergensis* enzyme and the *E. coli* enzyme were not suited for the specific use described below. Human alpha-galactosidase could not be tested owing to lack of availability, but, in view of the experiments described below (cf. Example 4 and the Table in this specification), it is very likely that this human enzyme is also not suited for the specific use.

Thus, only a very limited number of alpha-galactosidase enzyme preparations are suitable for a process for reducing the galactose content of a galactomannan containing 1–6 linked alpha-D-galactopyranosyl units attached to a main chain of 1–4 linked beta-D-mannopyranosyl units (McCleary et al., 1984; EP-A- 0 121 960). In this process the galactomannan is incubated in the form of a hydrated preparation containing 2–70% of galactomannan. In the present specification percentages are given by weight unless specified otherwise. The process yields galactomannans with a reduced content of galactose which can be used with advantage in human and animal foodstuffs and cosmetic preparations. However, the chemical structure of these very specific alpha-galactosidase enzymes is unknown.

In particular the process described in EP-A- 0 121 960 yields galactomannans having a galactose content decreased to a value of preferably between 27% and 10%. The interactive properties of the galactomannan are thereby considerably improved. Galactomannans obtained from guar (*Cyamopsis tetragonoloba*), lucern (*Medicago sativa*) and fenugreek (*Trigonella foenum-graecum*) containing high proportions of galactose are mentioned as examples which can be used as starting materials in the process described in EP-A- 0 121 960. They yield galactomannans which have improved properties and can be used, for example as substitutes for locust bean (carob) gum, which has more favourable properties, such as gelling properties, in particular with other polysaccharides, than untreated guar gum has. Since locust bean gum is becoming more expensive and scarce, due to poor crops and because carob groves are generally not being replanted, the availability of substitutes for locust bean gum is welcomed by the industry in which locust bean gum is applied.

In the process described in EP-A- 0 121 960 an enzyme preparation is used that has a specific alpha-galactosidase activity and has at most a weak beta-mannanase activity. Suitable enzymes can be of vegetable origin (e.g. from lucerne, fenugreek, coffee beans or guar seed) or they can be obtained form bacterial (e.g. *Bacillus cereus, Escherichia coli*) or fungal cultures (e.g. Aspergillus or Saccharomyces), although not all of them are equally effective.

After incubation of the galactomannan with a suitable enzyme preparation until the galatose content of the galactomannan is reduced, the resulting product can be used as such, particularly in combination with other polysaccharides such as agar, carrageenan and xanthan taking advantage of the synergistic interaction with these materials or it can be purified before such use.

In the EP-A- 0 121 960 the following alpha-galactosidases are described in the Examples:

guar seed alpha-galactosidase II (cf. McCleary, 1983): alpha-galactosidase from *Aspergillus niger* (cf. Bahl & Agrawal, 1969);
alpha-galactosidase from the germinating seeds of lucerne (*Medicago sativa*) (cf. Ex. 13); and
alpha-galactosidase from the germinating seeds of fenugreek (*Trigonella foenum-graecum*) (cf. Ex. 13).

Although the treatment with the alpha-galactosidases described in EP-A- 0 121 960 gives improved galactomannans compared with guaran from guar and with other galactomannans with a high galactose content, the availability of the alpha-galactosidase is at present rather limited and its cost is, therefore, rather high.

Moreover, if the preferred guar alpha-galactosidase enzyme is isolated from germinating guar seeds, it must be carefully purified by a laborious procedure, because a substantially complete removal has to be obtained of the undesirable beta-mannanase (which splits the mannan chain of galactomannans; of cf. McCleary, 1983).

Consequently, a need exists for a process for producing alpha-galactosidase preparations capable of decreasing the galactose content of galactomannans without splitting the mannan backbone of the galactomannan by too large an amount.

Further prior art disclosures on decreasing the galactose content of galactomannans by means of alpha-galactosidases are described on pages 2 and 3 of EP-A- 0 121 960 which are incorporated herein by reference.

The present invention provides a process for producing alpha-galactosidase having the ability of splitting off the 1–6 linked alpha-D-galactopyranosyl units from galactomannans having a main chain of 1–4 linked beta-D-mannopyranosyl units to which alpha-D-galactopyranosyl units are attached.

According to the invention, the alpha-galactosidases are prepared by recombinant DNA methods, whereby the gene coding for the protein having the desired alpha-galactosidase properties is cloned in a host organism and the transformed host organism or its progeny is forced to express the gene, thereby producing the polypeptide having the desired alpha-galactosidase properties, optionally after further treatment of the protein produced.

When expression is achieved in micro-organisms, the alpha-galactosidase can be produced by modern fermentation methods without using difficult isolation methods for recovering the alpha-galactosidase, depleted of beta-mannanase, form natural materials.

Production of alpha-galactosidase essentially free of beta-mannanase can be achieved much easier by using micro-organisms than by using plants as they occur in nature, for either cultivation conditions can be chosen such that beta-mannanase production is suppressed completely, or a (mutant) micro-organism can be used which cannot produce beta-mannanase at all.

However, an alternative might be the production of guar alpha-galactosidase or similarly active alpha-galactosidases in plants or plant tissue cultures transformed by recombinant DNA techniques, or their progeny.

Up to now neither the amino acid sequence of a protein having the desired alpha-galactosidase properties, nor the nucleotide sequence of a gene coding for such a protein is known.

We have been able to isolate a gene coding for a protein having the desired alpha-galactosidase properties as will be illustrated below. We have also been able to introduce this gene into cloning vectors, so-called recombinant expression plasmids, which were used successfully to express the gene in the microorganisms *Saccharomyces cerevisiae, Kluyveromyces marxianus* var. *lactis,* formerly known as *Kluyveromyces lactis, Bacillus subtilis* and *Hansenula polymorpha,* as well as in the plant *Nicotiana tabacum* and preparations thereof, the product synthesized being present intracellularly or extracellularly, depending upon the expression plasmid used.

The alpha-galactosidase enzymic activity was in the first instance demonstrated by incubation with p-nitrophenyl-alpha-D-galactopyranoside (pNPG) as described by McCleary (1983) or for plants or tissues with 4-methylumbelliferyl-alpha-D-galactopyranoside as described in Example 11 below. Moreover, the product formed also proved to be active in decreasing the galactose content of guar gum in a way essentially identical with that of the enzyme from the natural guar plant.

Thus one embodiment of the invention relates to a recombinant vector wherein a nucleotide sequence coding for a protein or precursor thereof is inserted and which vector upon transfer to a host organism allows the expression of the nucleotide sequence in the host organism, which protein has alpha-galactosidase activity and is capable of decreasing the galactose content of galactomannans by splitting off 1-6 linked alpha-D-galactopyranosyl units attached to a main chain of 1-4 linked beta-D-mannopyranosyl units. Such precursor comprises the protein provided with one or more oligopeptides or polypeptides which facilitate, for example, the translocation of the protein.

It was found that several alpha-galactosidases showing a positive immunological cross-reaction with an antibody raised against the alpha-galactosidase from guar seed, are also capable of decreasing the galactose content of galactomannans by splitting off 1-6 linked alpha-D-galactopyranosyl units attached to a main chain of 1-4 linked beta-D-mannopyranosyl units, whereas other alpha-galactosidases giving a negative immunological cross-reaction with an antibody raised against the alpha-galactosidase from guar seed, did not having the desired capability.

It was further found that a nucleotide sequence encoding an alpha-galatosidase could be modified by genetically engineering without the resulting alpha-galactosidase losing the desired capability.

Thus the nucleotide sequence can be selected from the group consisting of:

(a) naturally occurring nucleotide sequences encoding an alpha-galactosidase having the specific capability given above:

(b) nucleotide sequences encoding an alpha-galactosidase which shows a positive immunological cross-reaction with the antibody raised against the alpha-galactosidase from guar seed; and (c) genetically engineered nucleotide sequences encoding an alpha-galactosidase being either the same as that of (a) or (b) or a modification thereof still having the specific capability given above.

For example, a gene can be made having a codon use that is better adapted to the micro-organism by which the alpha-galactosidase should be produced. In that case a so-called alpha-galactosidase gene, which is the nucleotide sequence encoding an alpha-galactosidase, codes for an alpha-galactosidase which is the same as a naturally occurring alpha-galactosidase, because both enzymes have the same amino acid composition. But it is also possible to make a gene encoding a modification thereof, which modified enzyme still has the specific alpha-galactosidase activity. By applying recombinant DNA techniques it is possible to prepare genetically engineered genes that encode modifications of alpha-galactosidase having improved properties, for example improved thermostability and/or specific activity, etc.

The invention especially provides a vector in which the nucleotide sequence encodes a protein comprising the following amino acid sequence:

```
1                                                  50
AENGLGQTPPMGWNSWNHFGCDINENVVRETADAMVSTGLAALGYQYINL 51                                                 100
DDCWAELNRDSEGNMVPNAAAFPSGIKALADYVHSKGLKLGVYSDAGNQT 101                                                150
CSKRMPGSLGHEEQDAKTFASWGVDYLKYDNCENLGISVKERYPPMGKAL 151                                                200
LSSGRPIFFSMCEWGWEDPQIWAKSIGNSWRTTGDIEDNWNSMTSIADSN 201                                                250
DKWASYAGPGGWNDPDMLEVGNGGMTTEEYRSHFSIWALAKAPLLVGCDI 251                                                300
RAMDDTTHELISNAEVIAVNQDKLGVQGKKVKSTNDLEVWAGPLSDNKVA 301                                                350
VILWNRSSSRATVTASWSDIGLQQGTTVDARDLWEHSTQSLVSGEISAEI 351            364
DSHACKMYVLTPRS
```

If one wants to use the natural gene encoding guar seed alpha-galactosidase, one should preferably use a double-stranded complementary DNA (ds-cDNA) as found by the procedures given in this specification, the plus strand of this ds-cDNA having the nucleotide sequence 307-1398 given in FIG. 6, whereby the amino acid sequence 1-364 is indicated above the corresponding codons.

A vector suitable for a selected host organism preferably comprises:

(a) a double-stranded DNA (ds-DNA) coding for alphagalactosidase or a precursor thereof;

(b) a translational stop condon, bound to the the lb 3'-end of the coding region of the plus strand of the ds-DNA of (a), optionally followed by a transcription termination sequence suitable for the selected host organism;

(c) an expression regulon suitable for the selected host organism situated upstream of the plus strand of the ds-DNA of (a);

(d) a translational initiation ATG-triplet bound to the 5'-end of the coding region of the plus strand of the ds-DNA of (a), when the ds-DNA codes for a matured form of the alpha-galactosidase and when that form does not start with a methionine residue;

(e) nucleotide sequences which facilitate integration of the ds-DNA of (a) into the genome of the selected host organism and/or an origin of replication suitable for the selected host organism and optionally a selection marker; and (f) optionally a ds-DNA encoding a precursor part of a precursor form of alpha-galactosidase.

Another embodiment of the present invention relates to a transformed host organism having the capability of producing alpha-galactosidase, preferably essentially free of beta-mannanase, as a consequence of the introduction of a recombinant vector as hereinbefore defined, and its progeny. The hose organism can be a plant or part thereof, such as Solanacea, in particular Nicotiana, or animal or human cells, but also a microorganism such as bacteria, e.g. Bacillus, moulds, e.g. Aspergillus, and yeast, e.g. Saccharomyces, Kluyveromyces, Hansenula and Pichia. The invention has been carried out with the following host organisms: *Saccharomyces cerevisiae, Klyveromyces marxianus* var. *lactis, Bacillus subtilis, Hansenula polymorpha* and *Nicotiana tabacum*. Since the gene has been expressed in so many and different host organisms, it is realistic to expect that it can also be expressed in various other host organisms. Some examples are *Pichia pastoris, Saccharomyces carlsbergenis, Aspergillus niger* and *Aspergillus nidulans*.

The main embodiment of the present invention, however, relates to a process for producing alpha-galactosidase capable of decreasing the galactose content of galactomannans by splitting off 1-6 linked alpha-D-galactopyranosyl units attached to a main chain of 1-4 linked beta-D-mannopyranosyl units, characterized in that a transformed host organism as hereinbefore defined is cultured under such conditions that the alpha-galactosidase is produced either during culturing or upon induction after culturing, whereafter the alpha-galactosidase is collected. According to this embodiment, it is preferred that the alpha-galactosidase is secreted by the host organism, whereafter the collection of the alpha-galactosidase is achieved by removing the cells from the fermentation broth, optionally followed by concentration of the resulting broth.

The present invention also provides a process for decreasing the galactose content of galactomannans by incubating an aqueous preparation of galactomannan with an alpha-galactosidase essentially free of beta-mannanase. Such a process is known from e.g. EP-A-0 121 960. The process according to the present invention is, however, characterized in that an alpha-galactosidase is used, produced by a process as described in the previous paragraph. The present invention provides an alpha-galactosidase at such costs and in such quantities that the known process for modifying galactomannans becomes commercially more attractive.

Finally the present invention relates to a process for preparing foodstuffs, animal feedstuffs or cosmetics in which a galactomannan with reduced galactose content prepared by a process as described in the previous paragraph is used, optionally in admixture with one or more other thickening or gelling agents, examples of which are gum arabic, tragacanth, agar, algin, carrageenan, furcellaran, pectin, gelatin, starch and modified gums, e.g. carboxymethylcellulose.

The latter two embodiments can also be described as:

(1) the use of an alpha-galactosidase for decreasing the galactose content of galactomannans, which alpha-galactosidase is produced by a process according to the invention, in which process a transformed host organism is used capable of forming the alpha-galactosidase, and (2) the use of a galactomannan with reduced galactose content in the preparation of foodstuffs, animal feedstuffs or cosmetics, which galactose-reduced galactomannan is obtained by treatment of a galactomannan having a higher galactose content with an alpha-galactosidase produced by a process according to the invention.

SUMMARY OF THE INVENTION AND OUTLINE OF THE TECHNICAL DESCRIPTION

The various aspects of the present invention are the result of intensive investigations. These are outlined below and described in great detail in the Examples.

One aspect of the present invention relates to the elucidation of the nucleotide sequence and the amino-acid sequence of an alpha-galactosidase enzyme capable of substantially decreasing the galactose content of galactomannans by splitting off 1-6 linked alpha-D-galactopyranosyl units attached to a main chain of e.g. 1-4 linked beta-D-mannopyranosyl units (see Example 1).

It was known that this enzymic activity was present in the endosperm of germinating guar seeds. It was, however, unknown which cells in the guar seed are responsible for the production of this alpha-galactosidase enzyme.

Microscopical studies on the germination of guar seeds combined with observations of endosperm degradation after removal of seed coat and/or embryo led us to the hypothesis that the enzyme is produced within the endosperm itself, the aleurone cells being the most likely candidates (section 1.1 of Example 1).

This hypothesis had to be verified. mRNA had, therefore, to be purified from the aleurone cells. It was found that the endosperms, dissected from seeds germinated for 20 hours, could not be used as such for purification of RNA. The polysaccharides prevented extraction of RNA even with highly chaotropic agents due to gel formation. To solve this problem we used externally added enzymes to degrade the endosperm polysaccharides. It appeared that the conditions had to be carefully adjusted, otherwise RNA in the aleurone cells was degraded during the procedure, most likely as the result of an RNase enzyme produced by the aleurone cells themselves. The purified RNA was analysed for presence of a mRNA encoding alpha-galactosidase by:
in vitro-translation and analysis for proteins which react with alpha-galactosidase specific antibodies.
hybridization of a mRNA with oligonucleotide mixed probes which are specific for alpha-galactosidase. To construct these specific probes we determined small parts of the amino acid sequence of purified protein.

The results of both analyses showed that the mRNA encoding alpha-galactosidase was present in the aleurone cells (section 1.2 of Example 1).

The mRNA was used for cloning the guar alpha-galactosidase cDNA clone by standard techniques using the alpha-galactosidase specific oligonucleotide mixed probes (sections 1.3 and 1.4 of Example 1).

The nucleotide sequence of the guar alpha-galactosidase cDNA clone was determined and the amino acid sequence derived. The $NH_2$-terminal amino acid sequence determined for purified protein appeared to be identical with the amino acid sequence derived from the nucleotide sequence and showed furthermore that the alpha-galactosidase is synthesized in a precursor form with a 47 amino acid residues extension preceding the mature protein (section 1.5 of Example 1).

Another aspect of the invention relates to the potentials for a new production route of guar alpha-galactosidase by various hosts. We provide a new production process for alpha-galactosidase enzymes with the specific ability as disclosed above. For two microbial host organisms the experiments show that an economically interesting level is already approached, for several other host organisms (both micro-organisms and plants) the feasibility is also demonstrated.

For illustration we constructed plasmids capable of producing the enzyme in Saccharomyces, Kluyveromyces, Bacillus, Hansenula and Nicotiana.

As an illustration for *S. cerevisiae*, for one plasmid, pURY2703, a yeast GAPDH promoter was fused to the genetic information encoding only the mature alpha-galactosidase. For another plasmid, pURY2705, the GAPDH promoter was fused to a hybrid gene consisting of invertase signal sequence::mature alpha-galactosidase. Both plasmids gave rise to production of enzymes in *S. cerevisiae* which were active on para-nitrophenyl-alpha-D-galactopyranoside. However, the product of pURY2705 could be demonstrated outside the yeast cells in contrast to the product of pURY2703. Furthermore, Western blot analysis showed that the product from pURY2705 had the same molecular weight as the plant enzyme, while the product of pURY2703 had a slightly lower molecular weight (see Example 2).

From yeast cells harbouring plasmid pURY2705 a crude extract was prepared such that 10 units alpha-galactosidase were present in 1 ml. Such a crude preparation was capable of decreasing the galactose content of guar gum (see Example 3).

As another illustration for Saccharomyces, we constructed plasmids pUR2706 and pUR2730, fusing the GAL7 promoter, which is inducible by growth of yeast cells on galactose as the carbon source, to a hybrid gene consisting of invertase signal sequence::mature alpha-galactosidase.

The difference between the plasmids is that for pUR2706 a cloned GAL7 DNA fragment of 271 bp was used, while for pUR2730 the GAL7 promoter was obtained from in vitro synthesized oligonucleotides. Plasmid pUR2706 gave rise to production by yeast cells of the enzyme upon induction by growth on galactose. The enzyme is secreted into the growth medium up to levels of 5000 U/liter, correctly processed and glycosylated (cf. Example 9).

From the fermentation broth, yeast cells were removed by filtration and the broth concentrated ten-fold. Such a crude concentrate was capable of decreasing the galactose content of guar gum in a way exactly identical compared with the enzyme purified from guar seeds (cf. Example 10).

The finding that a relation exists between a positive immunological cross-reaction with an antibody raised against the alpha-galactosidase from guar seed and the ability to decrease the galactose content of a galactomannan, is demonstrated in Example 4.

To illustrate that the alpha-galactosidase gene can be expressed not only in *S. cerevisiae*, but also in other micro-organisms, plasmids were constructed capable of producing the enzyme in various micro-organisms, namely in:
(a) *Kluyveromyces marxianus* var. *lactis*,
(b) *Hansenula polymorpha* and
(c) *Bacillus subtilis*.

(a) Producing the alpha-galactosidase in *Kluyveromyces marxianus* var *lactis*.

A plasmid called pUR2405 was prepared by introducing into the *S. cerevisiae* plasmid pURY2705 both a Kluyveromyces Autonomic Replicating System (namely KARS2) and a selection marker (the trp-1gene). Yeast cells of strain *K. marxianus* var. *lactis* strain SD11 (lac-4, trp-1) were transformed with plasmid pUR2405. After growth the cell extracts of the transformed strain contained a protein capable of hydrolysing the artificial substrate pNPG, in contrast with the same strain without the plasmid. Moreover, a Western blot analysis of the crude cell extracts showed a specific reaction with the guar alpha-galactosidase antiserum demonstrating the presence of guar alpha-galactosidase enzyme (see Example 5). These experiments demonstrate that the transformed Kluyveromyces produces the guar alpha-galactosidase enzyme.

(b) Producing alpha-galactosidase in *Hansenula polymorpha*

The potentials for *H. polymorpha* to produce heterologous products using specifically an inducible promoter like e.g. the MOX promoter or the DHAS promoter have already been recognised. A plasmid called pUR3510 was constructed based on the vector YEp13 which is capable of replicating in *H. polymorpha* and of complementing a leu⁻ mutation. In this vector was engineered the following construction: MOX promoter—invertase signal sequence—mature alpha-galactosidase—MOX terminator. Yeast cells of strain *H. polymorpha* L1(leu 1-1) were transformed with plasmid pUR3510. After growth on MM agar plates with glycerol as the carbon source, cells were scraped off and cell extracts prepared. The cell extracts of the transformed strain contained a protein capable of hydrolysing the artificial substrate pNPG, in contrast with the same strain without the plasmid. Moreover, a Western blot analysis of the crude cell extracts showed a specific reaction with the guar alpha-galactosidase antiserum demonstrating the presence of guar alpha-galactosidase enzyme (see Example 8). These experiments demonstrate that the transformed Hansenula produces the guar alpha-galactosidase enzyme.

(a)

To illustrate that the alpha-galactosidase gene can be expressed not only in eukaryotic micro-organisms, but also in prokaryotic micro-organisms, plasmids were constructed capable producing the enzyme in *Bacillus subtilis*

A plasmid called pUR2601 was prepared in which the SPO2 promoter was placed before the hybrid gene consisting of alpha-amylase signal sequence::mature alpha-galactosidase (Example 6).

When *B. subtilis* cells harbouring this plasmid were cultured, a protein was present in a specific growth phase in the culture medium having activity on pNPG. By choosing an optimal growth medium and growth conditions in a fermenter, an amount of 1760 U/liter was found in the growth medium. A Western blot analysis showed a specific reaction with the guar alpha-galactosidase antiserum demonstrating the presence of the guar alpha-galactosidase enzyme in the growth medium. However, the molecular weight was slightly lower than the molecular weight of the plant enzyme. Since by sequencing of the NH$_2$ terminus we found that the alpha-amylase signal sequence was completely and correctly removed, this difference is caused by the fact that the Bacillus enzyme is not glycosylated.

These experiments demonstrate that the transformed Bacillus not only produces the guar alpha-galactosidase but also excretes it into the growth medium. It was further found that the enzyme produced by Bacillus was capable of decreasing the galactose content of guar gum (Example 7).

To illustrate that the alpha-galactosidase gene can be expressed not only in micro-orgamisms, but also in plants, plasmids were constructed capable of producing the enzyme in *Nicotiana tabacum*, namely in callus cultures, root cultures, suspension cultures and in whole plants. Therefore, a plant expression vector containing the complete guar pre-pro-alpha-galactosidase gene was constructed (pUR8001). This vector was inserted in Nicotiana plants or preparations thereof via an *Agrobacterium tumefaciens*-derived vector. The results showed that an active alpha-galactosidase enzyme was produced in callus cultures, hairy root cultures, leaves and suspension tissue cultures. Furthermore, Western blot analysis showed that the alpha-galactosidase enzyme produced in tobacco tissues had the same molecular weight as the enzyme produced in the guar aleurone cells (cf. Example 11).

The different embodiments of the invention are illustrated in the following Examples without being limited thereto. The Examples relate to the following subjects whereby Examples 1 and 4 are subdivided.

EXAMPLE 1

Isolation and characterization of the genetic information encoding an alpha-glactosidase enzyme capable of decreasing the galactose content of galactomannans.
1.1. Identification of cells in guar seeds producing alpha-galactosidase.
1.2. Purification and analysis of mRNA from aleurone cells.
1.3. Construction of a cDNA library from mRNA of aleurone cells from guar seed.
1.4. Selection of clones containing the guar alpha-galactosidase genetic information.
1.5. Determination of the nucleotide sequence of the guar alpha-galactosidase cDNA close and the derived amino acid sequence of the alpha-galactosidase enzyme.

EXAMPLE 2

Production of the guar alpha-galactosidase by genetically engineered *Saccharomyces cerevisiae*.

EXAMPLE 3

Reduction of the galactose content of galactomannans by the alpha-galactosidase enzyme produced by genetically engineered *S. cerevisiae*.

EXAMPLE 4

Immunological relationship and gum modification capacity for various alpha-galactosidase enzymes.
4.1. Source of alpha-galactosidase enzymes.
4.2. Enzymes produced by genetically engineered microorganisms: *Saccharomyces cerevisiae, Kluyveromyces marxianus* var. *lactis, Hansenula polymorpha* and *Bacillus subtilis*.
4.3. Immunological relationship analysed by Ouchterlony double diffusion.
4.4. Immunological relationship analysed by Western blot technique.
4.5. Capability of alpha-galactosidase enzymes to decrease the galactose content of galactomannans.

EXAMPLE 5

Production of the guar alpha-galactosidase by genetically engineered *Kluyveromyces marxianus* var. *lactis*.

EXAMPLE 6

Production of the guar alpha-galactosidase by genetically engineered *Bacillus subtilis*.

EXAMPLE 7

Reduction of the galactose content of galactomannans by the alpha-galactosidase enzyme produced by genetically engineered *B. subtilis*.

EXAMPLE 8

Production of the guar alpha-galactosidase by genetically engineered *Hansenula polymorpha*.

EXAMPLE 9

Production of the guar alpha-galactosidase by genetically engineered *Saccharomyces cerevisiae* using the GAL7 promoter.

EXAMPLE 10

Reduction of the galactose content of galactomannans by the alpha-galactosidase enzyme produced by genetically engineered *S. cerevisiae* using the GAL7 promoter.

EXAMPLE 11

Production of the guar alpha-galactosidase by genetically engineered plants and plant tissues, in particular Nicotiana species.

The specification also comprises a Table, a list of References, a list of abbreviations used, legends to the Figures and FIGS. 1-21.

EXAMPLE 1

Isolation and Characterization of the Genetic Information Encoding an Alpha-galactosidase Enzyme Capable of Decreasing the Galactose Content of Galactomannans

1.1. Identification of Cells in Guar Seeds Producing Alpha-galactosidase

As it was shown (McCleary et al., 1984; EP-A-0 121 960) that the preferred enzyme for the modification of guar gum was the alpha-galactosidase enzyme purified from the endosperm of seeds of guar, we focussed on the elucidation of this specific enzyme.

Guar is an endospermous legume. The seed endosperm consists of a cell layer, aleurone, and reserve material, composed chiefly of galactomannan which is laid down initially as a cell wall polysaccharide and degraded during seed germination. As in other legumes, storage proteins are confined to the seed cotyledons, which are encased within the endosperm. Studies on the germination of endospermous legumes and on the mobilization of reserves have been carried out for the related legumes fenugreek and lucerne (for a review, see Meier and Reid, 1982). It was shown that, following imbibition (achieved by water-soaking), enzymes are leased into the en osperm, the two major enzymic activities being alpha-galactosidase and beta-mannanase. These results suggest that the enzymes are synthesized in the aleurone cells upon germination of the fenugreek seeds, although, to our knowledge, conclusive evidence has not been obtained up till now.

Because of the relatedness of guar and fenugreek, we hypothesized that also in guar seeds these enzymes are most likely synthesized in the aleurone cells.

At first we studied the germination of guar seed by microscopical methods.

Seeds were sliced with a sharp razor blade into 1 mm discs before fixing in 2.5% glutaraldehyde in 0.1M sodium cacodylate buffer (pH 7.4) for 6 hours at 3° C. The material was then rinsed through several changes of the same buffer and post-fixed for 4 hours in 1% osmium tetroxide in 0.1M cacodylate buffer (pH 7.4) at room temperature. Tissues were dehydrated through ethanol and embedded in Spurrs Epoxy resin. Polymerisation was carried out at 70° C. for 24 hours. Sectioning was performed using glass knives on a Reichert Ultracut microtome. Sections were cut at 1 and 2 micrometers thickness and floated on a drop of distilled water in a cleaned glass slide and placed on a hotplate at 60° C. to dry. Staining was carried out using 1% Toluidine Blue O and the sections were mounted in DPX mountant (from BDH). Photomicrographs were taken on a Leitz Ortholux microscope using both Phase and Interference Contrast optics. Polarised light was used to highlight the strong birefringence of heavily thickened seed coat.

In the section of ungerminated guar seed shown in FIG. 1 it can be seen that in guar the aleurone does not form a single coherent layer of cells as in some endospermous seeds. The layer is 2, 3, 4 or more cells shown at different points. As germination proceeded, the endosperm became progressively softer and difficult to section. When seeds were germinated 42 hours, there was a clear breakdown of the structure of the endosperm, but the outer layer of aleurone cells appeared to remain intact within a stable intercellular matrix, although the cells appeared to be depleted of contents. At this stage there was a clear break between the aleurone layer and the residual endosperm, suggesting that endosperm degradation is most intense close to the aleurone. This might indicate that the enzymes of endosperm digestion are released from the aleurone layer. The progress of endosperm degradation was not altered by the absence of seed coat during germination. Also, if the embryo was removed after imbibition, a similar softening of the endosperm was observed. This suggested that neither the seed coat nor the embryo is involved in the degradation of the endosperm. This means that they most likely are also not involved in production of the enzymes responsible for degradation of the endosperm, alpha-galactosidase and beta-mannanase.

These results are in agreement with the hypothesis that also in guar seeds the alpha-galactosidase, or its precursor, is produced in the aleurone cells and subsequently secreted by these cells into the reserve polysaccharide layer. However, conclusive evidence for this hypothesis can only be obtained by demonstration that either the alpha-galactosidase enzyme or the mRNA encoding alpha-galactosidase is present in the aleurone cells. Because problems can be envisaged for the demonstration of the presence of the protein (rapid secretion, precursor form not identifiable) we had to analyse the presence of mRNA encoding alpha-galactosidase in the aleurone cells.

1.2. Purification and Analysis of mRNA From Aleurone Cells

To analyse the mRNA content of aleurone cells for the presence of the alpha-galactosidase-encoding mRNA, we adopted the following strategy:

isolation of aleurone cells free from the majority of polysaccharides present in the endosperm:

purification of mRNA from the aleurone cells;

in vitro translation of mRNA, isolation of the protein products with antibodies raised against purified alpha-galactosidase, and analysis by polyacrylamide gel electrophoresis;

Northern blot hybridization of the mRNA with an alpha-galactosidase specific oligonucleotide probe based on a partly established amino acid sequence.

1.2.1. Isolation of Aleurone Cells

Guar seeds (commercial variety King Guar var. seah 90; fungicide treated, purchased from Crown Quality Seed Co., Texas) were sterilised for 1 hour is 10% Chloros (bleach; 4% available chlorine). Subsequently, the seeds were washed in sterilised tap water, to imbibe, for 5 hours, with frequent changes of water (the water becomes brown as a consequence of leaching of pigments from the seed coat) and allowed to germinate on the surface of a gel of tap water/1% agarose contained within transparent margarine tubs. Germination was allowed to proceed for 20 hours.

Seeds were then individually dissected. First the seed coat was peeled off, having been first pierced in the region of the micropile. The endosperm was then separated from the embryo by gently tearing the thin part of the endosperm which spans the edges of the two cotyledons. The endosperm was then separated into its two halves.

Attempts to purify RNA directly from these germinating endosperms failed because they resulted in a totally intractable gel even when the most powerful chaotropic agents were employed (e.g. guanidinium thiocyanate).

Therefore, a further separation of the aleurone cells from the polysaccharide mass was necessary.

We decided to try to degrade the polysaccharides by externally added enzyme preparations.

Endosperms, separated into two halves, were floated in enzyme solution dissolved in Gamborg B5 medium (Gibco), supplemented with 12% sucrose. Incubation was at 22° C.

Complete digestion of the endosperm contents could be monitored visually and was dependent on both the enzyme used and its concentration. As digestion proceeded, the endosperms progressively lost their hemispherical shape and became soft and flexible. A number of commercially available enzymes were tested at different concentrations, Onazuka R10 (Kinki Honsha Co. Ltd), Gammanase (NOVO) and Driselase (Fluka). Since initial studies had shown that exposure to concentrated commercial enzyme preparations resulted in aleurone cell plasmolysis and death, we cleaned up the enzyme preparation so that it could be used in a highly concentrated form. This was done by dialysis using benzoylated dialysis tubing (Sigma). The enzyme was dissolved (10%) in B5 medium containing 12% sucrose and then dialysed for 18-24 hours before use, against the same medium at 4° C. The enzyme was then used to digest endosperms. Of these, Driselase appeared to be the most effective at a 10% concentration. After 7-8 hours of incubation, the endosperms rolled up, all the supporting polysaccharide tissue having been digested away. Aleurone "rolling" was taken as the end point for digestion. Samples of "rolled up" aleurones were examined microscopically (for necrosis) and also were checked for viability using FDA staining. (Fluorescein diacetate stain, Hoechst, was made at 5 mg/ml in acetone and diluted 1/50 in medium immediately before use.) Optimised enzyme treatments (10% enzyme, 7-8 hours incubation) resulted in few (less than 20%) nonviable or necrotic cells. RNA preparations from these cells showed that the RNA was well conserved as judged by the integrity of the ribosomal RNA.

Aleurone layers of the required appearances (white and rolled up) were individually lifted out from the digestion medium and washed in the same osmoticum five times to remove residual polysaccharides. They were finally dropped into liquid nitrogen for storage. Sections of this material prepared for microscopy showed that the aleurones were 2-3 cells thick and that the cells were embedded in a matrix which had resisted digestion by the enzyme preparation.

1.2.2. Purification of RNA From Aleurone Cells

The frozen aleurone material was ground in a mortar and pestle maintained at the temperature of dry ice. The ground material was allowed to thaw in 1 volume of lysis buffer (50 mM Tris-HCl pH 8.0, 2% Sarkosyl) plus 2 volumes of phenol (equilibrated with 1M Tris-HCl pH 8.0). After mixing and centrifugation (10 minutes, 5000 rpm), this phenol extraction was repeated twice on the water phases. Finally, nucleic acids were precipitated overnight at −20° C. after addition of 1/10 volume 3M sodium acetate (NaAc) pH 5.4 and 2.5 volumes of ethanol.

For qualitative analysis, RNA was precipitated, dissolved in STE buffer (100 mM NaCl, 10 mM Tris-HCl pH 7.5, 1 mM EDTA), boiled for 1 minute and immediately chilled on ice. An equal volume of sample buffer [10M urea, 10% sucrose, 0.02% bromophenol blue in E buffer (40 mM Tris-HAc pH 7.6, 20 mM NaAc, 20 mM EDTA)] was added. Samples (3-10 /μg) were electrophorized on an agarose-urea gel (1.8% agarose, 5M urea in E buffer). RNA bands were visualized by staining in ethidium bromide (0.5 μg/ml) for 15 minutes and exposure to long wave UV light.

For further purification, RNA dissolved in STE buffer was preferentially precipitated by addition of 1 volume 8M LiCl and incubation overnight on ice. The precipitate was collected by centrigugation for 10 minutes at 10,000 rpm. (This step removes DNA and most of the polysaccharides still present in the preparations.) The RNA pellet was dissolved in STE buffer with 0.1% Sarkosyl, the concentration was determined by measuring the absorbance at 260 nm and store din aliquots a −20° C. after addition of 1/10 volume 3M Na Ac pH 5.4 and 2.5 volumes of ethanol.

For the purification of polyadenylated mRNA (poly-A RNA), 2.5 mg RNA was precipitated in an Eppendorf tube, dissolved in 300 μl $H_2O$, heated for 5 minutes at 65° C. and chilled on ice-water, whereafter added 300 μl of a mixture containing 10 mM Tris-HCl pH 7.5, 1M NaCl and 0.1% Sarkosyl was added.

The RNA was added to 50 mg oligo-dT cellulose (type T2, Collaborative Research) which had been washed 3 times with O buffer (10 mM Tris-HCl pH 7.5, 1 mM EDTA, 0.5 NaCl, 0.1% Sarkosyl). After incubation for at least 4 hours at room temperature while rotating end over end, the mixture was layered on a blue Eppendorf 1 ml pipetitting tip containing a plug of siliconized glass-wool. The RNA concentration in the effluent was measured and the column was washed with O buffer until the extinction at $OD_{260}$ was less than 0.05.

The poly-A RNA bound to the column was finally eluted by addition of $6 \times 100$ μl of a mixture containing 10 mM Tris-HCl pH 7.5, 1 mM EDTA and 0.1% Sarkosyl. The amount of poly-A RNA, usually 1% of total RNA, was determined by measuring the extinction at 260 nm.

1.2.3. In vitro Translation of Poly-A-RNA

The Wheat Germ Translation system was obtained from New England Nuclear and the procdure performed according to their instructions with $^{35}S$-methionine (1066 Ci/mmol) as the radioactive precursor. The translation products were analysed by autoradiography after separation on a polyacrylamide gel as described by Edens et al. (1982).

Translation products were applied directly or after incubation with alpha-galactosidase specific antiserum, raised by immunization of rabbits with alpha-galactosidase protein purified as described by McCleary (1983). Proteins that had reacted with the antiserum were separated by precipitation with Protein A-Sepharose (Pharmacia) as described by Edens at al. (1982).

It was demonstrated (FIG. 2) that, among the variety of proteins encoded by the mRNA purified from the aleurone cells, one is present which reacts with the alpha-galactosidase specific antibodies. The apparent molecular weight of the protein is 44 kd.

1.2.4. Northern Blot Hybridization With An Alpha-Galactosidase Specific Oligonucleotide Probe

1.2.4.1. Oligonucleotide Probes

Figures 1B, 16:
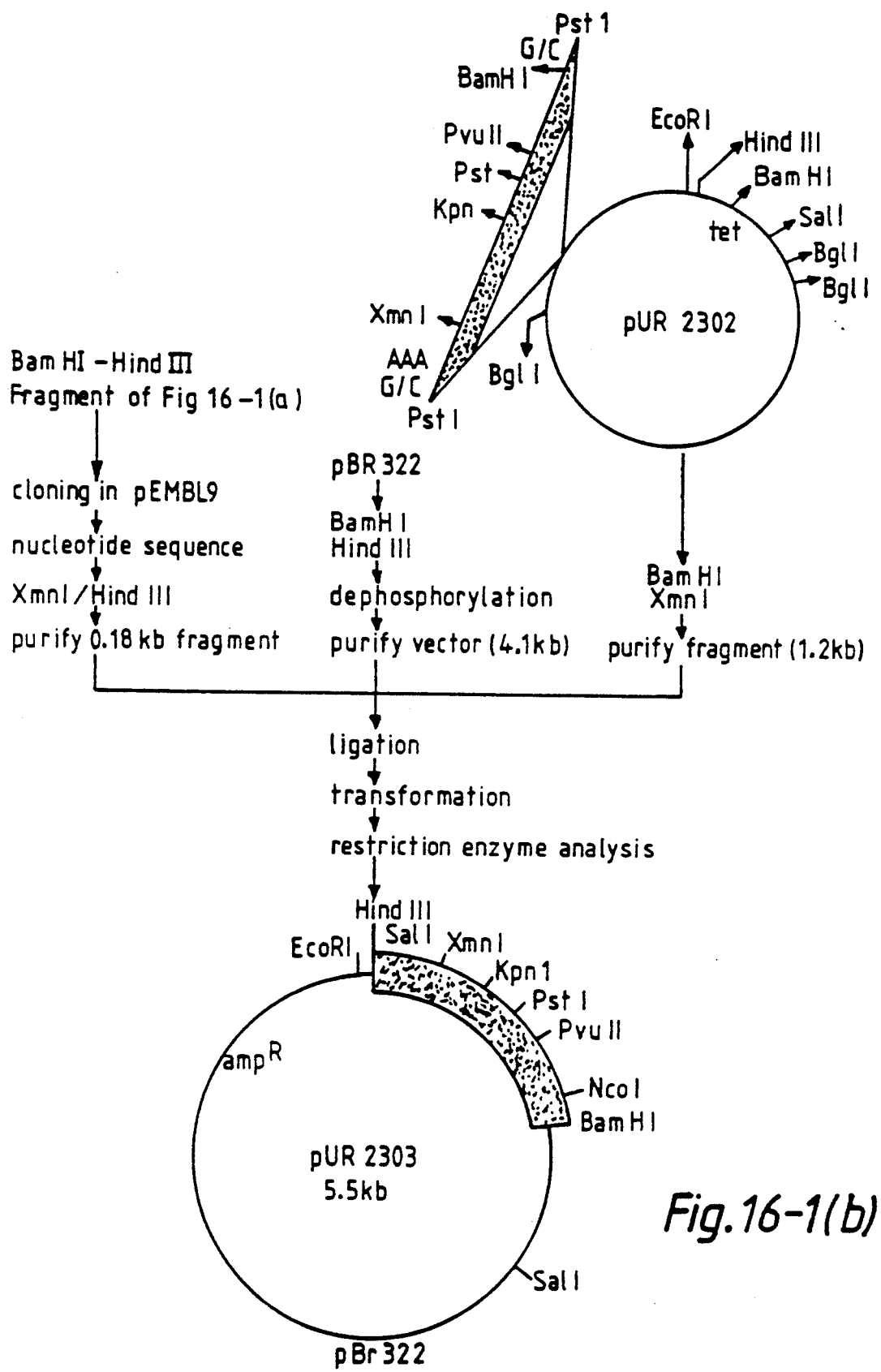
Figures 2B, 16:
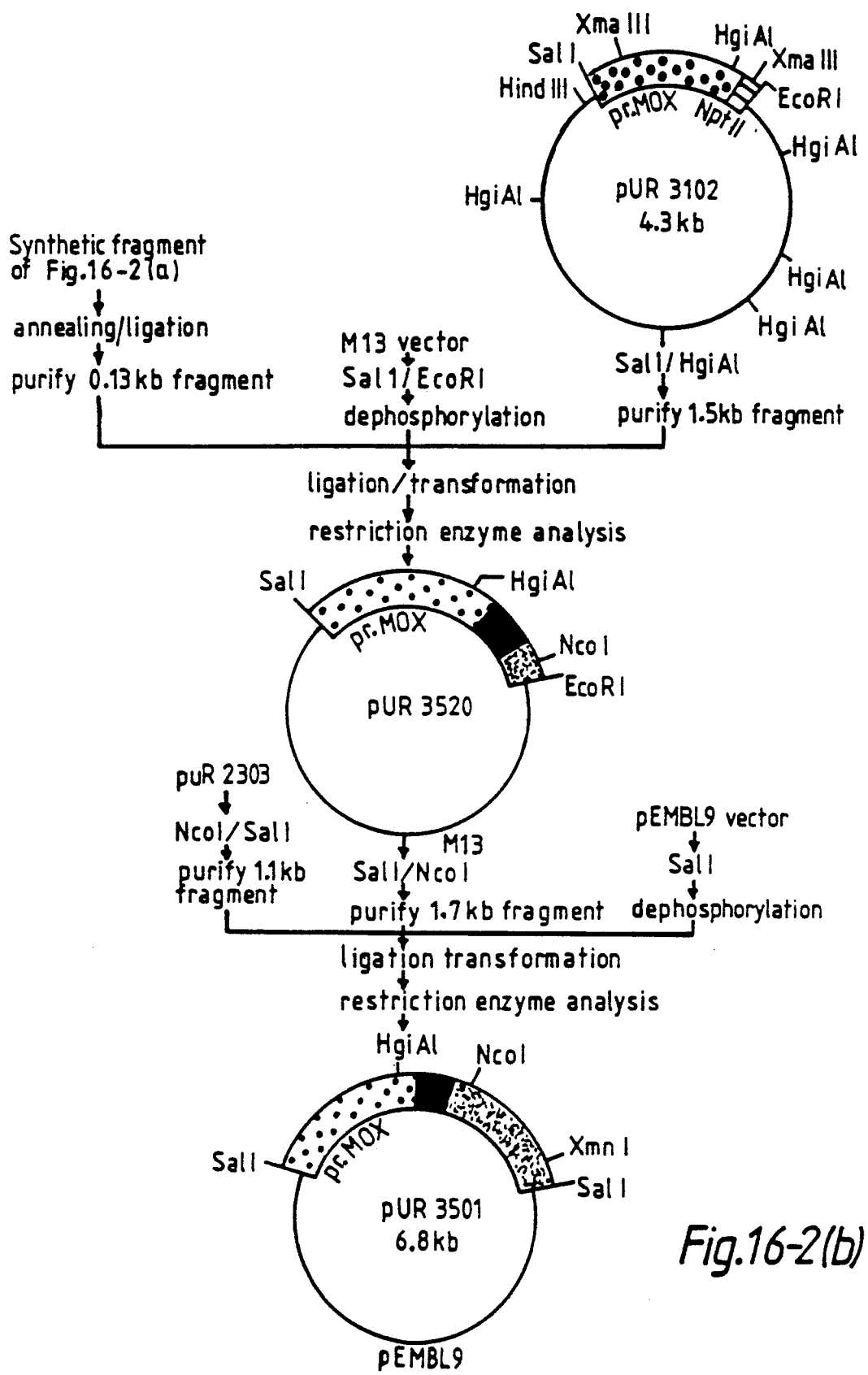
Figures 3, 16:
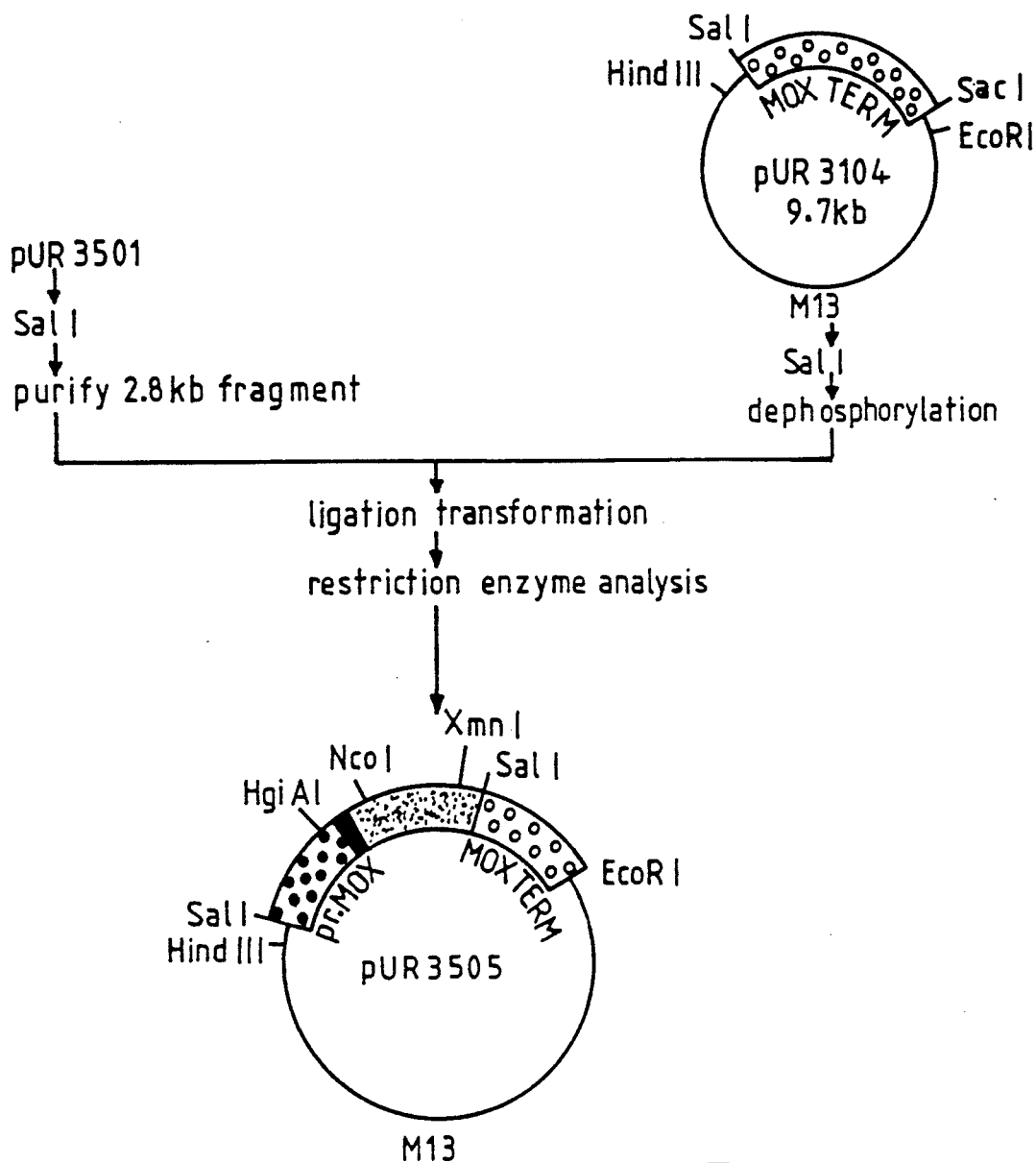
Figure 16:
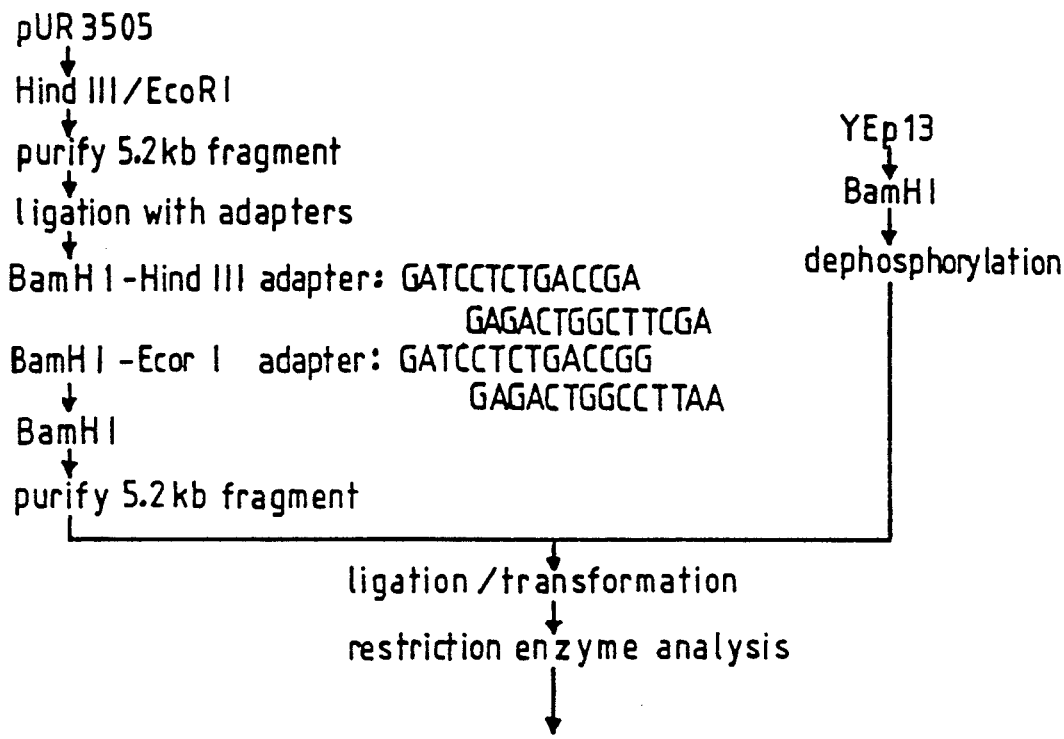
Figure 4:
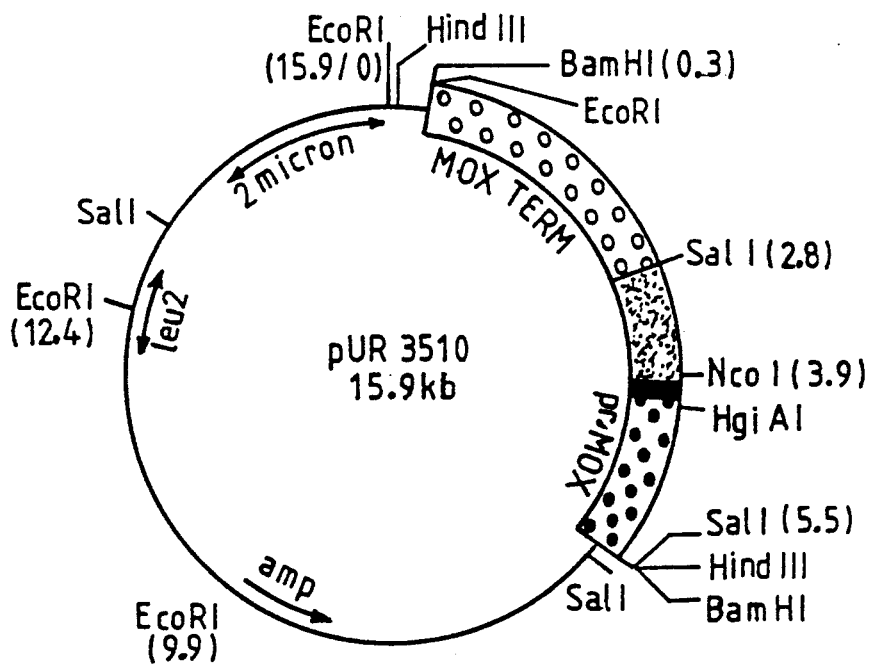
Figure 17:
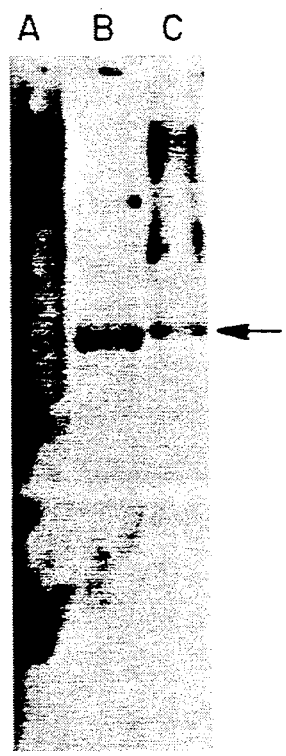

As probes for the mRNA encoding alpha-galactosidase, we used oligonucleotides based on amino acid sequences which we had established for a part of the $NH_2$-terminus and for an internal peptide (see FIG. 3).

From the purified protein, the N-terminal amino acid sequence analysis was determined directly through Edman degradation (Edman and Begg: 1967), using a Beckman 890c spinning cup protein sequenator. The internal peptide was sequenced similarly after cleavage of the purified protein with cyanogen bromide and trypsine, after which the peptide was purified to homogeneity from the other peptides by column chromatography. Based on the established amino acid sequence, all the possible nucleotide sequences encoding the amino acid sequence were derived. Deoxy-oligonucleotides containing all or part of the possible nucleotide sequences (so-called mixed probes) were synthesized on a DNA synthesizer (Applied Biosystems) using the phosphite technique (Matteuci and Caruthers, 1981). Oligonucleotides were purified on 16% or 20% polyacrylamide gels (Maniatis et al., 1982).

Usually, 0.1–0.3 µg of the purified oligonucleotide was labelled by incubation for 30 minutes at 37° C. in 50 mM Tris-HCl pH 7.5, 10 mM $MgCl_2$, 0.1 mM EDTA, 10 mM dithiothreitol (DTT), 70 µCi gamma-$^{32}$P-ATP (3000 Ci/mmol, Amersham), 10 units T4 polynucleotide kinase (Amersham) in a final volume of 15 µl. The reaction was terminated with 10 µl 0.5M EDTA pH 8.0 and extracted with phenol/chloroform (1:1). The water phase was passed through a Sephadex G25 column of 2.5 ml (disposable syringe) equilibrated with TE buffer (10 mM Tris-HCl pH 8.0 and 1 mM EDTA). Fractions of 250 µl were collected, from which the first two radioactive fractions, usually fractions 4 and 5, were pooled.

1.2.4.2. Northern Blot Hybridization

Purified RNA was separated by electrophoresis in the presence of formaldehyde as described (Lehrach et al., 1977). To 5 µl of RNA dissolved at 1 µg/µl in a mixture of 10 mM Tris-HCl pH 7.5, 1 mM EDTA, 0.1M NaCl and 0.1% SDS was added: 10 µl formamide (BDH Chemicals), 3.3 µl filtered formaldehyde (Merck) and 2 µl 10×MOPS buffer (0.2M MOPS pH 7.0, 10 mM EDTA). The samples were heated for 15 minutes at 70° C. chilled on ice and applied to a 1% agarose gel (1 g agarose was dissolved by boiling in 73 ml $H_2O$; after cooling to 65° C. was added 10 ml 10×MOPS buffer and 16.5 ml formaldehyde). Electrophoresis was performed in 1×MOPS buffer at 30–40 mA for 3–5 hours. RNA was visualized by staining for 30 minutes with ethidium bromide (1 µg/ml in 0.1M ammonium acetate), destaining for 30–60 minutes in distilled water and exposure to long wave UV light.

Subsequently, the RNA was transferred by capillary blotting to Gene Screen Plus (Dupont NEN) with 10×SSC (1.5M NaCl, 0.15M Na citrate) according to the instructions of the manufacturer. The transfer was allowed to continue for 20 hours. After rinsing in 2×SSC, the membrane was baked for 2 hours at 80° C. under vacuum.

Prior to hybridizaiton, the membranes were prehybridized for 4–5 hours at 65° C. in a mixture of 5×SSC, 2×Denhardts (10×Denhardts: 0.1% Ficoll, 0.1% polyvinylpyrrolidone, 0.1% Bovine Serum Albumin), 1% SDS and 100 µg/ml sheared (sonication) and denatured (boling for 2 minutes) calf thymus DNA. Hybridization was performed in this same buffer supplemented with the $^{32}$p-labelled oligonucleotide probe at 30° C. with continuous agitation.

After this hybridization, the membranes were washed with 5×SSC (3 times for 15 minutes at room temperature) and subsequently with 5×SSC with 0.1% SDS at 30° C. for 30 minutes. More stringent washes at higher temperature and/or lower salt concentration have been performed as indicated.

The results showed (FIG. 4) that probe MP33 hybridized specifically with an mRNA of about 1600 nucleotides. An mRNA of this size is capable of encoding a protein of up to 45 kd.

From the results of these experiments, in vitro translation and Northern blot hybridization, we concluded that our hypothesis was correct: the alpha-galactosidase is synthesized upon germination in the aleurone cells of the endosperm of guar seeds.

1.3 Construction of a cDNA Library From mRNA of Aleurone Cells From Guar Seed A method for cDNA synthesis was used based on the procedure described by Gubler and Hoffman (1983). 3/µg poly-A RNA dissolved in 10 µl $H_2O$ was annealed with 2.5 µg oligo-dT 12–18 in 10 µl $H_2O$ (Collaborative Research) by heating at 100° C. for 30 seconds and chilling on ice-water for another 30 seconds. The complementary strand was synthesized by incubation for 45 minutes at 43° C. after addition of 30 µl of Mix I [prepared just before use from 25 µl 2×RT buffer freshly made (0.1M Tris-HCl pH 8.3 at 43° C., 10 mM $MgCl_2$, 150 mM KCl, 20 mM DTT, 1 mM dATP, 1 mM dGTP, 1 mM dCTP, 0.2 mM TTP), 40–50 units reversed transcriptase (Anglian Biotechnology) and distilled water to 30µl]. The reaction was arrested by placing in ice-water for 2 minutes.

Immediately thereafter a second strand was synthesized by adding to the mixture containing the first strand 150 µl Mix II (prepared just before use at 0° C.: 40 mM Tris-HCl pH 7.5, 10 mM $MgCl_2$, 75 mM KCl, 25 µg/ml bovine serum albumin [Dnase and RNase free; Bethesda Research Laboratories]); 2 µl alpha-$^{32}$p-TTP [3000 Ci/mmol; Amersham]; 40 units DNA polymerase I and 8 units RNase H [both from Anglian Biotechnology]). The reaction was for 60 minutes at 11° C. Ligation was subsequently performed by adding directly 2 µl 20 mM ATP and 400 units T4-DNA ligase (Biolabs) and incubation for 2 hours at 18° C. The reaction was arrested by adding 20 µl 0.4M EDTA and 1 µl 20% SDS.

The ds-cDNA obtained was purified by gel filtration on Sephadex G-50 (10 ml column) equilibrated with 10 mM Tris-HCl pH 7.5, 0.3M NaCl and 1 mM EDTA. Fractions of 150 µl were collected, radioactivity determined directly on the fractions without adding scintillation fluid (so called Cerenkov counting) and the DNA-containing fractions were pooled. The ds-cDNA was precipitated with alcohol, dissolved in a mixture of 10 mM Tris-HCl pH 7.5, 0.3M NaCl, 1 mM EDTA, 0.1% SDS and size-fractionated on a Sepharose CL-4B (Pharmacia) column (2 ml in a pasteur pipette) equilibrated with the same buffer. Fractions of about 100 µl were collected and analysed for the length of the cDNA by electrophoresis on an agarose gel followed by autoradiography. Fractions with ds-cDNA larger than 500 bp were pooled and precipitated with alcohol. The ds-cDNA was dissolved in 10 µl $H_2O$.

Homopolymer dC-tailing was performed by adding to 10 µl ds-cDNA: 4 µl 5×TdT buffer (1M sodium cacodylate pH 7.0, 10 mM $CoCl_2$, 0.5 mM dCTP), 3.4 µl $H_2O$, 0.6 µl 5 mM DTT. The sample was incubated at 37° C. for 2 minutes, supplemented with 2 µl terminal transferase (20 units/µl; Bethesda Research Laboratories) and incubated for 8 minutes at 37° C. The reaction was arrested by adding 1 µl 0.5 M EDTA and 20 µl phenol. After mixing, 10 µl of chloroform was added, mixed and centrifuged for 2 minutes. The phenol layer was re-extracted, the water phases pooled, extracted twice with ether to remove the phenol, transferred to a new Eppendorf tube (coated with dichloordimethylhydroxy silane) and the DNA precipitated with ethanol.

The dC-tailed ds-cDNA was dissolved in a mixture of 20 µl 10 mM Tris-HCl pH 7.5, 1 mM EDTA and 0.1M NaCl (annealing buffer). The ds-cDNA was annealed with G-tailed vector (pBR322 cleaved with PstI and homopolymer dG-tailed, purchased from Dupont NEN) in a ratio of about 4 ng ds-cDNA, 25 ng vector in a final volume of 25 µl by heating at 65° C. for 10 minutes, followed by slow cooling to 4° C. These annealed samples were used to transform $E.\ coli$ strain 294 (endo I−, $B_1^-$, $r_k^-$, $m_k^+$; Backman et al., 1976) by the "Hanahan" procedure described in Maniatis et al. (1982). This resulted in a clone-bank of $3 \times 10^4$ clones.

1.4 Selection of Clones Containing the Guar Alpha-Galactosidase Genetic Information Samples of transformed $E.\ coli$ cells were spread directly on nitrocellulose filters (Millipore type HATF, 0.45 µm) placed on agar plates with tetracycline (10 µg/ml), such that $(3-5) \times 10^3$ colonies were present per filter after overnight incubation at 37° C.

Two identical replicas were obtained from one master filter as follows: The master filter was placed onto dry paper filters and marked. A first nitrocellulose replica filter was wetted on a fresh L-broth agar plate and placed on top of the master filter. Four paper filters were placed upon the replica filter and pressed down very carefully using a glass spatula. The four paper filters were removed, the orientation marks precisely copied on the replica, the replica filter placed on an L-broth agar plate (side with colonies up) and the procedure was repeated for the second replica. The replica filters were grown for 3-5 hours at 37° C. until colonies were visible, and transferred to L-broth agar plates containing chloramphenicol (150 µg/ml), followed by incubation at 37° C. overnight. The master filter was replaced on an agar plate with tetracycline and stored at 4° C.

The bacteria on the replica filters were lysed by placing them on a stack of Whatmann 3 MM papers saturated with 0.5M NaOH and 1.5M NaCl for 15 minutes. After removal of excess of fluid from the filters by placing them on dry paper, neutralization was subsequently performed by placing the filters on paper saturated with 1M Tris-HCl pH 7.0 and 1.5M NaCl for 2-3 minutes. Finally, the filters were dunked into $3 \times SSC$ for 15-20 seconds, air dried and baked at 80° C. under vacuum for 2 hours.

Prior to (pre)hybridization, the filters were washed extensively in $3 \times SSC$ 0.1% SDS at 65° C. for 16-24 hours with several changes of buffer. The washing was complete was the colony- prints were not visible any more. Prehybridization was performed for 2 hours at 37° C. in Premix A ($5 \times SSC$, $5 \times Denhardts$, 0.1% SDS, 50 mM sodium phosphate pH 7.5, 1% glycine, 25 µg/ml calf thymus DNA, 75 µg/ml $E.\ coli$ DNA (Sigma type VIII; both DNA preparations were sheared and denatured), 500 µg/ml tRNA, 50% deionized formamide). Hybridization was performed in hybridization mix A ($5 \times SSC$, $1 \times Denhardts$, 0.1% SDS, 20 mM sodium phosphate pH 7.5, 25 µg/ml calf thymus DNA, 75 µg/ml $E.\ coli$ DNA, 500 µg/ml tRNA, 50% deionized formamide) with the oligonucleotide probe MP44 (see FIG. 3) labelled with gamma- $^{32}$p-ATP essentially as described above for probe MP33. Hybridization was performed overnight at 30° C. Subsequently, the filters were washed for $3 \times 15$ minutes with $6 \times SSC$ at room temperature, $1 \times 15$ minutes with $2 \times SSC$, 0.1% SDS, and finally for 15 minutes at 37° C. in prewarmed $0.1 \times SSC$ with 0.1% SDS. The filters were dried and exposed to X-ray film overnight at −70° C. Colonies which gave a positive signal on both replicas were picked from the master plate.

From 8 positive clones plasmid DNA was purified, using the alkaline lysis method described by Birnboim and Doly (1979), digested with PstI (Amersham) and analysed after electrophoresis on 1% agarose gels (Maniatis et al., 1982). In all 8 cases the plasmid DNA contained the vector fragment (4.3 kb); 7 of them contained both an identical 1250 bp DNA fragment and a smaller fragment ranging in size from 300-500 bp. Two independently isolated clones were elected resulting in: pUR2302, a plasmid with a cloned insert of about 1750 bp and pUR2314 with an insert of about 1550 bp.

$E.\ coli$ strain 294 containing plasmid pUR2302 was deposited under the Budapest Treaty at the Centraalbureau voor Schimmelcultures (CBS), P.O. Box 273, 3740 AG Baarn, The Netherlands, on 30th May 1986 and acquired provisional deposition number CBS 267.86.

1.5 Determination of the Nucleotide Sequence of the Guar Alpha-Glactosidase cDNA Clone and the Derived Amino Acid Sequence of the Alpha-Galactosidase Enzyme Plasmids pUR2302 and pUR2314 were digested with PstI, resulting in fragments of 1250 bp+500 bp and 1250bp+300 bp, respectively, in addition to the vector fragment. These four fragments were purified separately by excision from a 1% agarose gel after electrophoresis followed by electroelution into dialysis bags (Maniatis et al., 1982). The purified fragments were ligated with vector M13mp18 (purchased from Bethesda Research Inc. and described by Norrander et al., 1983), cleaved with PstI and the ligated samples used to transform $E.\ coli$ strain JM103 (described by Messing et al., 1981) with the CaCl$_2$ procedure and plated on L-broth supplemented with X-gal and IPTG (Maniatis et al., 1982).

From the resulting colourless plaques, single-stranded phage DNA was isolated and used for the establishment of the nucleotide sequence by the Sanger dideoxy chain termination procedure with the modifications described by Biggin et al. (1983), using alpha-$^{35}$S-dATP (2000 Ci/mmol) and Klenow enzyme (Amersham), ddNTP's (Pharmacia-PL Biochemicals), and dNTP's (Boehringer). The sequencing reaction products were separated on a denaturing polyacrylamide gel with a buffer gradient as described by Biggin et al. (1983).

Figure 5:
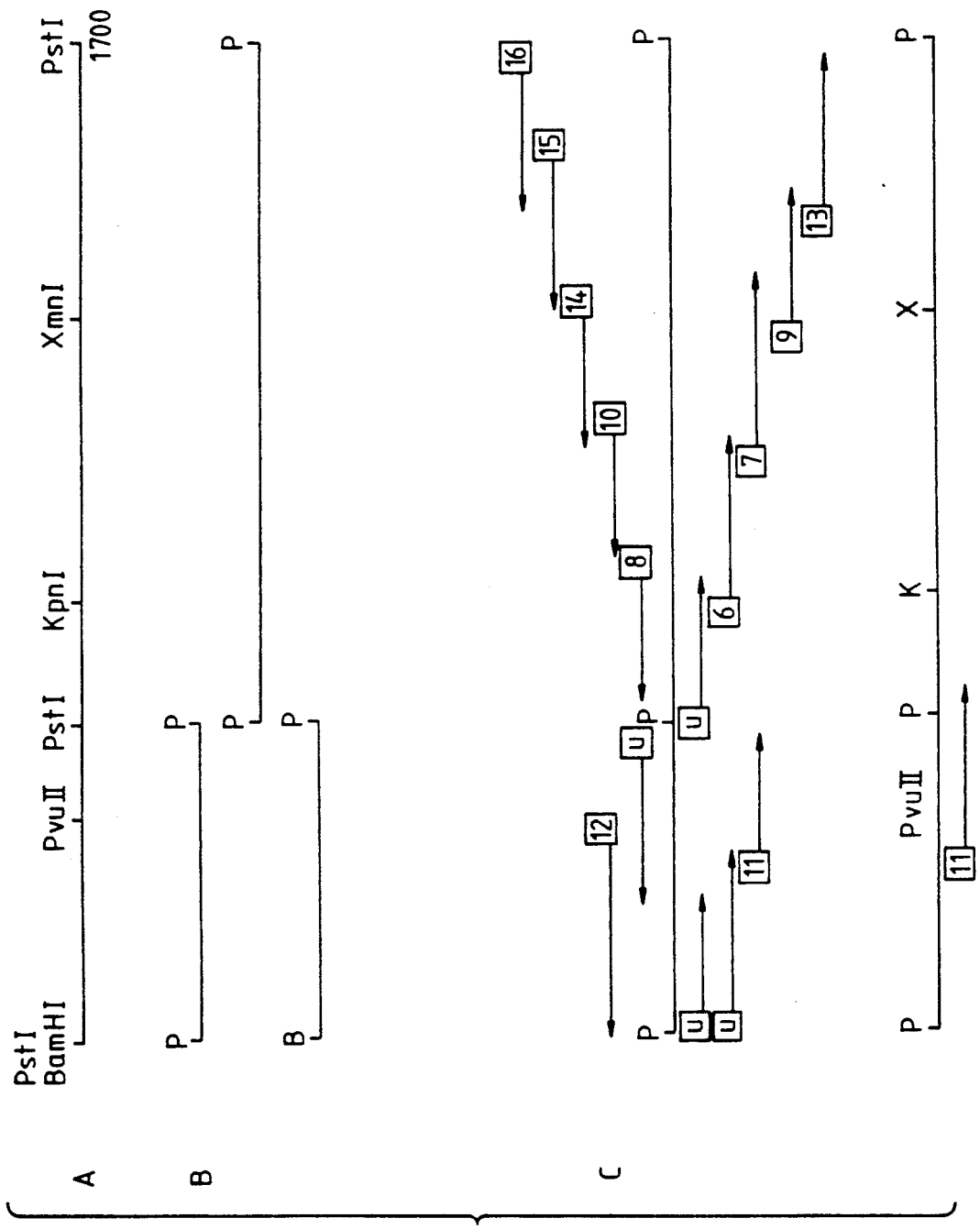

The nucleotide sequence was determined using a cascade-like approach (see FIG. 5). The nucleotide sequence at the borders of the subcloned fragments was determined first by using the universal M13 sequencing primer (obtained from Amersham). At the most distal position where the sequence data were still reliable, sequencing was continued using two new sequencing primers especially synthesized as described above, one for the continuation of the nucleotide sequence in the 3'-5' direction and the other one for the sequencing of the complementary strand. By this cascade-like approach, the complete nucleotide sequences for the subclones of both clones pUR2302 and pUR2314 have been established. The nucleotide sequence surrounding the internal PstI site was determined using the super-coiled sequencing procedure described by Chen and Seeburg (1985). The result showed that both PstI-fragments are joined directly.

The complete nucleotide sequence of the guar alpha-galactosidase cDNA clone is shown in FIG. 6. The nucleotide sequence starting with nucleotide 263 up to the poly-A-tail in plasmid pUR2302 (see FIG. 6) is identical with the nucleotide sequence of the insert of plasmid pUR2314.

Analysis of the nucleotide sequence shows (FIG. 6) an open translational reading frame encoding 411 amino acid residues with the first methionine at nucleotide position 166 and two consecutive translation stop codons at nucleotide position 1399-1404. The deduced amino acid sequence is shown in the IUPAC one-letter notation above the nucleotide sequence in FIG. 6.

The NH$_2$-terminal amino acid sequence of the alpha-galactosidase enzyme purified from guar seed has been identified as AENGLGQTPP.... (see above and FIG. 3). This amino acid sequence is encoded by nucleotides 307-336 (FIG. 6). Firstly, from these findings it can be concluded that the mature alpha-galactosidase enzyme is composed of 364 amino acid residues which have a calculated molecular weight of 39,777 dalton. This agrees well with the molecular weight of 40,500 dalton estimated by SDS-polyacrylamide gel electrophoresis (McCleary, 1983).

Secondly, the natural enzyme is most likely synthesized in a precursor form with a 47 amino acid residues extension (numbered −47 to −1 in FIG. 6).

As the internal peptide DYLKYDN (see FIG. 3) was found in the nucleotide sequence (nucleotide 680 to 701) in addition to the NH$_2$-terminal peptide, it can be definitely concluded that the alpha-galactosidase enzyme from guar was cloned.

EXAMPLE 2

Production of the Guar Alpha-Galactosidase By Genetically Engineered Saccharomyces Cerevisiae To illustrate the production of guar alpha-galactosidase by micro-organisms, we constructed vectors suited for expression of guar alpha-galactosidase in *Saccharomyces cerevisiae* using a constitutive GAPDH promoter.

Genetic Engineering of Vectors pURY2703 and pURY2705

Figure 14:
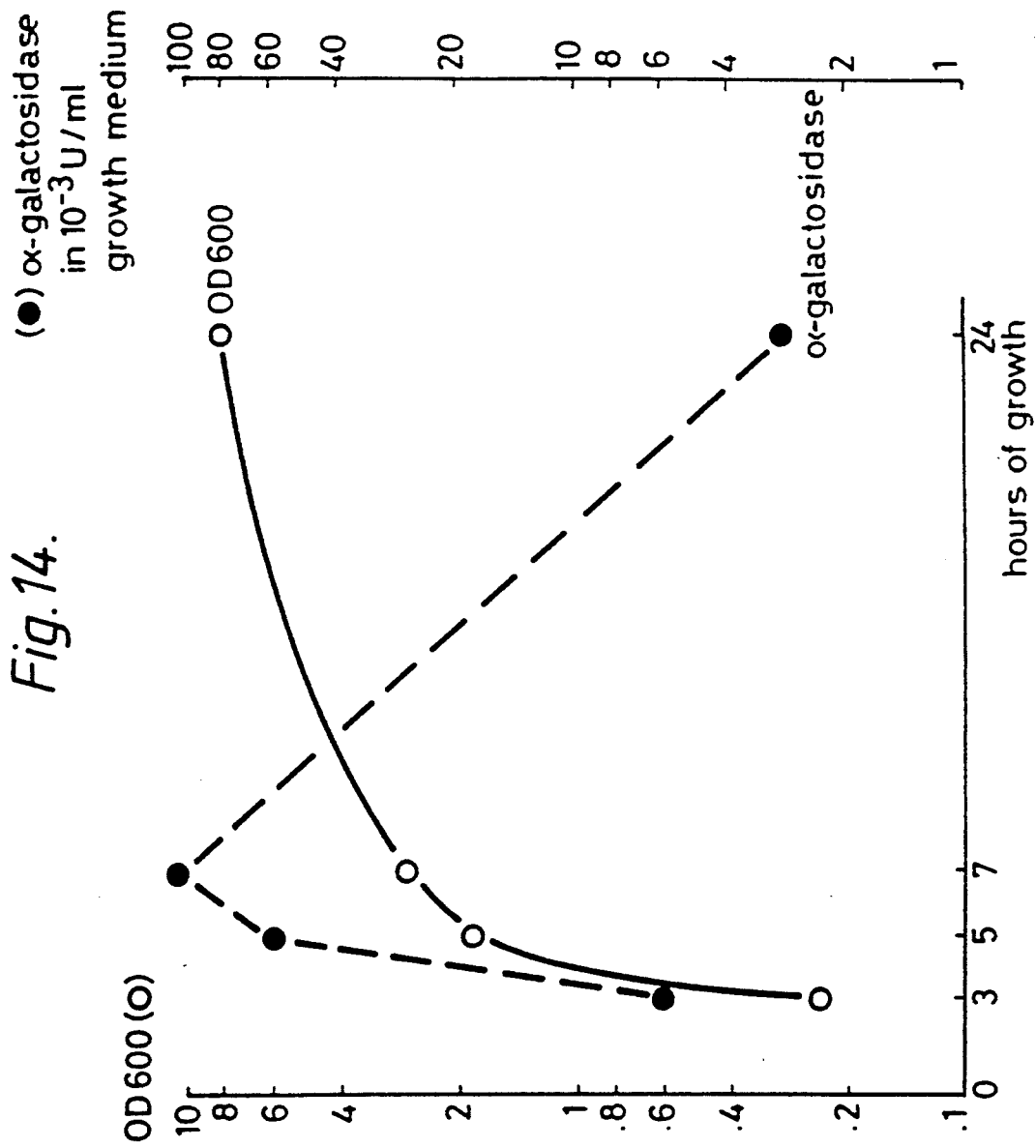
Figure 15:
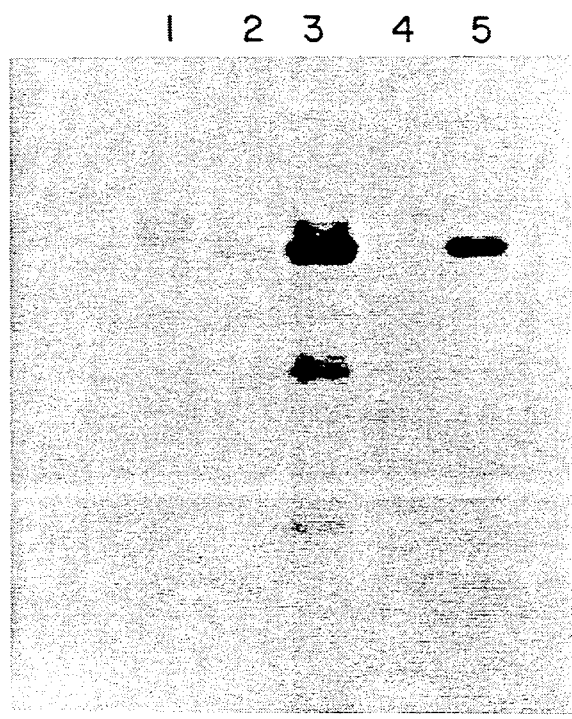

As a basis for these vectors, the *E. coli* - *S. cerevisiae* shuttle vector pURY528-03 was used (Edens et al., 1984, EPO 0 129 268, FIG. 14; *Saccharomyces cerevisiae* AH22 containing plasmid pURY528-03 was deposited on May 19, 1983 at the Centraalbureau voor Schimmelcultures, P.O. Box 273, 3740 AG Baarn, The Netherlands, under number CBS 8155), which contains for expression in *S. cerevisiae* the preprothaumatin gene under control of the GAPDH promoter. The strategy was as follows (see FIG. 7): From the vector pURY528-03 the SacI-HindIII fragment was deleted, containing the complete preprothaumatin gene and 23 basepairs upstream of the preprothaumatin ATG translation start codon.

Subsequently, a synthetic fragment was added. In the case of pURY2703 (see FIG. 7) it contains the above-mentioned 23 basepairs, the ATG as a translation start codon, an additional ala-codon and the NH$_2$-terminal part of the mature alpha-galactosidase gene starting as ala$^1$ up to the PvuII site which is around amino acid residue 31 of the mature protein (FIG. 6). The DNA encoding these amino acid residues was synthesized in yeast preferred codons (Tuite et al., 1982). In the case of pURY2705 (see FIG. 7) it contains the above-mentioned 23 basepairs, the SUC2 (invertase) signal sequence, as published by Taussig and Carlson (1983) and the mature alpha-galactosidase gene from residue ala$^1$ up to the PvuII site in yeast preferred codons. The nucleotide sequence and construction of these synthetic fragments is given in FIG. 8.

The synthetic oligonucleotides were made on a DNA synthesizer (Applied Biosystems) as described (Example 1) and purified by electrophoresis on a polyacrylamide gel. The eluted DNA was dissolved in 50 $\mu$l TE (10 mM Tris-HCl pH 7.6, 1 mM EDTA) after which the concentration was determined by measuring the optical density at 260 nm. With the exception of the border fragments with the free 5' end, 0.5 $\mu$g of every individual fragment was pooled and phosphorylated in a final volume of 100 $\mu$l by the enzyme polynucleotide kinase. After phenol extraction and alcohol precipitation, the pellet was dissolved, 0.5 $\mu$g of each of the border fragments added and annealing performed in ligation buffer without DTT and ATP. Annealing was performed by heating at 70° C. for 10 minutes, followed by slow (2 hours) cooling to 30° C. After addition of DTT and ATP (final concentrations 10 mM and 0.5 mM, respectively) and T4 ligase enzyme, ligation was done at 15° C. for 18 hours. The synthetic fragment was subsequently electrophoresed on a 2% agarose gel, the band with the desired length excised and isolated by electroelution from the gel. The purified fragment was ligated to an appropriate vector (pEMB L9; Dente et al., 1983) and the ligation mixture used to transform *E. coli* cells from strain JM103. Plasmids were purified from these transformants and the synthetic fragments analysed by DNA sequence determination.

Finally, the genetic information encoding the remaining 333 residues of the mature alpha-galactosidase gene was added. The 1.4 kb PvuII-BglI fragment was obtained from plasmid pUR2302, while the BglI site had been converted into a HindIII site (see FIG. 7). The final ligation mix was used to transform *E. coli* strain 294. Plasmids were purified from the transformants and plasmids with the correct restriction enzyme patterns were selected, resulting in plasmids pURY2703 (FIG. 9) and pURY2705 (FIG. 10).

Transformation and Analysis of *S. cerevisiae* with pUry2703 and pURY2705

Yeast cells of *S. cerevisiae* strain AH22 (a, leu2, his4, described by Hinnen et al., 1978) were transformed with plasmids pURY2703 and pURY2705 by the spheroplast method according to the procedure described by Beggs (1978). The resulting leu$^+$ transformed yeast colonies were screened directly on the agar plates for the presence of the alpha-galactosidase enzyme by an overlay of molten agar with the substrate p-nitrophenyl alpha-D-galactopyranoside (pNPG; Sigma) as described by Buckholz and Adams (1981).

This showed that no alpha-galactosidase enzyme is present at detectable levels around yeast cells with plasmid pURY2703. The appearance of yellow colour around cells with plasmid pURY2705, however, showed that, with the latter plasmid, biologically active enzyme was present outside the cells.

Next to the analysis of intact cells, also crude cell extracts were analysed. Yeast cells with plasmids pURY2703 and pURY2705 were grown on Yeast Minimal Medium (0.67% yeast nitrogen base without amino acids, Difco; 2% glucose) supplemented with histidine (20 μg/ml) to an optical density at 600 nm of 1.0. Yeast cells were harvested, resuspended in extraction buffer (10 mM Tris-HCl pH 8.0, 0.1 mM EDTA, 1 mM DTT) at a concentration of $10^{10}$ cells/ml and disrupted either by three freeze-thaw cycles or by passing through a French pressure cell.

An appropriate dilution of crude cell extract in extraction buffer was incubated with 10 mM pNPG in 0.1 M sodium acetate pH 4.5 for 5 minutes at 37° C. The reaction was stopped by addition of 1 ml 2% sodium carbonate. The absorbance of the resulting mix was determined at 410 nm after removal of cells and cell debris by centrifugation for 5 minutes in an Eppendorf centrifuge. The extinction coefficient of p-nitrophenol at 410 nm is 18.4 $cm^2/\mu mole$. One unit of alpha-galactosidase is defined as the amount of enzyme which hydrolyses 1 μmole of substrate in 1 minute at 37° C. at pH 4.5.

The results showed that about (1-2.5) $\times 10^{-3}$ units were present in $10^8$ yeast cells with plasmid pURY2703 and about (3-5)$\times 10^{-3}$ units were present in $10^8$ yeast cells with plasmid pURY2705.

For the immunological assay we used a so-called Western blot analysis. After addition of sample buffer (Edens et al., 1982) to the crude cell extracts, they were boiled for 5 minutes.

Purified proteins were applied in gel sample buffer after heating for only 2 minutes. Proteins were separated by electrophoresis on 10% polyacrylamide gels according to Wyckoff et al. (1977).

Proteins were subsequently transferred from the gel onto nitrocellulose by electrophoretic transfer (ref. Burnette, 1979). The nitrocellulose was rinsed with incubation (I) buffer (150 mM NaCl, 5 mM EDTA, 50 mM Tris.HCl pH 7.0, 0.05% Triton X-100, 0.25% gelatin) and incubated in I-buffer with 0.1% BSA and antiserum raised by immunization of rabbits with alpha-galactosidase purified from guar.

Incubation was at room temperature for 4 hours with agitation. Unabsorbed antibodies were removed by washing with I-buffer (2 times) and phosphate buffered saline pH 7.0 (PBS). Antibodies bound to antigen were detected by reaction with $^{125}I$ Protein A (Amersham) for 1 hour. After washing with I-buffer (2 times) and PBS (3 times), the nitrocellulose was dried and exposed to X-ray film at −70° C.

The results (FIG. 11) showed that cells with plasmid pURY2705 (lane 3) produce an alpha-galactosidase enzyme which has a positive reaction with guar alpha-galactosidase specific antibodies and with the same molecular weight as the plant enzyme (lanes 1 and 2). Yeast cells with plasmid pURY2703 (lane 4) produce an alpha-galactosidase emzyme with a positive immunological reaction but which has a slightly lower molecular weight. Yeast cells without a plasmid (lane 5) produce no enzyme immunologically related with guar alpha-galactosidase.

It can be concluded that both plasmids, pURY2703 and pURY2705, produce an enzymatically active product which has a positive reaction with antibodies raised against alpha-galactosidase purified from guar. In the first case the enzyme has a slightly lower molecular weight than the plant enzyme and is present in the cytoplasm of the cells. In the second case the enzyme has the same molecular weight as the plant enzyme and is present outside the cells (the latter most likely as the result of targeting the protein to the endoplasmatic reticulum where glycosylation and secretion can follow).

EXAMPLE 3

Reduction of the Galactose Content of Galactomannans by the Alpha-Galactosidase Enzyme Produced by Genetically Engineered S. cerevisiae S. cerevisiae strain AH22 harbouring plasmid pURY2705 produced (3-5)$\times 10^{-3}$ units/$10^8$ cells of alpha-galactosidase enzyme when grown on Yeast Minimal Medium (YMM; see Example 2). This production level could be increased up to 0.1 unit/$10^8$ cells, when the yeast cells grown to late exponential phase on YMM were transferred to rich YPD medium (2% glucose; 2% Bactopeptone, Difco; 1% yeast extract, Difco) and grown for about 4 hours.

In another experiment yeast cells were grown in 200 ml YMM to an ooptical density at 600 nm of 1.5, transferred to 1 liter YPD medium and grown for an additional 4 hours at 30° C. The cells were harvested, resuspended in 4 ml of extraction buffer and passed through a French pressure cell (5 cycles). The resulting suspension was cleared by ultracentrifugation (Sorvall SW60, 30,000 rpm, 1 hour at 4° C.). More than 90% of the enzyme activity was present in the clear supernatant. Finally, the clear suspension was incubated for 15 minutes at 37° C. with 40 μl RNase (10 mg/ml, Boehringer) and 100 μl DNase (2 units/μl, Amersham) to yield a crude yeast cell extract which contained about 10 units alpha-galactosidase/ml. This extract was used in an experiment to decrease the galactose content of guar gum essentially as described by McCleary et al., 1984; EP-A- 0 121 960.

The enzymes used were:
crude yeast extract (described above) as an example, *Saccharomyces carlsbergensis* alpha-galactosidase for comparison: the latter was purified as follows:

*S. carlsbergensis (ATCC* 9080) was cultured in a modified YMM wherein the glucose was replaced by galactose (20 g/l) at 26° C. At stationary phase the cells were harvested by centrifugation, and the supernatant concentrated and dialysed against acetate buffer (0.1 M, pH 4.5), first in an Amicon DC-2 Concentrator, and then against PEG (ex Sigma). This preparation was used without further purification.

Guar flour (Guar Gum THI from Hercules; 1 gram) and enzyme (10 units in 1.5 ml 0.1M sodium acetate pH 4.5) were mixed until the mixture resembled fine breadcrumbs. It was placed in a closed container and incubated at 55° C. Samples (100 mg) were withdrawn at the times indicated, the reaction stopped by heating to 100° C. and the galactose content of the polysaccharide determined.

| Source of enzyme | % galactose in galactomannan after. | | | |
|---|---|---|---|---|
| | 0 hr | 1.5 hr | 3.5 hr | 6 hr |
| yeast | 38 | 35 | 34 | 32 (example) |
| S. carlsbergensis | 38 | 38 | 38 | 38 (comparison) |

These results clearly show that the heterologous "guar alpha-galactosidase" produced by *Saccharomyces cerevisiae* is capable of decreasing the galactose content of galactomannans, whereas the homologous yeast alpha-galactosidase enzyme produced by *Saccharomyces carlsbergensis* is not capable of decreasing the galactose content under the preferred conditions.

The experiments described above (Examples 2 and 3) clearly demonstrate that an alpha-galactosidase enzyme free of beta-mannanase and capable of decreasing the galactose content of galactomannans can be produced by transformed micro-organisms such as the yeast *Saccharomyces cerevisiae* used in Example 3.

EXAMPLE 4

Immunological Relationship and Gum Modification Capacity for Various Alpha-Galactosidase Enzymes

4.1. Source of Alpha-Galactosidase Enzymes

The enzyme activities were determined by hydrolysis of p-nitrophenyl-alpha-D-galactopyranoside(pNPG) at the optimal temperature and pH in a reaction volume of 45 μl with 10 mM pNPG for 5 minutes. The reaction was stopped by addition of 1 ml 2% sodium carbonate. The absorbance of the resulting mix was determined at 410 nm, where appropriate, after removal of cells and cell debris by centrifugation for 5 minutes in an Eppendorf centrifuge. The extinction coefficient of p-nitrophenol at 410 nm is 18.4 $cm^2/\mu mole$. One unit of alpha-galactosidase is defined as the amount of enzyme which hydrolyses 1 μmole of substrate in 1 minute.

*E. coli* alpha-galactosidase was obtained from Boehringer (cat. No. 662038, lot No. 1503401) as a freeze-dried powder, 50 U in 18 mg. *A. niger* alpha-galactosidase was from Sigma (cat. No. G 9007, lot No. 105c/8640) as a suspension in 3.5M ammonium sulphate, 50 mM sodium acetate, pH 5.5, 48 U in 2.7 ml. GREEN COFFEE BEAN alpha-galactosidase was from Boehringer (cat No. 105 023, lot No. 10118722-20) as a suspension in 3.2M ammonium sulphate, pH about 6, 83 U in 1.0 ml. *Saccharomyces carlsbergensis* (ATCC 9080) was cultured at 26° C. in minimal medium: yeast nitrogen base without amino acids, Difco (6.7 g/l) and galactose (20 g/l). At stationary phase, the cells were harvested by centrifugation. The supernatant was concentrated and dialysed against acetate buffer (0.1M, pH 4.5), first in an Amicon DC-2 Concentrator and then against polyethylene glycol (ex Sigma). This preparation yielded about 20 U per liter of culture supernatant.

GUAR alpha-galactosidase was prepared as described by McCleary (1983). LUCERNE and FENUGREEK enzymes were prepared by an essentially identical route, involving germination for 2.5 days (about 100% fenugreek seeds germinated, about 50% lucerne seeds germinated), homogenisation in acetate buffer, centrifugation, filtration through nylon mesh, and precipitation in 50% w/v ammonium sulphate. Precipitates were dissolved in about 20 ml 0.1M acetate buffer (pH 4.5) and used without further purification. From 200 g seeds, this protocol yielded 1050 U fenugreek enzyme and 65 U lucerne enzyme.

CAROB seeds were germinated using the method of Seiler (1977). Seeds were scored with coarse sandpaper to partially remove the hard seed coat, sterilised for 5 minutes in 70% ethanol/water, soaked for 48 hours in deionised water, and germinated on moist chromatography paper for 9 days at 26° C. Germinated seeds were extracted as described above, 9 carob seeds yielding 7 U alpha-galactosidase.

4.2. Enzymes Produced by Genetically Engineered Microorganisms: *Saccharomyces cerevisiae*, *Kluyveromyces marxianus* var. *lactis*, *Hansenula polymorpha* and *Bacillus subtilis*

The genetic information encoding the guar alphagalactosidase was engineered in various vectors (see Examples 2, 5, 6, 8 and 9) and expressed in the various micro-organisms either extracellular or intracellular.

For *S. cerevisiae* and *B. subtilis*, purified enzyme preparation were used. Therefore, cells with vectors were used which gave rise to secretion of the enzyme in the growth medium.

After removal of the cells from the fermentation broth by microfiltration (0.22 μm), lower molecular weight substances were removed by desalting, using a PD-10 column (Pharmacia) equilibrated with 0.03 M TRIS-HCl pH 8.0. Alpha-galactosidase was isolated from this fraction by anion-exchange chromatography, using a MONO-Q column (HR 5/5, Pharmacia). Elution was achieved by a NaCl gradient (0–1 M) in 0.03 M TRIS-HCl pH 8.0. Detection was at 214/280 nm using the Pharmacia FPLC system.

Fractions containing alpha-galactosidase activity (eluting at about 0.3 M NaCl) were pooled and desalted (PD-10 column, eluent 0.01 M Na-acetate pH 4.5).

The enzyme preparations were further concentrated about 10-fold by vacuum drying.

For *K. marxianus* var. *lactis* and *H. polymorpha* crude cell extracts were used. Cells were grown on agar plates under appropriate conditions, harvested, suspended in extraction buffer (10 mM Tris pH 8.0, 0.1 mM EDTA, 1 mM DTT) and disrupted by three cycles freeze-thaw.

Immunological Relationship Analysed by Ouchterlony Double Diffusion

A solution of 1% agarose A (Pharmacia) and 3% polyethyleneglycol-6000 in barbital-acetate buffer (8.93 g Na-barbital; 5.87 g Na-acetate.3H$_2$O; pH 8.2 with HCl) was prepared by heating in a microwave oven. The solution was cooled to 60° C. and 14 ml poured on a glass slide (8.3×9.4 cm). Using a mould (LKB), holes with a diameter of 4 mm were punched in the gel. After applying 10 μl of antiserum and purified enzyme solutions (a concentration of about 10 U/ml in phosphate-buffered saline pH 7.0), diffusion was allowed overnight at room temperature in a closed box with wetted tissue paper. The immune precipitates were scored directly or stained with a solution of 0.5% Coomassie Brilliant Blue R-250 (Biorad) in water-acetic acid-ethanol (4.5:1:4.5) after washing the gel several times with 0.9% NaCl. The gel was decoloured with water-acetic acid-ethanol (9:2:5).

The results (Table 1) showed positive reactions with the homologous guar enzyme and with the enzymes from fenugreek and lucerne. The guar enzyme produced by genetically engineered *S. cerevisiae* also showed a positive reaction. No reactions were observed with the enzymes from coffee beans, *A. niger, S. carlsbergensis* and *E. coli*.

4.4. Immunological Relationship Analysed by Western Blot Technique

The advantages of this technique are: sensitivity (enzyme solutions of 0.01 U/ml can be analysed) and the possibility to use crude preparations.

After addition of sample buffer (Edens et al., 1982) to the crude extracts, they were boiled for 5 minutes. Purified proteins were applied in gel sample buffer after heating for only 2 minutes. Proteins were separated by electrophoresis on 10% polyacrylamide gels according to Wyckoff et al. (1977).

Proteins were subsequently transferred from the gel onto nitrocellulose by electrophoretic transfer (ref. Burnette, 1979). The nitrocellulose was rinsed with incubation (I) buffer (150 mM NaCl, 5 mM EDTA, 50 mM Tris-HCl pH 7.0, 0.05% Triton X-100, 0.25% gelatin) and incubated in I-buffer with 0.1% BSA and antiserum raised by immunization of rabbits with alpha-galactosidase purified from guar. Incubation was at room temperature for 4 hours with agitation.

Unabsorbed antibodies were removed by washing with I-buffer (2 times) and phosphate-buffered saline pH 7.0 (PBS). Antibodies bound to antigen were detected by reaction with $^{125}$I Protein A (Amersham) for 1 hour. After washing with I-buffer (2 times) and PBS (3 times), the nitrocellulose was dried and exposed to X-ray film at $-70°$ C.

This technique was applied to alpha-galactosidase preparations from twelve different sources (see Table 1). The results showed positive reactions for all the alpha-galactosidase enzymes from plant species.

Also, all enzymes from micro-organisms genetically engineered with the guar alpha-galactosidase encoding genetic information gave a positive reaction. In contrast, the microbial enzyme from *A. niger, S. carlsbergensis* and *E. coli* showed no reaction with the antiserum raised against guar alpha-galactosidase.

These results confirm the results of the Ouchterlony assay with exception of the enzyme from coffee beans. One can conclude that it does have some relationship with the guar alpha-galactosidase which is much less than the enzymes from the closely related plant species.

Capability of Alpha-Galactosidase Enzymes To Decrease The Galactose Content Of Galactomannans Enzyme preparations (15-30 U) were dissolved in 1.5 ml of 100 mM sodium acetate buffer pH 4.5. This was added to 1 g of guar gum, vigorously mixed for at least 1 minute until the mixture had a fine "bread crumb" texture and incubated at 55° C.

To analyse the activity of the enzymes on galactomannan, samples were taken and analysed as follows:

A sample of about 150 mg "bread crumb" mix was taken and weighed. The enzyme was inactivated by placing in a boiling water bath for 10 minutes.

Subsequently 5 ml 10% sodium hydroxide was added and the sample dispersed using a small homogeniser. The solution was made up to 25 ml, shaken for 30 minutes, homogenised again and left for 15 minutes. After this treatment, the polysaccharide was dissolved completely and ready for determination of free galactose (using the enzymatic test kit from Boehringer) and total carbohydrate. An Anthrone assay (Morris, 1948) was used for the determination of total carbohydrate. The modified procedure (Loewus, 1952) is as follows.

A saturated solution of anthrone in ethyl acetate was prepared and left to stand for at least one hour. 25 µl of the assay solution was pipetted into a test tube and made up to 1 ml with distilled de-ionised water. (Water was used as the blank and 80 µg of galactose as the standard). 0.2 ml ethyl acetate saturated with anthrone was added, followed by 2.5 ml concentrated sulphuric acid.

It was vigorously mixed and allowed to cool. The adsorbance was read about 30 minutes later at 610 nm.

The results, summarized in Table 1 at the end of this specification, showed that all the plant enzymes were capable of decreasing the galactose content of galactomannans significantly (more than 25% of the galactose present released after 18 hours). Also the enzymes produced by microorganisms genetically engineered with the guar alpha-galactosidase genetic information had the same capability.

From these results it is evident that, next to the alpha-galactosidase enzyme from guar, other alpha-galactosidase enzymes are suited for modification of galactomannans. Although immunological relationship can give an indication, enzymes not related to the guar enzyme and still capable of modifying galactomannans cannot be excluded.

EXAMPLE 5

Production of the Guar Alpha-Galactosidase by Genetically Engineered *Kluyveromyces Marxianus* var. *Lactis*

Genetic Engineering of Vector pUR2405

Figure 12:
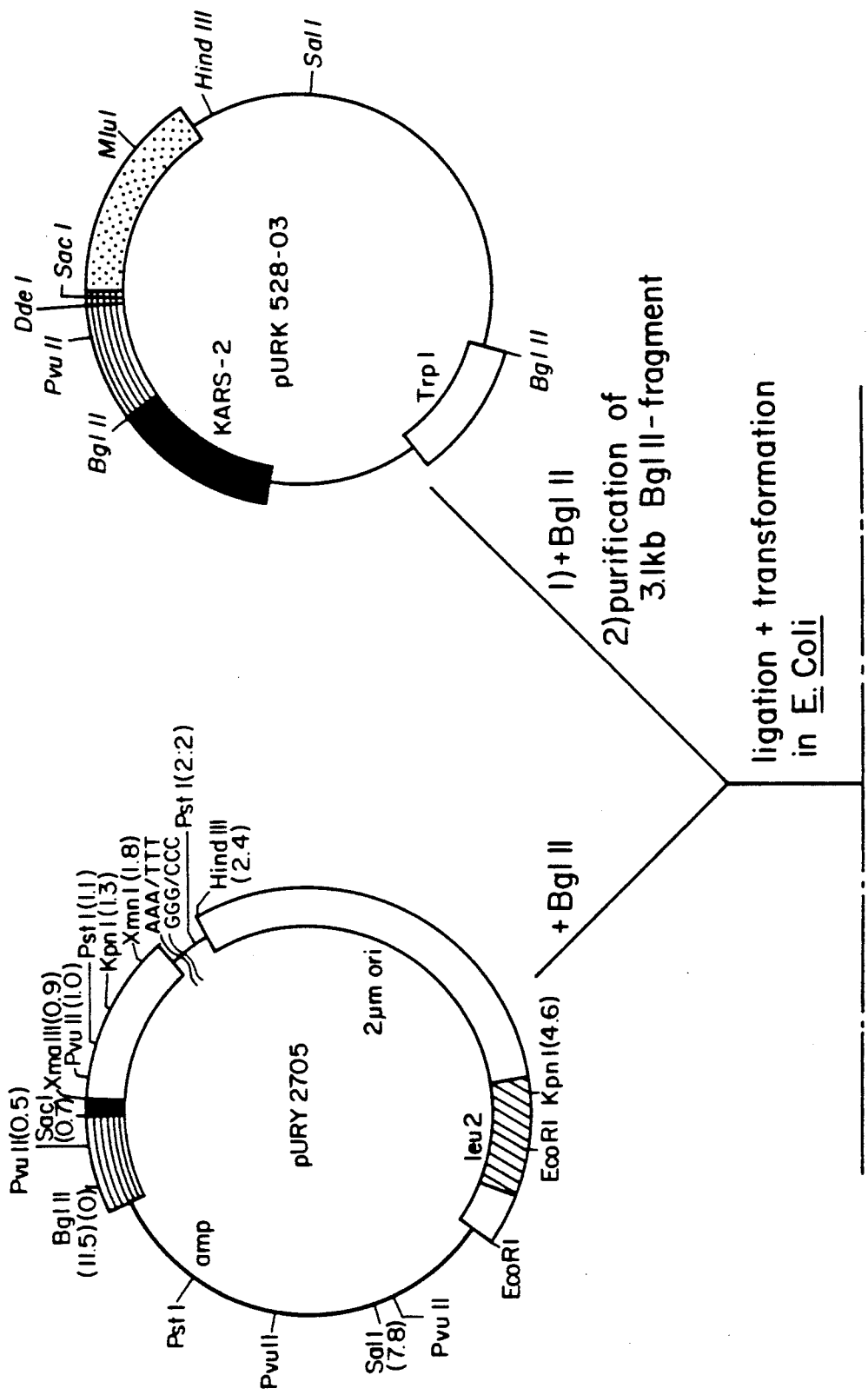
Figure 12:
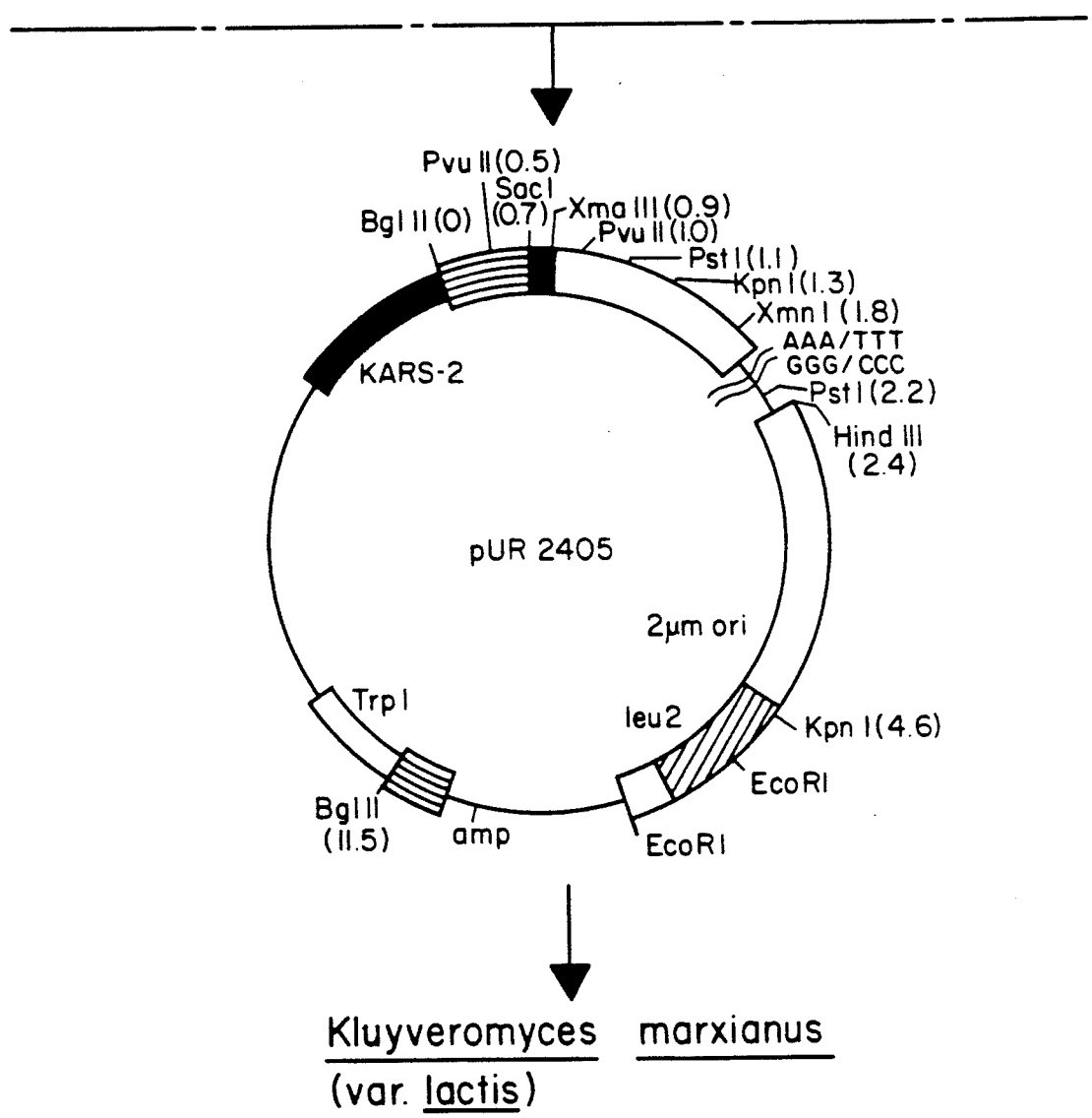
Figure 13:
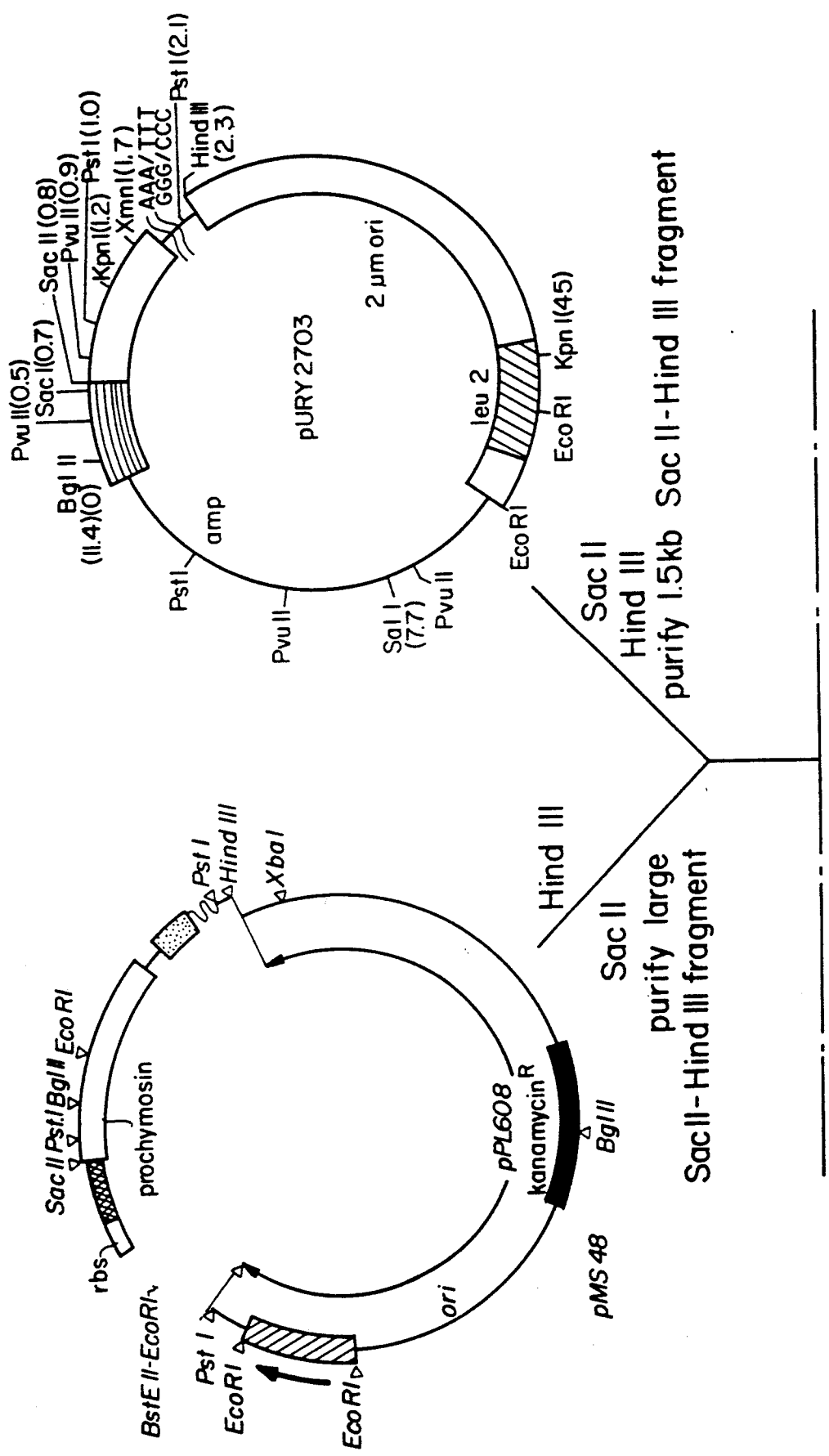
Figure 13:
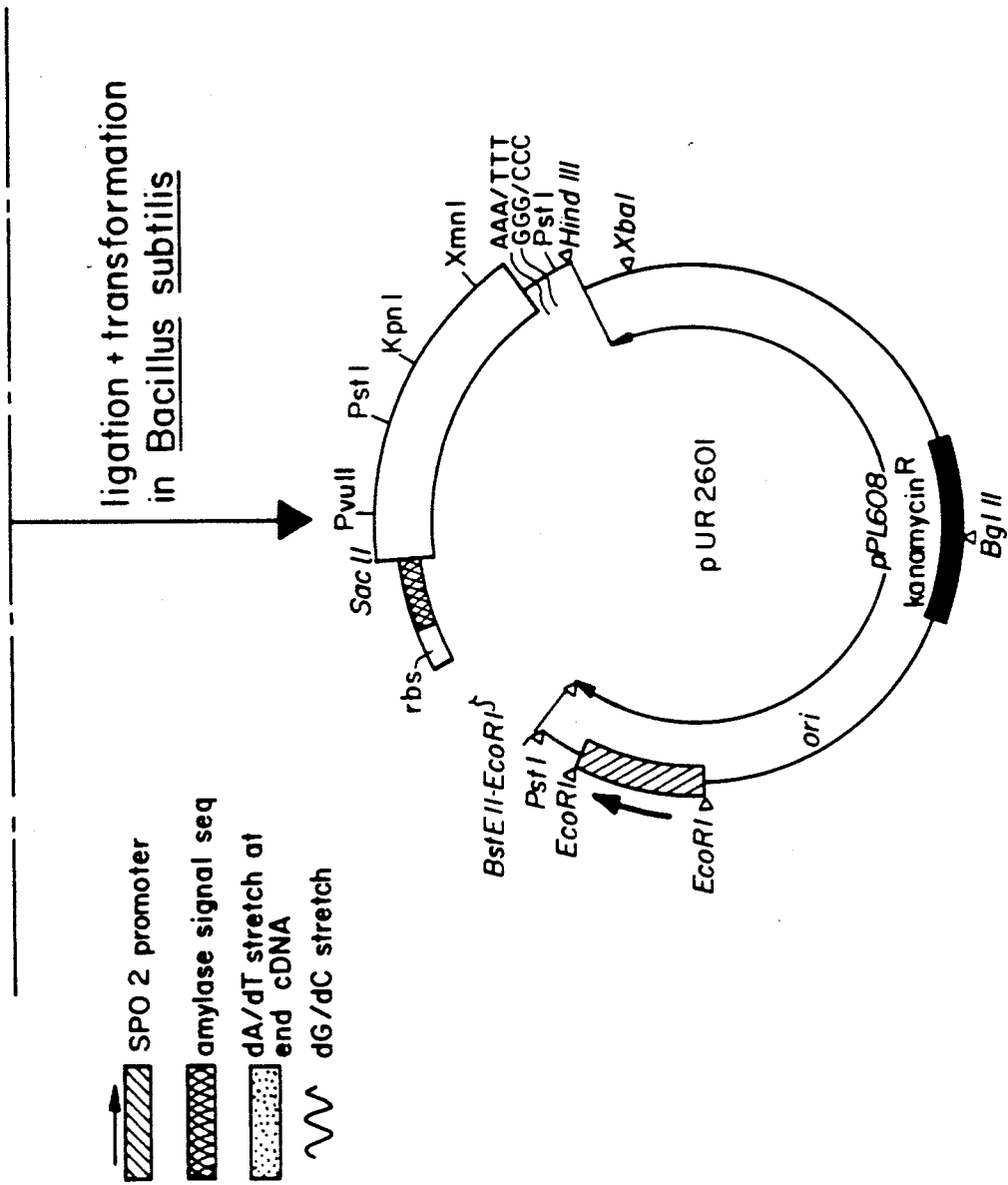

The strategy for the construction is outlined in FIG. 12.

The basis of this vector is the Kluyveromyces replication origin KARS2 and the selection marker trpl. The plasmid pURK 528-03 (Edens et al.; 1983) was digested with BglII (Amersham) and the 3.1 kb BglII fragment harbouring both these elements was isolated after electrophoresis on a 1% agarose gel followed by electroelution into a dialysis bag (Maniatis et al., 1982). This purified fragment was ligated with plasmid pURY2705 (FIG. 10) which was linearized with BglII. The ligated sample was used to transform *E. coli* strain JM 103 (described by Messing et al., 1981) with the CaCl$_2$ procedure and plated on L-broth supplemented with ampicilline (100 µg/ml) as described (Maniatis et al 1982). From the resulting colonies plasmid DNA was purified using the alkaline lysis method described by Birnboim and Doly (1979). After digestion with BglII those plasmids in which the 3.1 kb BglII fragment was inserted into the BglII site of pURY2705 were selected resulting in plasmid pUR2405 (FIG. 12).

Transformation and Analysis of *K. marxianus* var. *lactis* Cells with pUR2405

Yeast cells of strain *K. marxianus* var. *lactis* SD11 lac-4, trp-1 (Edens et al., 1983) were transformed with plasmid pUR2405 using the LiCl-method as described by Ito et al. (1983). The resulting trp+ transformants were analysed for presence of the guar alpha-galactosidase enzyme.

After growth on YMM, cells were harvested, resuspended in extraction buffer (10 mM Tris-HCl pH 8.0, 0.1 mM EDTA, 1 mM DTT) and disrupted by three freeze-thaw cycles. These crude cell extracts were assayed for active alpha-galactosidase enzyme with the artificial substrate pNPG and by an immunological assay (Western blot).

An appropriate dilution of crude cell extract in extraction buffer was incubated with 10 mM pNPG in 0.1 M sodium acetate pH 4.5 for 5 minutes at 37° C. The reaction was stopped by addition of 1 ml 2% sodium carbonate. The absorbance of the resulting mix was determined at 410 nm after removal of cells and cell debris by centrifugation for 5 minutes in an Eppendorf centrifuge. The extinction coefficient of p-nitrophenol at 410 nm is 18.4 cm$^2$/μmole. One unit of alpha-galactosidase is defined as the amount of enzyme which hydrolyses 1 μmole of substate in 1 minute at 37° C. at pH 4.5.

The cell-extract of cells with plasmid pUR2405 gave a positive signal in this assay in contrast to control preparations of yeast cells without the plasmid.

For the immunological assay we used a so-called Western blot analysis. After addition of sample buffer (Edens et al., 1982) to the crude cell extracts, they were boiled for 5 min.

Purified proteins were applied in gel sample buffer after heating for only 2 minutes. Proteins were separated by electrophoresis on 10% polyacrylamide gels according to Wyckoff et al. (1977).

Proteins were subsequently transferred from the gel onto nitrocellulose by electrophoretic transfer (ref. Burnette, 1979). The nitrocellulose was rinsed with incubation (I) buffer (150 mM NaCl, 5 mM EDTA, 50 mM Tris-HCl pH 7.0, 0.05% Triton X-100, 0.25% gelatin) and incubated in I-buffer with 0.1% BSA and antiserum raised by immunization of rabbits with alpha-galactosidase purified from guar.

Incubation was at room temperature for 4 h with agitation. Unabsorbed antibodies were removed by washing with I-buffer (2 times) and phosphate buffered saline pH 7.0 (PBS). Antibodies bound to antigen were detected by reaction with $^{125}$I Protein A (Amersham) for 1 h. After washing with I-buffer (2 times) and PBS (3 times) the nitrocellulose was dried and exposed to X-ray film at −70° C.

The result showe that in the Kluyveromyces cell extracts a protein was present having a molecular weight similar to that of the plant enzyme and also similar to that produced by the plasmid pURY2705 in *S. cerevisiae*.

EXAMPLE 6

Production of the Guar Alpha-Galactosidase by Genetically Engineered *Bacillus subtilis*

To illustrate that the alpha-galactosidase gene can be expressed not only in eukaryotic cells, but also in prokaryotic micro-organisms, a plasmid was constructed capable of producing the enzyme in *Bacillus subtilis*.

Genetic Engineering of Vector pUR2601

Plasmid pMS48 (Kok, J. et al., 1985; EP-A-0 157 441; pages 51-57) was used as a basis for a construction in which the mature guar alpha-galactosidase gene present in plasmid pURY2703 was fused to the alpha-amylase signal sequence while the gene encoding this fusion protein was under control of the SPO2 promoter (see FIG. 13). Plasmid pMS48 was digested with SacII and HindIII and the larger vector fragment containing the SPO2 promoter and the alpha-amylase signal sequence was purified. The 1.5 kb SacII-HindIII fragment of pURY2703 containing the alpha-galactosidase gene (see FIG. 9) was purified and ligated to the larger vector fragment of pMS48, hereby fusing exactly the alpha-amylase signal sequence with the mature alpha-galactosidase gene, yielding a plasmid called pUR2601. The ligation sample was used to transform *B. subtilis* strain DB104 described by Kawamura and Doi (1984), using the protoplast method (Kok, J. et al., 1985; page 52) using neomycine for selection.

Neomycine-resistant colonies were picked and plasmid DNA was purified according to Birnboim and Doly (1979), with the modification that the lysis step was performed at 37° C. for 30 minutes instead of at 4° C., and analysed by digestion with suited restriction enzymes. Transformants harbouring the correct plasmid pUR2601 were further anaysed for alpha-galactosidase production by both the pNPG-analysis and the Western blot procedure.

Analysis of the Production of Guar Alpha-Galactosidase by *B. subtilis*

It has been reported for Bacillus that heterologous proteins can be detected only in a specific growth phase of the cells (Grandi, G. et al., 1986). Therefore, an overnight culture was grown on L-broth with neomycine (20 μg/ml) diluted 1:50 and at several times the presence of alpha-galactosidase in the growth medium assayed with pNPG. The results (FIG. 14) showed a maximum of about 0.1 U/ml alpha-galactosidase enzyme present outside the cells in the growth medium after 7 hours of growth. Prolonged culturing lowered the enzyme concentration at least 30-fold, most likely owing to protease activity.

Production of the guar alpha-galactosidase by *B. subtilis* strain DB104 with plasmid pUR2601 was further studied in a 10 liter fermenter such that protease production is repressed by using both a suitable growth medium and a controlled growth.

A pre-culture of strain DB104 with pUR2601 was grown for 16 hours in 500 ml medium supplemented with neomycin (20 μg/ml) in a shake flask. The medium composition was as follows (g/l): NH$_4$Cl, 8: KH$_2$PO$_4$, 4; sucrose, 40; NaCl, 2; yeast extract (Difco) (sterilized separately), 10; MgSO$_4$.7 aq, 1; vitamin solution, 1; trace metal solution, 1.

The trace metal solution contained (g/l):

| | |
|---|---|
| CaCl$_2$.2 aq | 5.5 |
| FeSO$_4$.7 aq | 3.75 |
| MnSO$_4$.1 aq | 1.4 |
| ZnSO$_4$.7 aq | 2.2 |
| CuSO$_4$.5 aq | 0.4 |
| CoCl$_2$.6 aq | 0.45 |
| Na$_2$MoO$_4$.2 aq | 0.26 |
| H$_3$BO$_3$ | 0.4 |
| KI | 0.26 |
| EDTA | 45 |

The salts were dissolved while keeping the pH at 4.0. The vitamin solution contained (g/l):

| | |
|---|---|
| biotine | 0.05 |
| thiamine | 5.0 |
| mesoinosit | 4.7 |
| pyridoxine | 1.2 |
| D-pantothenic acid | 23.0 |

8 liters medium (without antibiotic) were sterilized at 120° C. for 20 minutes in the 10 liter fermenter.

The fermentation was started by inocculation with 500 ml pre-culture. The temperature was kept at 30°±0.1° C. The pH was controlled at 6.5 by addition of 12.5% NH$_4$OH. The dissolved oxygen tension was kept above 25% air saturation by controlling the air flow from 1.5 to 3.5 liters per minute. The stirrer speed of the 8-blade propeller was kept at 500 revolutions per minute.

The fermentation was followed by on-line respiration measurements (oxygen consumption and carbon dioxide evolution), by measuring the optical density at 610 nm. The alpha-galactosidase activity was measured every 30 minutes.

The alpha-galactosidase activity is closely correlated with the biomass formation. The maximal alpha-galactosidase activity of 1760 U/liter was obtained after 12 hours, which corresponds with the end of the exponential growth phase. The biomass concentration was 10.2 g. After reaching this maximal activity, the culture was cooled to +8° C. and the cells were centrifuged.

So, by applying special growth conditions, Bacillus can produce and excrete high amounts of guar alpha-galactosidase enzyme.

For the immunological assay we used a so-called Western blot analysis. After addition of sample buffer (Edens et al., 1982) to the culture mediu, the sample was boiled for 5 min.

Purified proteins were applied in gel sample buffer after heating for only 2 minutes. Proteins were separated by electrophoresis on 10% polyacrylamide gels according to Wyckoff et al. (1977).

Proteins were subsequently transferred from the gel onto nitrocellulose by electrophoretic transfer (ref. Burnette, 1979). The nitrocellulose was rinsed with incubation (I) buffer (150 mM Nacl, 5 mM EDTA, 50 mM Tris.HCl pH 7.0, 0.05% Triton X-100, 0,25% gelatin) and incubated in I-buffer with 0.1% BSA and antiserum raised by immunization of rabbits with alpha-galactosidase purified from guar.

Incubation was at room temperature for 4 h with agitation. Unabsorbed antibodies were removed by washing with I-buffer (2 times) and phosphate buffered saline pH 7.0 (PB S). Antibodies bound to antigen were detected by reaction with $^{125}$I Protein A (Amersham) for 1 h. After washing with I-buffer (2 times) and PB S (3 times) the nitrocellulose was dried and exposed to X-ray film at −70° C.

Western bolt analysis (FIG. 15) showed a specific reaction of the guar alpha-galactosidase antiserum demonstrating the presence of the guar alpha-galactosidase enzyme. However, the enzyme present in the medium (lane 5) had a molecular weight slightly lower than the enzyme from plant origin (lane 1), but identical with the enzyme produced by yeast cells with plasmid pURY2703 (see Example 2, FIG. 11). Cell extracts showed (lane 3) a dominant band with the same molecular weight as the enzyme in the medium. Further bands with a lower molecular weight are visible, most likely due to proteolysis. Also a band with a slightly higher molecular weight was observed. This is most likely a form from which the singal sequence has not been processed.

Isolation and Purification of Alpha-Galactosidase for N-terminal Sequence Analysis After removal of the cells from the fermentation broth by microfiltration (0.22 μm), lower molecular weight substances were removed by desalting using a PD-10 column (Pharmacia) equilibrated with 0.03 M Tris.HCl pH 8.0. Alpha-galactosidase was further isolated by anion-exchange chromatography, using a MONO-Q column (HR 5/5, Pharmacia). Elution was achieved by a NaCl gradient (0–1 M) in 0.03 M Tris.HCl pH 8.0. Detection was at 214/280 nm using the Pharmacia FPLC system. Fractions containing alpha-galactosidase activity (eluting at about 0.3 M NaCl) were pooled and desalted (PD-10 column, eluent 0.01 M Na-acetate pH 4.5). Final purification was done by reversed phase chromatography using a wide pore C-4 column (Bakerbond, 4.6*250 mm) with gradient elution: buffer A 0.1% TFA (v/v), buffer B 0.1% TFA+60% $CH_3CN$ (v/v) in 25 minutes, detection at 214/254 nm using a Waters HPLC system. The alpha-galactosidase peak (eluting at 55% $CH_3CN$) was concentrated in a Speed VAC Concentrator (SAVANT) and used for the N-terminal sequence analysis. This was carried out in an Applied Biosystems gas phase sequencer (model 470 A) using the on-line PTH-analyser (120 A).

The results showed that the first 7 $NH_2$ terminal residues of the *B. subtilis*-produced enzyme were identical with the sequence of the enzyme purified from guar seed (see Example 1.2.4; FIG. 3B).

So we conclude that the guar alpha-galactosidase enzyme is secreted and correctly processed. This enzyme is not glycosylated because prokaryotes lack the capabilities therefor.

EXAMPLE 7

Reduction of the Galactose Content of Galactomannans by the Alpha-Galactosidase Enzyme Produced by Genetically Engineered *B. subtilis*

The guar alpha-galactosidase enzyme produced by cells of strain DB 104 harbouring plasmid pUR2601 (see Example 6) was tested for the activity to decrease the galactose content of galactomannans.

Therefore a preparation was purified from the fermentation broth using a MONO-Q column (see Example 6).

Fractions containing alpha-galactosidase activity (eluting at about 0.3 M NaCl) were pooled and desalted (PD-10 column, eluent 0.01 M Na-acetate pH 4.5).

The enzyme preparations were further concentrated about 10-fold by vacuum drying.

Used as a control was alpha-galactosidase enzyme purified from guar seeds as described by McCleary (1983).

The capability of these alpha-gelactosidase enzymes to descrease the galactose content of guar gum was analysed as follows:

Enzyme preparations (25 U for the guar enzyme and 15 U for the *B. subtilis*-produced enzyme) were dissolved in 1.5 ml of 100 mM sodium acetate buffer pH 4.5. This was added to 1 g of guar gum, vigorously mixed for at least 1 minute until the mixture had a fine "bread crumb" texture and incubated at 55° C.

To analyse the activity of the enzymes on galactomannan, samples were taken and analysed as follows:

A sample of about 150 mg "bread crumb" mix was taken and weighed. The enzyme was inactivated by placing in a boiling water bath for 10 minutes.

Subsequently 5 ml 10% sodium hydroxide was added and the sample dispersed using a small homogeniser. The solution was made up with water to 25 ml, shaken for 30 minutes, homogenised again and left for 15 minutes. After this treatment, the polysaccharide was dissolved completely and ready for dtermination of free galactose and total carbohydrate. Free galactose was determined by adding the assay solution (0.1 ml+0.1 ml $H_2O$) to 0.2 M Tris.HCl pH 8.6 (2.7 ml) followed by 1% w/v NAD solution (0.1 ml) and 0.25 U beta-galactose dehydrogenase (Sigma) in 0.2 M Tris.HCl pH 8.6 (0.05 ml). A solution made up as above with the omission of beta-galactose dehydrogenase was used as the blank and 80 μg galactose was used as the standard. Solutions were incubated for 1 hour at 37° C. and the absorbance measured at 340 nm immediately after incubation. An Anthrone assay (Morris, 1948) was used for the determination of total carbohydrate. The modified procedure (Loewus, 1952) is as follows.

A saturated solution of anthrone in ethyl acetate was prepared and left to stand for at least one hour. 25 μl of the assay solution was pipetted into a test tube and made up to 1 ml with distilled de-ionised water. (Water was used as the blank and 80 μg of galactose as the standard). 0.2 ml ethyl acetate saturated with anthrone was added, followed by 2.5 ml concentrated sulphuric acid. It was vigorously mixed and allowed to cool. The absorbance was read about 30 minutes later at 610 nm.

From these results the percentage of galactose present on the polysaccharide was calculated.

| Enzyme | % galactose on galactomannan after | | | | |
|---|---|---|---|---|---|
| | 0 hr | 2 hr | 3 hr | 6 hr | 23 hr |
| B. subtilis enzyme (15 U) | 38 | | 31 | 28 | 25 |
| guar (25 U) | 38 | 31 | | 26 | 18 |

These results demonstrate that the enzyme from guar and the enzyme produced by genetically engineered B. subtilis cells are capable of decreasing the galactose content of guar gum.

A further surprising conclusion is that the absence of glycosylation has no adverse effect on the behaviour of the enzyme on galactomannans.

EXAMPLE 8

Production of the Guar Alpha-Galactosidase by Genetically Engineered *Hansenula polymorpha*

Genetic Engineering of Vector pUR3510

The strategy for the construction is outlined in FIG. 16.

The basis of this vector is the yeast YEp13 vector (Broach et al., 1979) and the selection marker leu 2. In this vector was engineered a fusion between the MOX promoter mentioned above (Ledeboer et al., 1984), the invertase signal sequence from *S. cerevisiae* (Taussig and Carlson, 1983), the mature alpha-galactosidase gene (FIG. 6) and the MOX terminator (Ledeboer et al., 1984).

Figure 2:
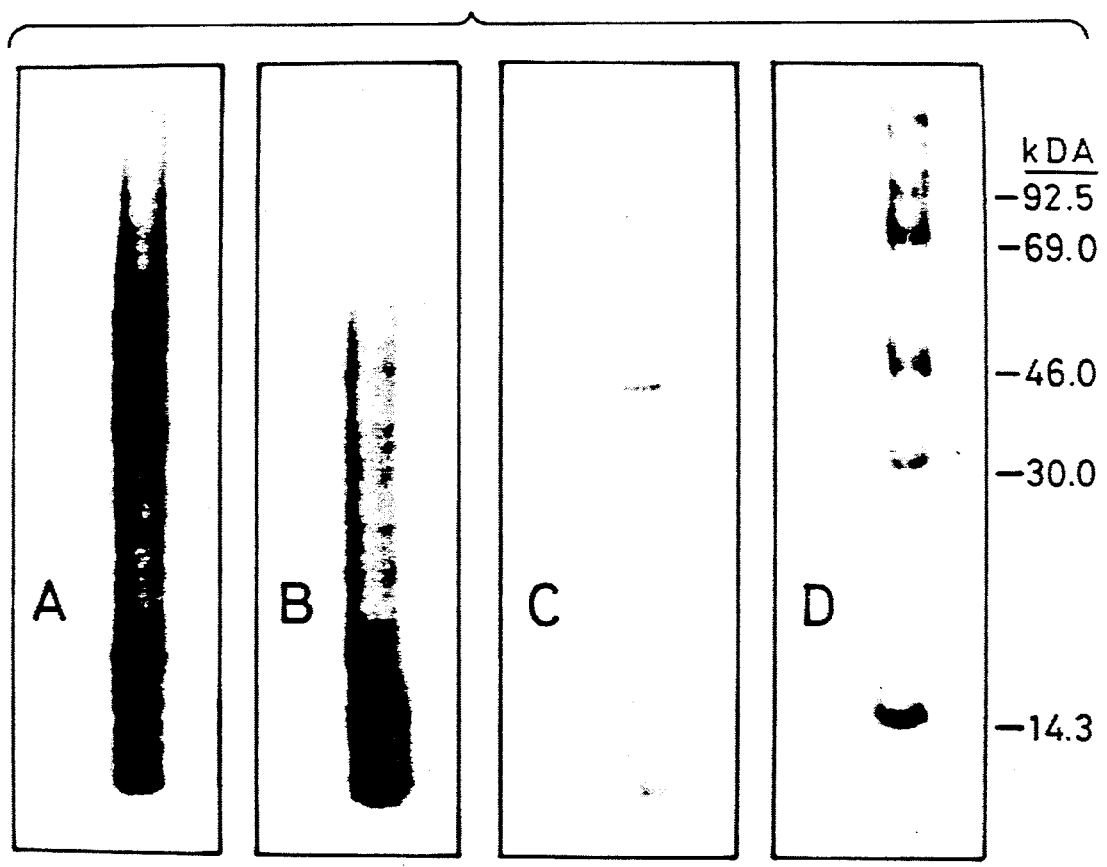
Figure 4:
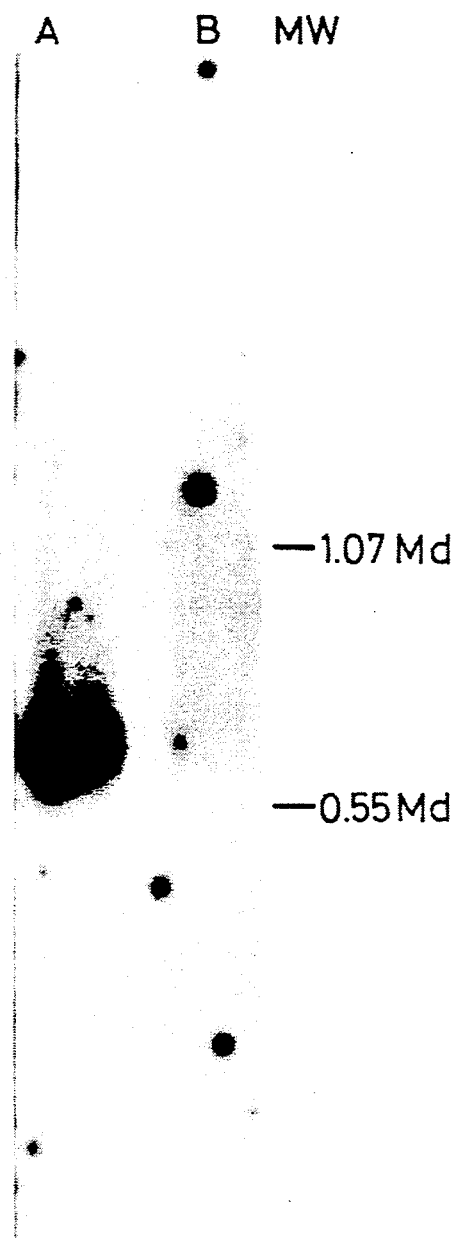

The various steps resulting in this plasmid pUR3510 will be described in detail below and are as follows:
a. elimination of the non-translated sequence after the translation stop (yielding pUR2303; FIG. 16-1);
b. fusion of MOX promoter with the invertase signal sequence and mature alpha-galactosidase (yielding pUR3501; FIG. 16-2);
c. addition of the MOX terminator (yielding pUR3505; FIG. 16-3);
d. introduction in YEp13 vector (yielding pUR3510; FIG. 16-4).

Construction of pUR2303 (FIG. 16-1)

To eliminate the untranslated part of the mRNA after the translation stop at mucleotide 1400 (FIG. 6), as well as the poly A/T and G/C tails, the part of the gene frm the XmnI site at nucleotides 1223-1233 (FIG. 6) up to the translation stop was replaced by an in vitro synthesized fragment. This fragment was composed of 13 oligonucleotides encoding exactly the sequence of the alpha-galactosidase gene including the double translation stop. For further cloning convenience, a SalI and HindIII site were introduced immediately behind the translation stop.

The procedure was as follows. After purification of the oligonucleotides, all except 1 and 13 were phosphorylated. After annealing and ligation, the fragment of the correct size was purified after agarose gel electrophoresis and ligated with vector pEMBL9 which had been digested with BamHI and HindIII. E. coli cells were transformed and plasmid DNA purified. Plasmids with the expected BamHT-HindIII fragment of 0.18 Kb were analysed by nucleotide sequencing. From the clone with the correct sequence, the XmnI-HindIII fragment was purified and ligated together with the BamHI-XmnI fragment of 1.2 kb from plasmid pUR 2302 (FIG. 7) encoding te pre-pro-alpha-galactosidase gene and the vector pBR322 digested with BamHI and HindIII in a molar ratio of about 4:2:1.

E. coli cells were transformed with the ligation mix and plasmid DNA purified from ampicillin-resistant, tetracyclin-sensitive transformants. The purified plasmid DNA was analysed with restriction enzymes. This resulted in plasmid pUR2303 encoding the complete guar pre-pro-alpha-galactosidase gene from which the non-translated sequences after the translation stop had been removed.

Construction of pUR3501 (FIG. 16-2)

In order to realise an exact fusion between the MOX promoter and the invertase signal sequence—mature alpha-galactosidase, a synthetic dsDNA fragment composed of 6 oligonucleotides was used. This synthetic fragment encodes the last part of the MOX promoter from the HgiAI site (see Ledeborer et al., 1984), the invertase signal sequence from *S. cerevisiae* (Taussig and Carlson, 1983) and the first 10 amino acids from the mature alpha-galactosidase up to the NcoI site (FIG. 6). For the coding region, the optimal codon usage for *H. polymorpha* (Ledeboer et al., 1985) was chosen.

From the six cligonucleotides, 1, 2, 3 and 4 were phosphorylated and subsequently annealed and ligated after addition of oligonucleotides 0 and 5. The next step was the ligation of the synthetic fragment with the SalI-HgiAI MOX promopter fragment from pUR3102 (Ledeboer et al., 1984, FIG. 12A) and the M13 vector (digested with SalI and EcoRI and subsequently dephosphorylated. E. coli cells were transformed with this ligation mix and white plaques picked. Both the single-stranded phage DNA and the double-stranded form were purified. From a clone with the correct restriction enzyme pattern and the exact nucleotide sequence of the synthetic fragment the SalI-NcoI fragment was purified for further cloning.

This SalI-NcoI fragment was ligated with the NcoI-SalI fragment from pUR2303 encoding the mature alpha-galactosidase (FIG. 16-1) and the vector pEMBL9 digested with SalI and dephosphorylated. E. coli cells were transformed with the ligation mix, and analysis for plasmids with the correct restriction enzyme pattern resulted in plasmid pUR3501.

Construction of pUR3505 (FIG. 16-3)

The 2.6 Kb SalI fragment of plasmid pUR3501 was purified and ligated into plasmid pUR3104 which contains the MOX terminator fragment (Ledeboer et al., 1984, FIG. 14A). Plasmids from the resulting transformants were analysed with restriction enzymes for the proper orientation of the fragment (MOX promoter—invertase signal sequence—alpha-galactosidase—MOX terminator), resulting in plasmid pUR3505. This plasmid is already suited for (site-directed) integration in the *H. polymorpha* genome. One can anticipate for the transformants to acquire the ability to grow on melibiose as a carbon source owing to the presence of an active alpha-galactosidase enzyme. However, we firstly chose to use the YEp13 vector with a leu-2 auxotrophic selection marker and capable of autonomic replication in *H. polymorpha* (Gleeson et al., 1986).

Construction of Plasmid pUR3510 (FIG. 16-4)

The complete promoter—gene—terminator sequence was purified from plasmid pUR3505 as a 5.2 kb HindIII-EcoRI fragment. To clone this fragment in the unique BamHI site of YEp13 situated in the tet-gene, we used BamHI-HindIII and BamHI-EcoRI adapters. After ligation of the phosphorylated adapters, the mixture was digested with BamHI and the 5.2 Kb fragment purified. Finally, the BamHI fragment was ligated with YEp13 (digested with BamHI and dephosphorylated). *E. coli* cells were transformed with ligation mix and plasmid DNA purified from ampicillin-resistant and tetracyclin-sensitive clones. From these the plasmid with the correct restriction enzyme pattern was selected, pUR3510.

Transformation and Analysis of *H. polymorpha* with pUR3510

*Hansenula polymorpha* strain L1 (leu 1-1) was transformed using the procedure described by Gleeson et al. (1986) with LiCl and circular plasmid DNA. Transformants were selected for growth on MM with glucose as carbon source without leucine. The resultant leu+ transformants were analysed for the presence of the guar alpha-galactosidase enzyme.

After growth on YMM agar plates with glycerol as the carbon source, cells were harvested, resuspended in extraction buffer (10 mM Tris-HCl pH 8.0, 0.1 mM EDTA, 1 mM DTT) and disrupted by three freeze-thaw cycles. These crude cell extracts were assayed for active alpha-galactosidase enzyme with the artificial substrate pNPG and by an immunological assay (Western blot).

An appropriate dilution of crude cell extract in extraction buffer was incubated with 10 mM pNPG in 0.1M sodium acetate pH 4.5 for 5 minutes at 37° C. The reaction was stopped by addition of 1 ml 2% sodium carbonate. The absorbance of the resulting mix was determined at 410 nm after removal of cells and cell debris by centrifugation for 5 minutes in an Eppendorf centrifuge. The extinction coefficient of p-nitrophenol at 410 nm is 18.4 cm$^2$/μmole. One unit of alpha-galactosidase is defined as the amount of enzyme which hydrolyses 1μmole of substrate in 1 minute at 37° C. at pH 4.5.

The cell-extract of cells with plasmid pUR3510 gave a positive signal in this assay in contrast to control preparations of yeast cells without the plasmid.

For the immunological assay we used a so-called Western blot analysis. After addition of sample buffer (Edens et al., 1982) to the crude cell extracts, they were boiled for 5 min.

Purified proteins were applied in gel sample buffer after heating for only 2 minutes. Proteins were separated by electrophoresis on 10% polyacrylamide gels according to Wycoff et al. (1977).

Proteins were subsequently transferred from the gel onto nitrocellulose by electrophoretic transfer (ref. Burnette, 1979). The nitrocellulose was rinsed with incubation (I) buffer (150 mM NaCl, 5 mM EDTA, 50 mM Tris-HCl pH 7.0, 0.05% Triton X-100, 0.25% gelatin) and incubated in I-buffer with 0.1% BSA and antiserum raised by immunization of rabbits with alpha-galactosidase purified from guar.

Incubation was at room temperature for 4 h with agitation. Unabsorbed antibodies were removed by washing with I-buffer (2 times) and phosphate buffered saline pH 7.0 (PB S). Antibodies bound to antigen were detected by reaction with $^{125}$I Protein A (Amersham) for 1 h. After washing with I-buffer (2 times) and PB S (3 times) the nitrocellulose was dried and exposed to X-ray film at −70° C.

The result (FIG. 17) showed that in the Hansenula cell extracts with the plasmid (lane C) a protein was present having a molecular weight identical with that of the plant enzyme (lane B) and also identical with that produced by the plasmid pURY2705 in *S. cerevisiae*. Hansenula cells without the plasmid showed no protein (lane A).

EXAMPLE 9

Production of the Guar Alpha-Galactosidase by Genetically Engineered *S. cerevisiae* Using the GAL7 Promoter As a further illustration of the production of guar alpha-galactosidase by mirco-organisms, we constructed vectors for inducible expression of the enzyme in *S. cerevisiae* using the GAL7 promoter. The nucleotide sequence of this promoter has been described (Nogi and Fukasawa, 1983).

This promoter sequence gives rise to the production of the GAL7 encoded enzyme under induced conditions: growth on medium with galactose as the sole carbon source (Hopper and Rowe, 1978). Furthermore, the use of this promoter for the induced expression of heterologous genes (e.g. the lacZ gene known from *E. coli*) has also been described (Tajima et al., 1985; Yarger et al., 1985). Therefore we analysed expression of the hybrid gene invertase signal sequence:: mature alpha-galactosidase using the GAL7 promoter.

Genetic Engineering of Vectors pUR2706 and pUR2730

The basis for these vectors is the shuttle vector pUR2705 (see Example 2; FIG. 10) which contains the GAPDH promoter—invertase signal sequence:: mature alpha-galactosidase. From this vector the GAPDH promoter was almost completely removed and replaced by either a cloned 271 bp GAL7 promoter fragment (Tajima et al., 1985) obtained from Dr T. Fukasawa (Laboratory of Molecular Genetics, Keio University School of Medicine, Tokyo, Japan), resulting in vector pUR2706 or by an in vitro synthesized DNA promoter fragment resulting in pUR2730.

Plasmid pUR2706 was constructed as follows (see FIG. 18-1): At first the SacI site in the GAPDH promoter in vector pUR2705 was converted into a BamHI site. Therefore vector pURY2705 was digested with SacI and incubated with S1 exonuclease to create blunt ends to which subsequently a BamHI linker (5'CGGATCCG) was ligated. The ligation mixture was used to transform *E. coli* cells.

Plasmid DNA was isolated from the resulting transformants and analysed with restriction enzymes. A plasmid lacking the SacI site but having a BamHI site was selected (pURY2705'). Nucleotide sequence analysis showed that not only the SacI site was removed but also a number of nucleotides surrounding the SacI site. However, the translation start "ATG" of the invertase signal sequence was not affected. The following sequence was the result:

5'---ccttgaacttcggatccgATGATGCTT---3'

(the invertase signal sequence is given in capitals, the GAPDH promoter in lower case with the BamHI linker underlined).

This plasmid pURY2705' was digested with BglII and BamHI to remove the GAPDH promoter nearly completely, and the large vector fragment was purified after agarose gel electrophoresis. The GAL7 promoter is present on a plasmid as a 271 bp BamHI-BglII fragment (Tajima et al., 1985). This fragment was also purified after digestion and agarose gel electrophoresis. The two purified fragments were ligated and the ligation mix used to transform E. coli cells.

As BamHI and BglII produce identical sticky ends, the 271 bp promoter fragment can be ligated in two orientations. However, in case a "BamHI stickey end" is ligated to a "BglII sticky end", the result in a sequence which is recognized neither by BamHI nor by BglII. So the presence or absence of the BamHI and BglII sites gives direct information on the orientation of the promoter.

Therefore, plasmid DNA was purified from the transformants and analysed with these restriction enzymes. A plasmid with the promoter fragment in the right orientation, so lacking the BglII and BamHI sites, was selected (pURY2706). This resulted in the following nucleotide sequence of the fusion of the GAL7 promoter (lower case letters), BglII-BamHI linker (underlined) and invertase signal sequence (capitals):

gaatattccccagatccgATGATGCTT.

Plasmid pUR2730 was constructed as follows (see FIG. 18-2): At the first the GAL7 promoter sequence was synthesized as a ds DNA sequence consisting of 16 oligonucleotides which were combined and further handled as described for another group of oligonucleotides in Example 2. The first 5 were cloned as an EcoRI-BamHI fragment in pEMBL9 and the last 11 as a BamHI-HindIII fragment in pEMBL9. Plasmid DNA was purified from the transformants and analysed with restriction enzymes. Plasmids having an insert with the expected size were sequenced and clones with the correct nucleotide sequence were used for the further procedure.

In order to remove the GAPDH promoter, plasmid pUR2705 was digested with BglII, dephosphorylated, subsequently digested with SacI and the 10.7 kb vector fragment purified after gel electrophoresis. The two fragments encoding the GAL7 promoter were purified after digestion of the two pEMBL clones described above by digestion with BamHI, dephosphorylation, digestion with BglII and digestion with BamHI and SacI, respectively.

The vector fragment was ligated with the two GAL7 promoter fragments and the ligation mix was used to transform E. coli cells. Plasmid DNA was purified from the transformants and analysed with restriction enzymes. A plasmid with the proper restriction enzyme pattern was selected resulting in plasmid pUR2730.

Analysis of the Production of Guar Alpha-Galactosidase by Saccharomyces using the GAL7 Promoter Yeast cells of Saccharomyces strain SU10 (alpha, leu2, ura3, his3, cir+; deposited at the Centraalbureau voor Schimmelcultures, P.O. Box 273, 3740 AG Baarn, The Netherlands, under number CBS 323.87) were transformed with plasmid pURY2706 by the spheroplast method (Beggs, 1978).

The resulting leu+ transformed yeast cells were analysed for the presence of alpha-galactosidase enzyme. They were grown on YMM supplemented with uracil and histidine. Subsequently, the yeast cells were transferred to 10×larger volume of YPG medium and grown to the stationary phase. Cells were separated from the fermentation broth either by centrifugation or filtration (0.22 μm, Millipore). Both the fermentation broth and a crude cell extract were analysed for the presence of alpha-galactosidase as described in Example 2.

The results showed that about 5 units were present in 1 ml fermentation broth, while less than 10% of this concentration was present in the crude cell extract. So the alpha-galactosidase enzyme is secreted at rather high levels.

For a further detailed analysis of the enzyme produced, the alpha-galactosidase was purified as follows:

Yeast cells of strain SU10 harbouring plasmid pUR2706 were cultured as described above. After removal of the cells from the fermentation broth by microfiltration (0.22 μm), lower molecular weight substances were removed by desalting, using a PD-10 column (Pharmacia) equilibrated with 0.03M TRIS-HCl pH 8.0. Alpha-galactosidase was further isolated by anion-exchange chromatography, using a MONO-Q column (HR 5/5, Pharmacia). Elution was achieved by a NaCl gradient (0–1M) in 0.03M TRIS-HCl pH 8.0. Detection was at 214/280 nm using the Pharmacia FPLC system. Fractions containing alpha-galactosidase activity (eluting at about 0.3M NaCl) were pooled and deslated (PD-10 column, eluent 0.01M Na-acetate pH 4.5).

This preparation was used as a purified preparation for reduction of the galactose content of guar gum (see Example 10). Final purification for N-terminal sequence analysis was done by reversed phase chromatography using a wide pore C-4 column (Bakerbond, 4.6 * 250 mm) with gradient elution: buffer A 0.1% TFA (v/v), buffer B 0.1% TFA+60% CH$_3$CN (v/v) in 25 minutes, detection at 214/254 nm using a Waters HPLC system. The alpha-galactosidase peak (eluting at 55% CH$_3$CN) was concentrated in a Speed Vac Concentrator (SAVANT) and used for the N-terminal sequence analysis. This was carried out in an Applied Biosystems gas phase sequencer (model 470 A) using the on-line PTH-analyser (120 A).

The result showed that the 12 residues that were sequenced from the NH$_2$ terminus were exactly identical with the NH$_2$ terminal amino acid sequence of the guar alpha-galactosidase. The invertase signal sequence has been processed correctly, resulting in exactly the amino acid sequence of guar alpha-galactosidase.

EXAMPLE 10

Reduction of the Galactose Content of Galactomannans by the Alpha-Galactosidase Enzyme Produced by Genetically Engineered *S. cerevisiae* Using the GAL7 Promoter The guar alpha-galactosidase enzyme produced by yeast cells of strain SU10 harbouring plasmid pUR2706 (see Example 9) was tested for the activity to decrease the galactose content of galactomannans.

Therefore two different preparations were used. One preparation was purified from the fermentation broth using a MONO-Q column (see Example 9).

Fractions containing alpha-galactosidase activity (eluting at about 0.3M NaCl) were pooled and desalted (PD-10 column, eluent 0.01M Na-acetate pH 4.5).

The enzyme preparations were further concentrated about 10-fold by vacuum drying.

The other preparation was a crude concentrate obtained by a ten-fold concentration of the cleared fermentation broth using an Amicon concentrator retaining molecules larger than 10,000 Dalton.

Used as a control was alpha-galactosidase enzyme purified from guar seeds as described by McCleary (1983).

The capability of these alpha-galactosidase enzymes to decrease the galactose content of guar gum was analysed as follows:

Enzyme preparations (25 U) were dissolved in 1.5 ml of 100 mM sodium acetate buffer pH 4.5. This was added to 1 g of guar gum, vigorously mixed for at least 1 minute until the mixture had a fine "bread crumb" texture and incubated at 55° C.

To analyse the activity of the enzymes on galactomannan, samples were taken and analysed as follows:

A sample of about 150 mg "bread crumb" mix was taken and weighed. The enzyme was inactivated by placing in a boiling water bath for 10 minutes.

Subsequently 5 ml 10% sodium hydroxide was added and the sample dispersed using a small homogeniser. The solution was made up with water to 25 ml, shaken for 30 minutes, homogenised again and left for 15 minutes. After this treatment, the polysaccharide was dissolved completely and ready for determination of free galactose (see Example 7) and total carbohydrate. An Anthrone assay (Morris, 1948) was used for the determination of total carbohydrate. The modified procedure (Loewus, 1952) is as follows.

A saturated solution of anthrone in ethyl acetate was prepared and left to stand for at least one hour. 25 /µl of the assay solution was pipetted into a test tube and made up to 1 ml with distilled de-ionised water. (Water was used as the blank and 80 /µg of galactose as the standard). 0.2 ml ethyl acetate saturated with anthrone was added, followed by 2.5 ml concentrated sulphuric acid. It was vigorously mixed and allowed to cool. The absorbance was read about 30 minutes later at 610 nm.

From these results the percentage of galactose present on the polysaccharide was calculated.

| Enzyme | % galactose on galactomannan after | | | |
|---|---|---|---|---|
| | 0 hr | 2 hr | 6 hr | 23 hr |
| yeast crude concentrate | 38 | 30 | 28 | 16 |
| yeast purified | 38 | 31 | 26 | 18 |
| quar | 38 | 30 | 27 | 17 |

These results demonstrate that the enzyme from guar and the enzyme produced by genetically engineered yeast cells are indistinguishable in their capacity to decrease the galactose content of guar gum.

EXAMPLE 11

Production of the Guar Alpha-Galactosidase by Genetically Engineered Plants: Production by *Nicottiana Tabacum*

Next to production of the guar enzyme by genetically engineered micro-organisms, the production by plant cells can also offer economically interesting possibilities. However, next to the obvious requirement of the absence of beta-mannanase, the plants must be manipulatable by genetic engineering methods. The present example is focused on *N. tabacum* as an example, because this plant species has been widely used in genetic engineering experiments. As techniques come available for other plant species, production of the guar alpha-galactosidase can be easily transferred to other species.

To illustrate the production of guar alpha-galactosidase by plants, we constructed a vector therefor and transferred the vector into *Nicotiana tabacum*.

Construction of Plant Expression Vector with Guar Alpha-Galactosidase (pUR8001)

We decided to introduce the complete alpha-galactosidase gene including the sequence encoding the pre-pro-part preceeding the mature enzyme (see FIG. 6). Furthermore, the non-translated DNA sequence after the translation stop including the A/T and G/C tails were removed. Finally, the complete gene was flanked by BamHI sites to clone it in the plant expression vector between the cauliflower mosaic viru 35s promoter and the nopaline syntheses termination sequence. These genetic engineering steps are described in detail below.

Construction of pUR2303 (FIG. 16-1)

To eliminate the untranslated part of the mRNA after the translation stop at nucleotide 1400 (FIG. 6), as well as the poly A/T and G/C tails, the part of the gene from the XmnI site at nucleotides 1223-1233 (FIG. 6) up to the translation stop was replaced by an in vitro synthesized fragment. This fragment was composed of 13 oligonucleotides encoding exactly the sequence of the alpha-galactosidase gene including the double translation stop. For further cloning convenience, a SalI and HindIII site were introduced immediately behind the translation stop.

The procedure was as follows. After purification of the oligonucleotides, all except 1 and 13 were phosphorylated. After annealing and ligation, the fragment of the correct size was purified after agarose gel electrophoresis and ligated with vector pEMBL9 which had been digested with BamHI and HindIII. *E. coli* cells from strain JM103 were transformed and plasmid DNA purified. Plasmids with the expected BamHI-HindIII fragment of 0.18 Kb were analysed by nucleotide sequencing. From the clone with the correct sequence, the XmnI-HindIII fragment was purified and ligated together with the BamHI-XmnI fragment of 1.2 Kb from plasmid pUR 2302 (FIG. 7) encoding the pre-pro-alpha-galactosidase gene and the vector p8R322 digested with BamHI and HindIII in a molar ratio of about 4:2:1.

*E. coli* cells were transformed with the ligation mix and plasmid DNA purified from ampicillin-resistant, tetracyclin-sensitive transformants. The purified plasmid DNA was analysed with restriction enzymes. This resulted in plasmid pUR2302 encoding the complete guar pre-pro-alpha-galactosidase gene from which the non-translated sequences after the translation stop had been removed.

Construction of pUR2304

The plasmid pUR2303 was cut with SalI and the resulting single-stranded cohesive ends filled in (made double-stranded) by treatment with the Klenow fragment of DNA polymerase I and deoxynucleotide triphosphates. Synthetic BamHI linker sequences [5'CCGGATCCGG] were added by ligation with a molar excess of the previously phosphorylated linkers. The plasmid was then digested with BamHI, the 1:2 kb fragment purified after gel electrophoresis and ligated into the BamHI site of vector pUC9 (Vieira et al., 1982). The ligation mixture was used to transform E. coli JM101 (Yanisch-Perron et al., 1985), with selection for white ampicillin-resistant colonies. Plasmid DNA was prepared from transformed clones and subjected to restriction enzyme analysis. A correct plasmid was selected for further use and designated pUR2304. The latter plasmid was used as a source of the alpha-galactosidase coding sequence present on a 1.2 kb BamHI fragment.

Construction of the Plant Expression Vector pUR8001

The plant expression vector forms a component of a binary vector system pBin19 (Bevan, 1984) in Agrobacterium tumefaciens which is capable of transfer to plants, and comprises: a broad host range replicon which confers stable maintenance in E. coli or Agrobacterium: a kanamycin resistance gene which functions in bacteria: a region of DNA flanked by the 25 base pair repeats of the TDNA which contains: a kanamycin resistance gene which functions in plants and an expression cassette comprising the 355 RNA promoter of cauliflower mosaic virus and the transcription terminator of the nopaline synthetase gene, coupled via a BamHI cleavage site; a mobilisation site which enables this vector to be mobilised for conjugative transfer (in trans) by pRK2013.

In order to insert the alpha-galactosidase gene within the expression site, this vector was digested with BamHI, dephosphorlated and purified after gel electrophoresis.

The 1.2 kb alpha-galactosidase BamHI fragment was purified from pUR2304, mixed with the linearlised dephosphorylated vector and the two ligated together. The ligated mixture was used to transform E. coli JM101 (Yanicsh-Perron et al., 1985), positive clones being selected as kanamycin-resistant. Plasmid DNA was prepared form several clones and checked via restriction enzyme analysis for 1) the presence of the 1.2 kb alpha-galactosidase gene fragment, and 2) the correct orientation of this fragment, i.e. that the N terminal coding portion of the gene was adjacent to the promoter gene of the expression cassette. The latter feature was determined making use of the asymmetrically placed cleavage site for PstI. A plasmid with the correct orientation was chosen. (pUR8001; see FIG. 19; deposited in E. coli JM101 at the Centraalbureau voor Schimmelcultures, P.O. Box 273, N1-3740 AG Baarn, The Netherlands, under number CBS 337.87).

Introduction of Vector pUR8001 in Tobacco Cells

An E. coli clone containing pUR8001 was used in a tripartite mating with Agrobacterium tumefaciens strain LBA 4404 (Hoekema et al., 1983) and E. coli strain HB101 (Boyer et al., 1969) harbouring pRK2013 in order to transfer pur8001 to the Agrobacterium strain. Since the latter was resistant to Rifampicin ®, this antibiotic was used in conjunction with kanamycin as a counter selection against the donors int he mating.

Generation of Transformed Callus

A derivative of A. tumefaciens LBA 4404 carrying both its original Ti plasmid which functions in trans to mobilise TDNA into plants, and pUR8001 was thus isolated and used to transfer the alpha-galactosidase gene within its expression cassette into plant tissues using a derivative of the leaf disc method of Horsch et al. (1985). Leaf discs of 8 mm diameter were punched from newly expanded leaves of axenically (which means pure culture, without bacteria etc.) grown plants of Nicotiana tabacum SR 1 (seed may be obtained from R. Shields, Unilever Research Laboratory Colworth House, United Kingdom). The discs were transferred under aseptic conditions into an overnight culture of the above A. tumefaciens derivative ($10^9$ cells/ml) in Lennox Broth. They were incubated for 10 minutes, then removed, blotted dry and plated axial face down onto sterile filters on the surface of agar medium (shooting medium or callusing medium) seeded with 2 ml of a Nicotiana plumbaginafolia suspension culture. The inoculated leaf discs were thus cultured at 26° in the light for 2 days and then transferred to selective medium containing 100 /µg/ml kanamycin plus 500 /µg/ml cefotaxime (Claforan ®, supplied by Roussell). Callus cultures were retained and propagated on the appropriate medium with a 3 weekly passage interval and continuous selection with both kanamycin and cefotaxime.

Generation of Transformed Plants

In the case of cultures where shooting was promoted (shooting medium), as shoots appeared 2–4 weeks after infection with A. tumefaciens, the shoots were dissected from the leaf discs onto a medium which contained no phytohormones but which did contain cefotaxime. When roots appeared on the shoots, the shoots were again excised and transferred to medium containing cefotaxime and kanamycin but no phytohoromones. Those shoots which remained green and produced further roots under kanamycin selection were subsequently found to be transformed when further tested for the presence of markers present on the vector.

Control transformations using a vector (Bin 6) (freely available from Dr M. Bevan, Plant Breeding Institute, Maris Lane, Trumpington, Cambridge CB2 2LQ, United Kingdom), which did not contain alpha-galactosidase sequences, but which did confer on plants the ability to produce nopaline, were performed in parallel by the above procedure.

Generation of Liquid Suspension Cultures from Transformed Callus

A small segment of transformed callus (200 mg) growing on callusing medium (solid) containing kanamycin (100 /µg/ml) and cefotaxime (500 /µg/ml) was put into liquid callusing medium (50 ml) containing the above antibiotics, and cultured on an orbital shaker in the dark. As the culture thickened, it was sieved (under sterile conditions) to create an even suspension of cells. Suspension cultures were subcultured at 14 day intervals.

Generation of Hairy Root Cultures from Transformed Plants

Leaf discs were cut from the leaves of transformed plants growing on 100 /µg/ml kanamycin. Cut discs were incubated with an overnight culture of *Agrobacterium rhizogenes* R1000 (available from: Dr Conrad Lichtenstein, Imperial College London) for 10 minutes. The discs were removed from the bacterial culture and blotted dry and then plated face down onto feeder layers of *Nicotiana plumbaginafolia* (as described above for infection by *Agrobacterium tumefaciens*). After 2-3 days, the discs were plated axial face down onto hairy root culture medium (solid) containing kanamycin (100 /µg/ml) and cefotaxime (500 /µg/ml). After 10-15 days, roots appeared which were cut off and put into hairy root culture medium (liquid) containing 100 /µg/ml kanamycin, and cultured on an orbital shaker. Roots were subcultured approximately every 10 days.

Media

Callusing: Murashige and Skoog Basic Medium (Flow Laboratories)
3% sucrose
2 mg/liter naphthyl acetic acid (auxin)
0.5 mg/liter benzyl amino purine (cytokinin)
(Agar as necessary for solid media)
Shooting: Murashige and Skoog Basic Medium (Flow Laboratories)
+3% sucrose
+0.02 mg/liter indole acetic acid (auxin)
+1 mg/liter benzyl amino purine (cytokinin)
(Agar as necessary for solid media)
Hairy root culture medium: Murashige and Skoog Basic Medium (Flow Laboratories)
3% sucrose
0.1 mg/liter naphthyl acetic acid.

Testing of Transformed Plant Tissues for the Production of Alpha-Galactosidase a) Direct Chemical Assay Extracts were prepared from tobacco plants, e.g. callus, leaves or hairy roots, using 100-300 mg tissue homogenized in ice-cold extraction buffer (1 ml). Alternatively, the supernatant of a suspension culture was used. Forty microliters of extract or the supernatant was incubated with 2 ml assay buffer (4-methylumbellifery-alpha-D-galactoside from Sigma (1 mM) in extraction buffer) at 37° C. and 500 /µl aliquote withdrawn at 0, 5, 10 and 15 minute intervals and stopped by addition to 3 ml 0.2M Na2CO3. The fluorescence of liberated 4-methylumbelliferone was determined with excitation at 365 nm and emission at 455 nm using a Baird Nova 2 spectrofluorimeter, with slit widths set at 10 nm and calibrated with freshly prepared solutions of 4-methylumbelliferone.

Extraction buffer: Sodium acetate (50 mM, pH 5) EDTA disodium salt (1 mM) Dithiothreitol (10 mM) Triton X-100 (0.1%)

Figure 20:
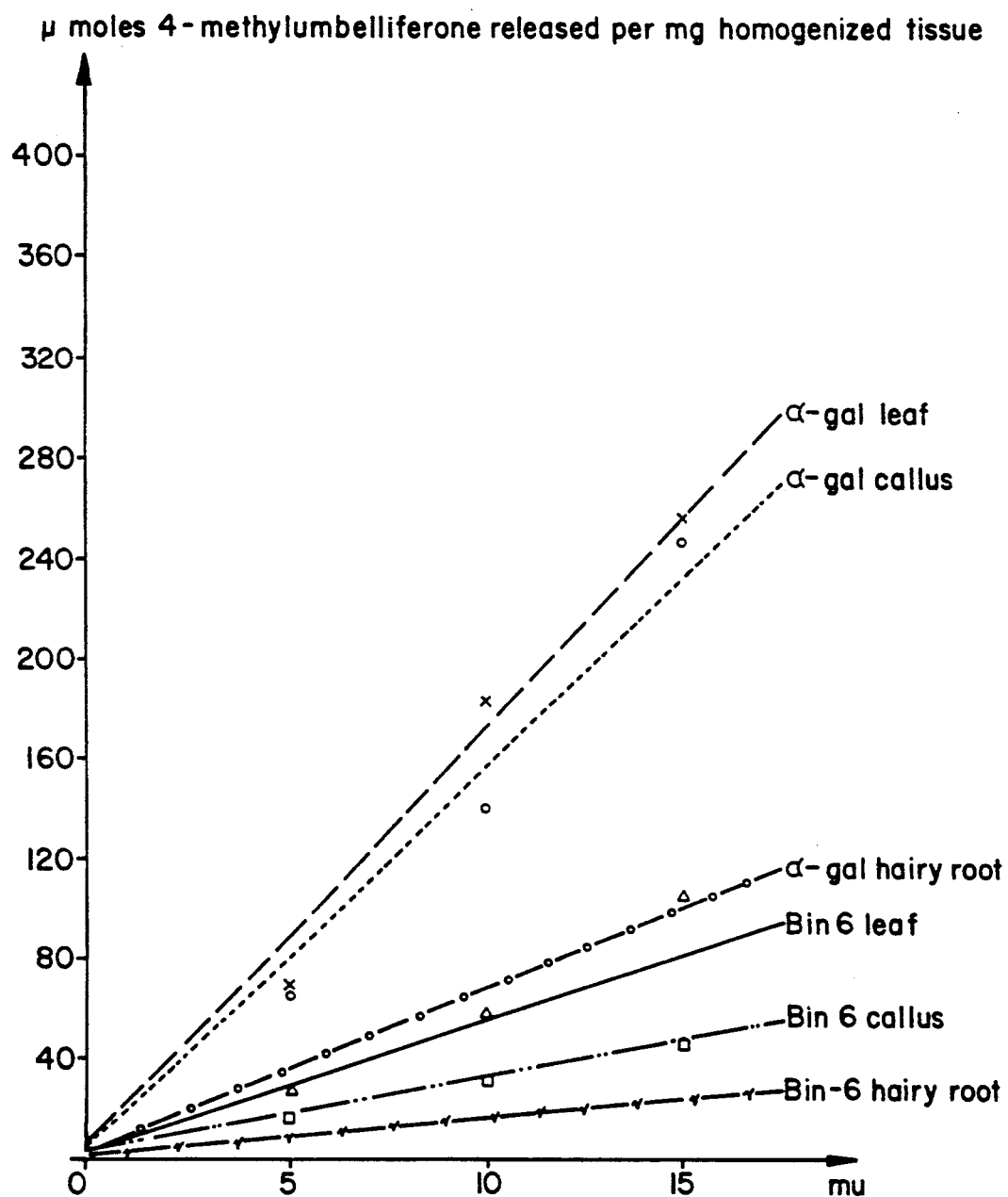

Values determined with this assay were plotted in FIG. 20. From this Figure it can be seen easily that the transformed call preparations gave a much higher alpha-galactosidase activity than the comparative preparations. The latter did not contain plasmids carrying the guar alpha-galactosidase gene.

b) IMMUNOLOGICAL DETECTION (i) Sample preparation

Small segments of transformed plant tissue (callus or leaf) (100 mg) were ground to powder in liquid nitrogen in 1.8 ml Ependorf tubes using a Teflon pestle with a conical tip. The powder was allowed to thaw in the presence of 200 µl of 2×standard concentration SDS gel sample buffer (Laemmli, 1970) with gentle homogenization. Samples of guar endosperm containing authentic salpha-galactosidase were prepared by controlled synchronous germination as described in Example 1. 24 hour-germinated endosperms (4 per extract) were gound in liquid nitrogen as described above and thawed into 200 µl 6×standard concentration sample buffer with gentle homogenization. The homogenate was diluted to 600 µl with distilled water. All extracts were boiled for 5 minutes and then centrifuged at 10,000 g for 5 minutes. The supernatants were loaded on a 10% SDS gel and electrophoresed at 300 V for 3 hours and than at 100 V for 2 hours (for loading, see corresponding figure legends). The gel was then subjected to an electroblotting procedure onto a nitrocellulose filter. The filter was then treated as follows:

1) incubation for 16 hours in TBS (0.5 M NaCl, 20 mM Tris.HCl, ph 7.5) plus 1% haemoglobin;
2) incubation for 3 hours in 25 ml of 1:100 dilution of affinity purified anti-alpha-galactosidase in TBS+1% haemoglobin+0.1% Tween 20 (first antibody);
3) washing in TBS+1% haemoglobin+0.1% Tween 20 (2×50 ml), then in 1 M NaCl, 20 mM Tris.HCl, ph 7.5, 0.1% Tween 20 (4×100 ml) over a period of 2 hours;
4) incubation with a 1:2000 dilution of goat-anti-rabbit horse-radish peroxidase conjugate in TBS, 0.1% Tween 20, 1% haemoglobin for 2 hours (second antibody);
5) washing in 1 M NaCl, 20 mM Tris.HCl, 0.1% Tween (4×100 ml) over a period of 1 hour;
6) final rinse in distilled water;
7) incubation with standard horse-radish peroxidase colour development reagent (as described by the supplier of the HRP kit - Biorad) for 2 minutes.

Figure 21:
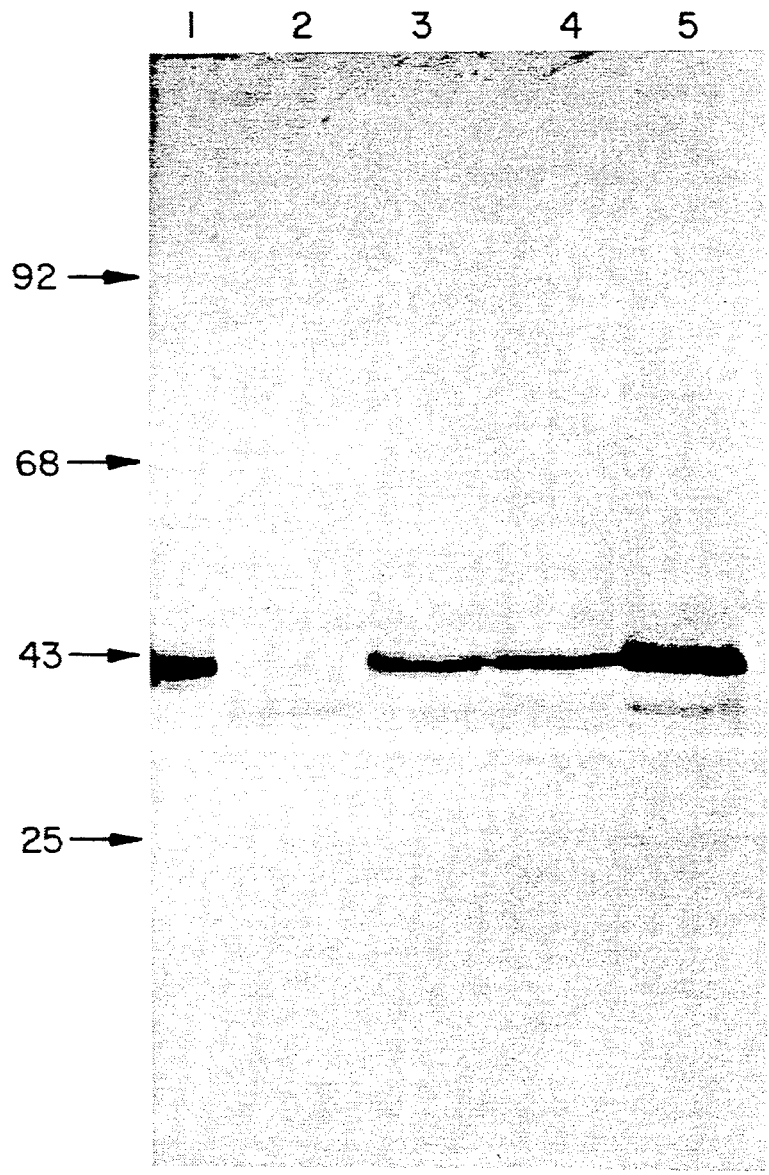

The above electro-immunoblotting procedure (Western Blotting) was successful in demonstrating that transformed calli C1, F11 and B1 contained protein material capable of cross-reacting with anti-alpha-galactosidase which is not present in callus transformed with the control plasmid Bin 6 (FIG. 21). Furthermore, the cross-reacting species is of the same mobility (molecular weight) as the authentic alpha-galactosidase seen in the extracts of germinating guar endosperms.

This suggests that the pre-pro form of alpha-galactosidase, as encoded by the transferred gene, is correctly processed to the mature form when expressed by tobacco callus and this supports our conclusion, based on our observation of alpha-galactosidase activity in culture supernatants of suspension cultures of C1, F11 and B1, that alpha-galactosidase can be secreted by transformed tobacco cells.

Electro-immunoblotting. studies of transformed tobacco leaves containing the alpha-galactosidase gene (transformed with pUR8001) have similarly shown expression of a form of alpha-galactosidase corresponding in size to the mature processed form of the enzyme.

TABLE I

| Origin enzyme | Immunological Relationship | | Modification |
|---|---|---|---|
| | Ouchterlony | Western | |
| guar | + | + | + |
| fenugreek | + | + | + |
| lucerne | + | + | + |
| carob | ND | + | ND |
| coffee beans | − | + | + |
| A. niger | − | − | − |
| S. carlsbergensis | − | − | − |
| E. coli | − | − | − |
| rDNA S. cerevisiae | + | + | + |
| rDNA B. subtilis | ND | + | + |
| rDNA K. lactis | ND | + | ND |
| rDNA H. polymorpha | ND | + | ND |

Legend Table 1 alpha-Galactosidase enzymes from 12 sources were assayed for immunological relationship by the Ouchterlony technique and the Western blot technique as well as for the capacity to decrease the galactose content of galactomannans.

For the Ouchterlony assay, enzyme preparations with a concentration of about 10 U/ml were used. For the Western blot technique 5 $\mu$l of solutions of 0.1 U/ml to 0.5 U/ml were used.

ND: not determined.

References

Backman, K., Ptashne, M. and Gilbert, W. (1976), Proc. Natl. Acad. Sci. U.S.A. 73: 4174–4178.
Bahl, O. P. and Agrawal, K. M. L. (1969), J. Biol. Chem. 244: 2970–2978.
Beggs, J. D. (1978), Nature 275: 104–109.
Bevans, M. (1984), Nucleic Acids Res. 12: 8711–8721.
Biggin, M. D., Gibson, T. J. and Hong, G. F. (1983), Proc. Natl. Acad. Sci. U.S.A. 80: 3963–3965.
Birnboim, H. C. and Doly, J. (1979), Nucleic Acids Res. 7: 1513–1523.
Bishop, D. F., Calnoun, D. H., Bernstein, H. S., Hantzopoulos, P., Quinn, M. and Desnick, R. J. (1986), Proc. Natl. Acad. Sci. U.S.A. 83: 4859–4863.
boyer, H. W. and Roulland-Dussoix, D. (1969), J. Mol. Biol. 41: 459–472.
Broach, J., Strathern, J. and Hicks, J. (1979), Gene 8: 121–133.
Buckholz, R. G. and Adams, B. G. (1981), Mol. Gen. Genet. 182: 77–81.
Burnette, W. N. (1979), Anal. Biochem. 112: 195–203.
Chen, E. J. and Seeburg, P. H. (1985), DNA 4: 165–170.
Dente, L., Cesareni, G. and Cortese, R. (1983), Nucleic Acids Res.11: 1645–1655.
Edens, L., Heslinga, L., Klok, R., Ledeboer, A. M., Maat, J., Toonen, M. Y., Visser, C. and Verrips, C. T. (1982), Gene18: 1–12.
Edens, L., Ledeboer, A. M., Verrips, C. T. and van den Berg, J. A. (1983), EP-A- 0 096 910.
Edens, L., Russell, S. W., Visser, C. and Verrips, C. T. (1984), EP-A- 0 129 268.
Edman, P. and Begg, G. (1967), Eur. J. Biochem 1: 80–91.
Gleeson, M. A., Ortori, G. S. and Sudbery, P. E. (1986), J. Gen. Microbiol. 132: 3459–3465.
Grandi, G., Del Bue, M., Palla, E., Mele, A., Coletti, E. and Toma, S. (1986), Plasmid 16: 1–14.
Gubler, U. and Hoffman, B. J. (1983), Gene 25: 263–269.
Hinnen, A., Hicks, J. B. and Fink, G. R. (1978), Proc. Natl. Acad. Sci. U.S.A. 75: 1929–1933.
Hoekema, A., Hirsch, P. R., Hooykaas, P. J. J. and Schilperoort, R. A. (1983), Nature 303: 179–180.
Hopper, J. E. and Rowe, L. B. (1978), J. Biol. Chem. 253: 7566–7569.
Horech, R. B. and Fry, J. E., Hoffmann, N. L., Eichholtz, D., Rogers, S. C. and Fraley, R. T. (1985), Science 227: 1229–1231.
Ito, H. Fukuda, Y., Murata, K. and Kimura, A. (1983), J. Bacteriol. 153: 163–168.
Kawamura, F. and Doi, R. H. (1984), J. Bacteriol. 160: 442–444.
Kok, J., Maat, J., van der Vossen, J. P. B. M. and Venema, G. (1985), EP-A- 0 157 441.
Laemmli, U. K. (1970), Nature 227: 680–685.
Ledeboer, A. M., Maat, J., Verrips, C. T., Visser, C., Janowicz, Z. A. and Hollenberg, C. P. (1984), EP-A- 0 173 378.
Ledeboer, A. M., Edens, L., Maat, J., Visser, C., Bos, J. W., Verrips, C. T., Janowicz, Z., Eckart, M., Roggenkamp, R. and Hollenberg, C. P. (1985), Nucleic Acids Res. 13: 3063–3082.
Lehrach, H., Diamond, D., Wozney, J. M. and Boedtker, H. (1977), Biochemistry 16: 4743–4751.
Liljeström, P. L. (1985), Nucleic Acids Res. 13: 7257–7268.
Liljeström, P. L. and Liljeström, P. (1987), Nucleic Acids Res. 15: 2213–2221.
Loewus, F. A. (1952), Anal. Chem. 24: 219.
Maniatis,T., Fritsch, E. F. and Sambrook, J. (1982), Molecular Cloning, A laboratory manual, Cold Spring Harbor Laboratory.
Matteucci, M. D. and Caruthers, M. H. (1981), J. Am. Chem. Soc. 103: 3185–3191.
McCleary, B. V. (1983), Phytochemistry 22: 649–658.
McCleary, B. V., Critchley, P. and Bulpin, P. V. (1984), EP-A- 0 121 960.
Meier, H. and Reid, J. S. G. (1982), in "Encyclopedia of Plant Physiology", New Series 13A, Loewus, F. A. and Tanner, W. (editors), pp. 418–471.
Messing, J., Crea, R. and Seburg, P. H. (1981), Nucleic Acids Res. 9: 309–321.
Morris, D. L. (1948), Science 107: 254–255.
Nogi, Y. and Fukasawa, T. (1983), Nucleic Acids Res. 11: 8555–8568.
Norrander, J., Hempe, T. and Messing, J. (1983), Gene 26: 101–106.
Proudfoot, N. J. and Brownlee, G. G. (1976), Nature 263: 211–214.
Seiler, A. (1977), Planta 134: 209–221.
Summer-Smith, M., Bozzato, R. P., Skipper, N., Davies, R. W. and Hopper, J. E. (1985), Gene 36: 333–340.
Tajima, M., Nogi, Y. and Fukasawa, T. (1985), Yeast 1: 67–77.
Taussig, R. and Carlson, M. (1983), Nucleic Acids Res. 11: 1943–1954.
Tuite, M. F., Dobson, M. J., Roberts, N. A., King, R. M., Burke, D. C., Kingsman, S. M. and Kingsman, A. J. (1982), EMBO j. 1: 603–608.
Vieira, J. and Messing, J. (1982), Gene 19: 259–268.
Wyckoff, M., Rodbard, D. and Chrambach, A. (1977), Anal. Biochem. 78: 459–482.
Yanisch-Perron. C., Vieira, J. and Messing. J. (1985), Gene 33: 103–119.

Yarger, J. G., Gorman, M. C. and Polazzi, J. (1985), Dev. Ind. Microbiol. 26: 181–192.

LIST OF ABBREVIATIONS USED

EP-A-: European Patent Application laid open to public inspection about 18 months after the first claimed priority date or its filing date if no priority was claimed
pNPG: p-nitrophenyl-alpha-D-galactopyranoside
ATP: adenosine triphosphate
dCTP: deoxycytosine triphosphate
TTP: deoxythymine triphosphate
GAPDH: glyceraldehyde-3-phosphate dehydrogenase
$OD_{260}$: optical density at 260 nm
SDS: sodium dodecyl sulphate
HAc: acetic acid
NaAc: sodium acetate
E buffer: 40 mM Tris-HAc pH 7.6, 20 mM NaAc, 20 mM EDTA
O buffer: 10 mM Tris-Hcl pH 7.5, 1 mM EDTA, 0.5 M NaCl, 0.1 Sarkosyl
STE buffer: 100 mM NaCl, 10 mM Tris-HCl pH 7.5, 1 mM EDTA
MOPS: 3-(N-morpholino)propanesulphonic acid
MOPS buffer: 0.02 M MOPS pH 7.0, 1 mM EDTA
SSC: 150 mM NaCl, 15 mM Na-citrate
YMM: yeast minimal medium containing 0.67% yeast nitrogen base without amino acids and 2.0% glucose
YPD medium: 2% glucose; 2% Bacto-peptone, Difco; 1% yeast extract, Difco
YPG medium: 2% glactose; 2% Bacto-peptone, Difco; 1% yeast extract, Difco
FDA staining: fluorescein diacetate staining Other abbreviations and the meanings of various expressions are given in Oliver, S. G. and Ward, J. M., A dictionary of genetic engineering, Cambridge University Press, 1985.

pURY2703, pURY2705, pURY2705' and pURY2706 are synonyms for pUR2703, pUR2705, pUR2705' and pUR2706, respectively.

LEGENDS TO THE FIGURES

FIG. 1

Cross-section of guar seed
A = seed coat
B = aleurone cells
C = endosperm
D = cotyledon
E = "thin" endosperm layer

FIG. 2

Analysis of in vitro translation products with RNA purified from the aleurone cells of guar seed as a template Poly-A RNA preparations from yeast (2 /µg; lane A) and poly-A RNA from guar (5 /µg; lane B, C) served as the template for translation. The translation products were applied to the gel directly (lane A, B) or after incubation with alpha-galactosidase specific antibodies (lane C). $^{14}$C-labelled proteins (Amersham) served as molecular weight standards (lane D). The exposure for lane C was 5 times longer than for the other samples, which were exposed overnight at −70° C.

FIG. 3

Amino acid sequence of peptides and the nucleotide sequence of the probes derived thereof The internal peptide (A) and the $NH_2$-terminal sequence (B) are presented in the one letter notation of amino acids. The nucleotide sequences of the mixed probes are shown directly below the amino acid sequences from which they have been derived. Notations for the mixed positions are: U=A or G; V=T or C; X=A, G, T or C; Y=T or G. MP33 a 21-mer with 128 permutations, MP42 a 14-mer with 16 permutations, MP43 a 14-mer with 8 permutations and MP44 a 41-mer with 128 permutations.

FIG. 4

Northern blot hybridization of guar mRNA with oligonucleotide probe MP33
Lane A: 5 /µg poly-A RNA from aleurone cells of guar seed.
Lane B: 5/µg total RNA from aleurone cells of guar seed.
The most stringent wash was performed in 5×SSC 0.1% SDS at 35° C.
E. coli ribosomal RNA was the molecular weight standard.

FIG. 5

Restriction map, subclones and sequencing strategy of plasmid pUR2302
A. Preliminary restriction map of plasmid pUR2302.
B. The fragments from pUR2302 and pUR2314 as subcloned in the M13 vectors M13mp18 and M13mp19.
C. Sequencing strategy used for establishment of the sequence of pUR2302 and pUR2314. Arrows indicate the direction of sequencing. The boxes indicate the priming site for the sequencing reaction with the different oligonucleotides (U: universal M13 primer; numbers: oligonucleotide primers synthesized for the sequencing experiments). The lower line represents the super-coiled sequencing experiment.
P=PstI, K=KpnI, X=XmnI.

FIG. 6

Complete nucleotide sequence of the guar alpha-galactosidase cDNA clone pUR2302
The nucleotide sequence of the 5'-3' strand is shown. The poly dG/dC tail synthesized in the cDNA cloning procedure is shown on the 5' site (cf. nucleotides 6-20), whereas at the 3' site the dG/dC tail follows after the poly-A tail (not shown). Polyadenylation consensus sequences (Proudfoot and Brownlee, 1976) are marked with a line above the nucleotides. The amino acid sequence derived from the nucleotide sequence is shown in the one letter notation above the nucleotide sequence. The numbering of the amino acids starts at +1 for the mature protein. The amino acids in the pre-pro sequence are negatively numbered.

FIG. 7

Strategy for the construction of plasmids pURY2703 and pURY2705
A detailes description of the several fragments is given in Example 2.
Symbols used:

GAPDH promoter

-continued

——— pre-prothaumatin gene
alpha-galactosidase gene
leu-2 gene
suc 2 (invertase) signal sequence ▭ 2 μm yeast vector
——— pBR322 E. coli vector

FIG. 8

The individual single stranded oligonucleotide fragments which have been synthesized are indicated by numbers between the arrows. Identical numbers in A (GAPDH promoter—mature alpha-galactosidase) and B (GAPDH promoter-invertase signal sequence—mature alpha-galactosidase) correspond to identical single stranded oligonucleotides used.

Restriction enzyme cleavage sites are indicated above the complete double stranded fragment. The start of translation and the first residue of the mature alpha-galactosidase are indicated below the double-stranded sequence by Met and Ala [1] respectively.

FIG. 9

Restriction map of plasmid pURY2703

The BglII site in the GAPDH promoter containing fragment is the arbitrary startpoint for nucleotide numbering which is indicated in kilobasepairs between brackets. With the exception of SalI and EcoRI, the restriction sites have been verified by digests and double digests.

Figure 7:
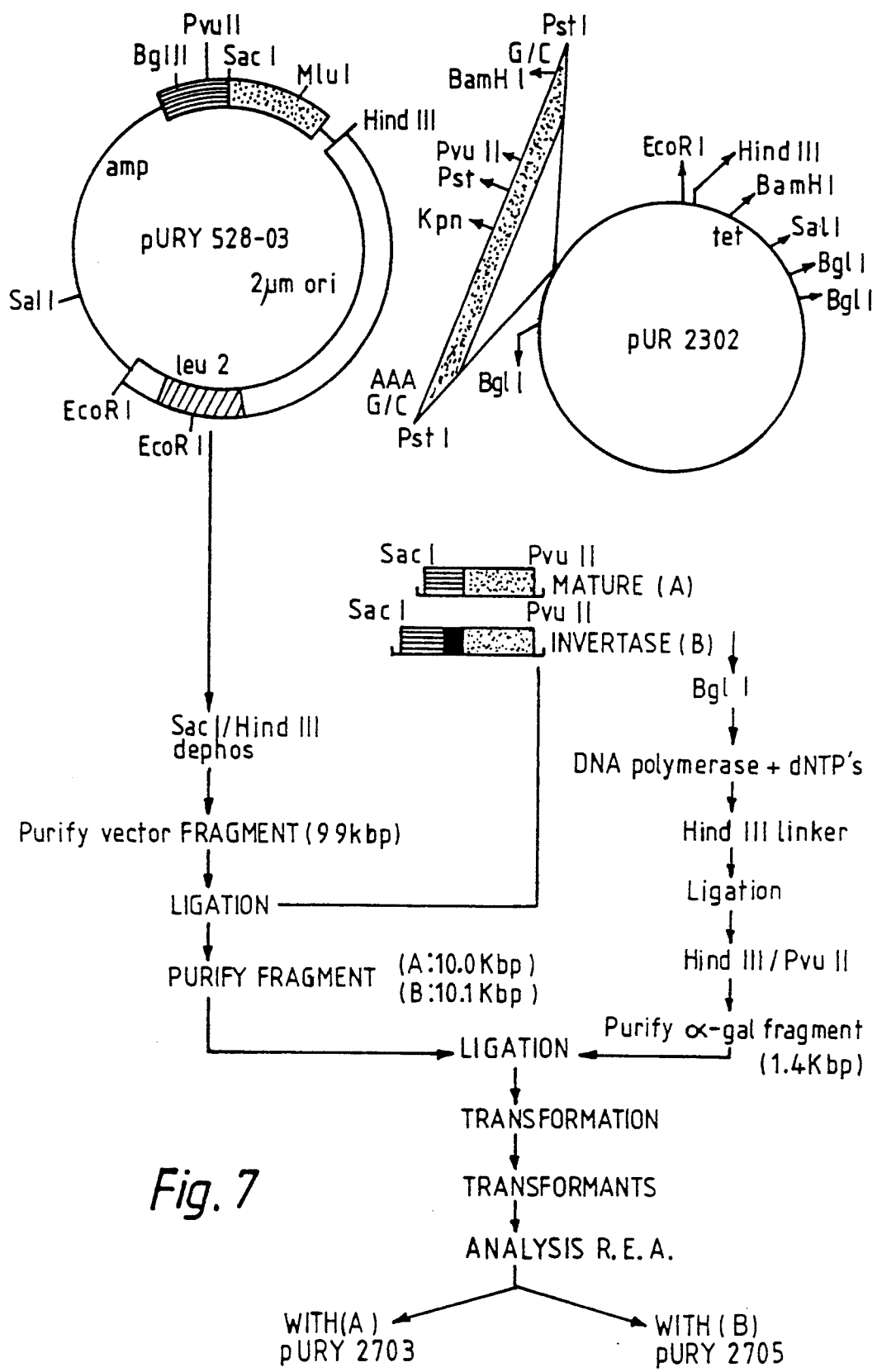
Figure 8:
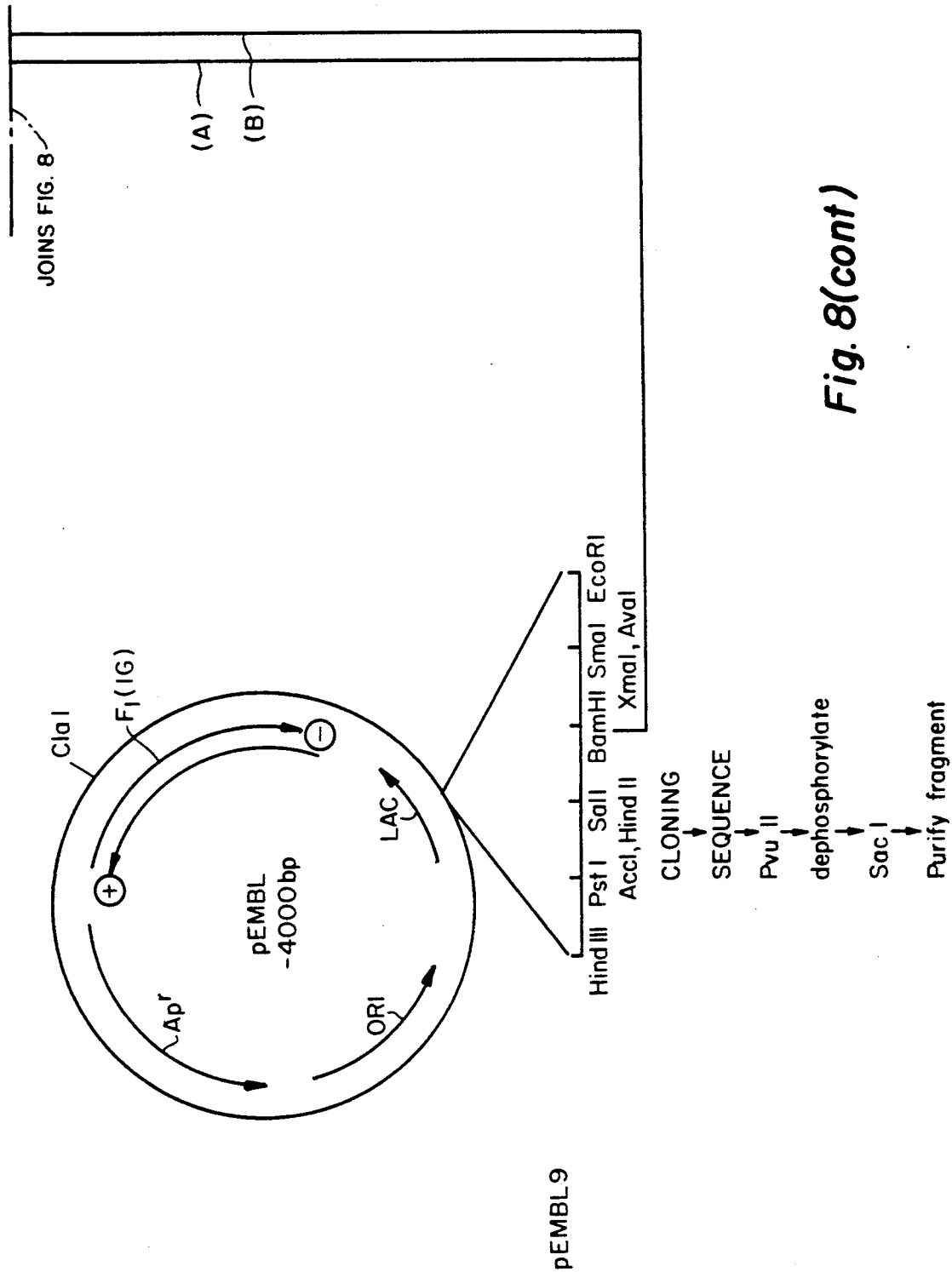

Symbols: see legend for FIG. 7; in addition, AAA/TTT, GGG/CCC stand for dA/dT and dG/dC tails, respectively.

FIG. 10

Restriction map of plasmid pURY2705

The BglII site in the GAPDH promoter is the arbitrary startpoint for nucleotide numbering which is indicated in kilobasepairs between brackets. With the exception of SalI and EcoRI, the restriction sites have been verified by digests and double digests.

Figure 9:
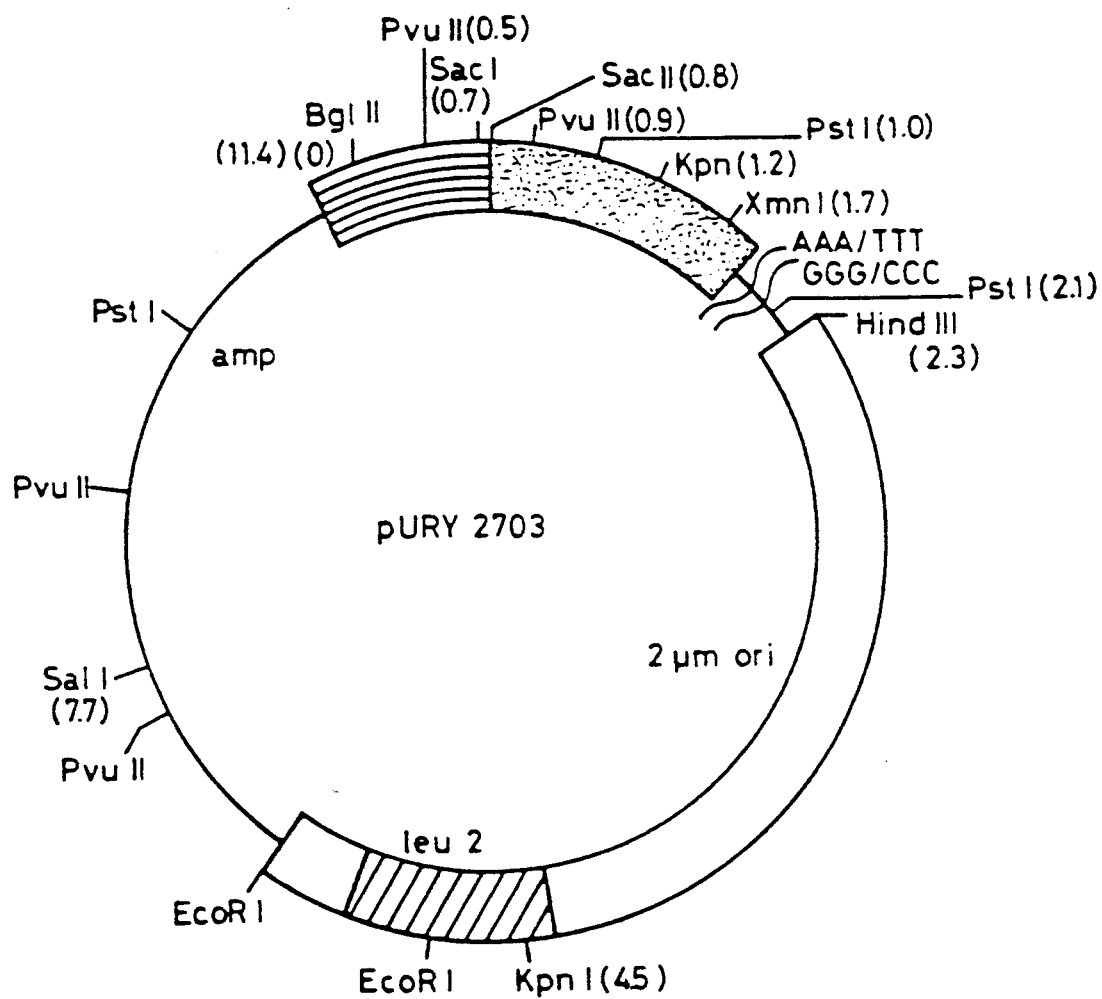
Figure 10:
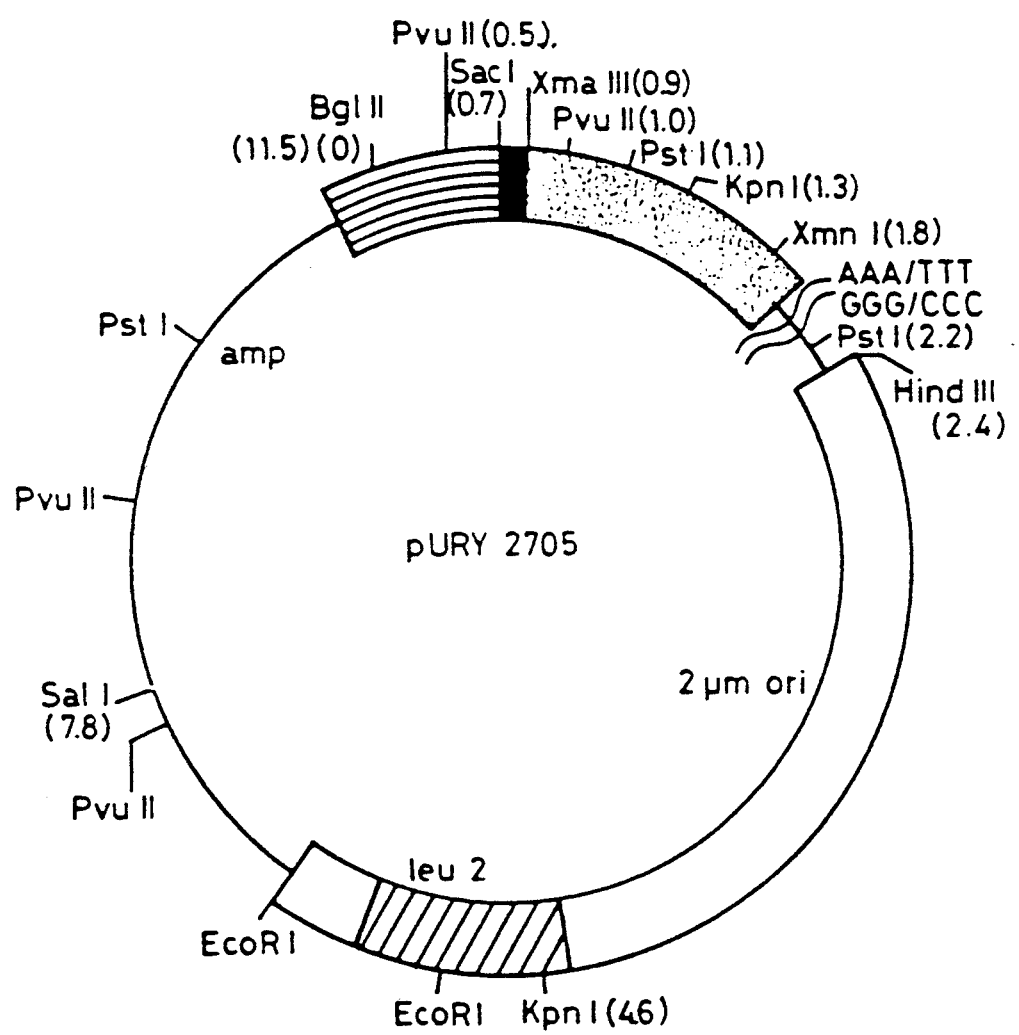
Figure 11:
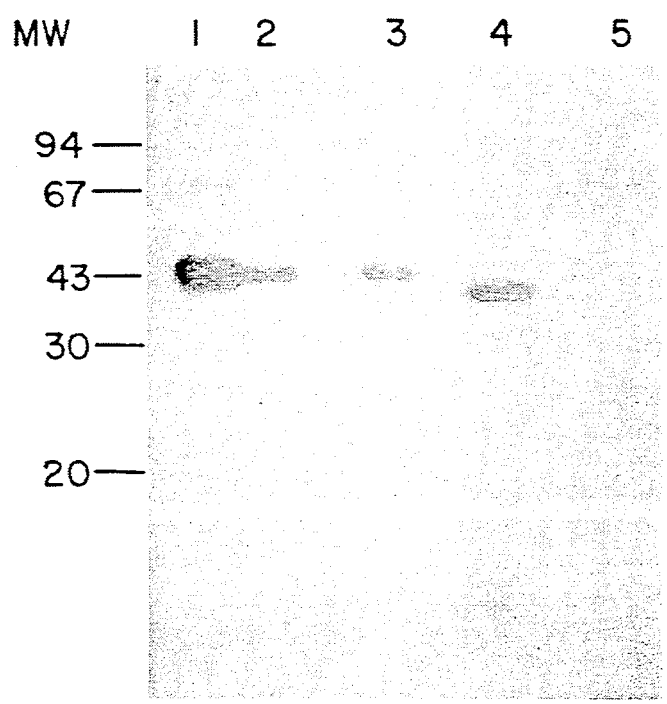

Symbols: see legend for FIG. 9.

FIG. 11

Western blot analysis of S. cerevisiae with pURY2703 and pURY2705

A detailed description of the procedure is given in Example 2.
lane 1: alpha-galactosidase purified from guar 4 ng
lane 2: as lane 1 1ng
lane 3: crude extract of cells with pURY2705
lane 4: crude extract of cells with pURY2703
lane 5: crude extract of cells without the plasmids.

FIG. 12

Strategy for the construction of plasmid pUR2405

A detailed description is given in Example 5. For symbols used see legend for FIG. 7. An open box also means the trp-1 gene where so indicated in the schematic representation of the plasmids, in addition to the meaning of the 2 /μm origin of the yeast vector (as indicated). A black box also means the KARS2 sequence where so indicated, instead of the suc 2 (invertase) signal sequence.

FIG. 13

Strategy for the construction of plasmid pUR2601

A detailed description is given in Example 6. The symbols used for pMS48 and the part thereof present in pUR2601 are given in FIG. 13. For symbols used for pURY2703 and the part thereof present in pUR2601, see the legend for FIG. 7.

FIG. 14

Production of alpha-galactosidase by B. subtilis with pUR2405 grown in shake flasks The develpment of biomass indicated by the optical density at 600 nm (OD600) and the formation of alpha-galactosidase in U/ml growth medium as determined by the pNPG assay are given in FIG. 14. The plotted values were determined after 3, 5, 7 and 24 hours of growth. After 24 hours the OD600 reached a maximum of 8 units on a Zeiss photospectrometer. On the contrary, for the alpha-galactosidase content a maximum value of about 0.1 U/ml growth medium was found after 7 hours of growth, whereas after 24 hours of growth the content was decreased to only 0.003 U/ml growth medium.

FIG. 15

Western blot analysis of B. subtilis with pUR2405

A detailed description of the procedure is given in Example 6.
lane 1: alpha-galactosidase purified from guar
lane 2: crude extract of cells with pUR2405
lane 3: as 2
land 4: growth medium of cells with pUR2405
lane 5: as 4

FIG. 16 (16-1 to 16-4)

Strategy for the construction of plasmid pUR3510

A detailed description of the various steps is given in Example 8. Unless otherwise indicated, the symbols used are the same as those shown in FIG. 7.

FIG. 17

Western blot analysis of H. polymorpha with pUR3510

A detailed description of the procedure is given in Example 8.
lane A: H. polymorpha L1 cell extract.
lane B: Purified guar alpha-galactosidase enzyme (10 ng).
lane C: H. polymorpha L1 with plasmid pUR3510.

Figures 1, 18:
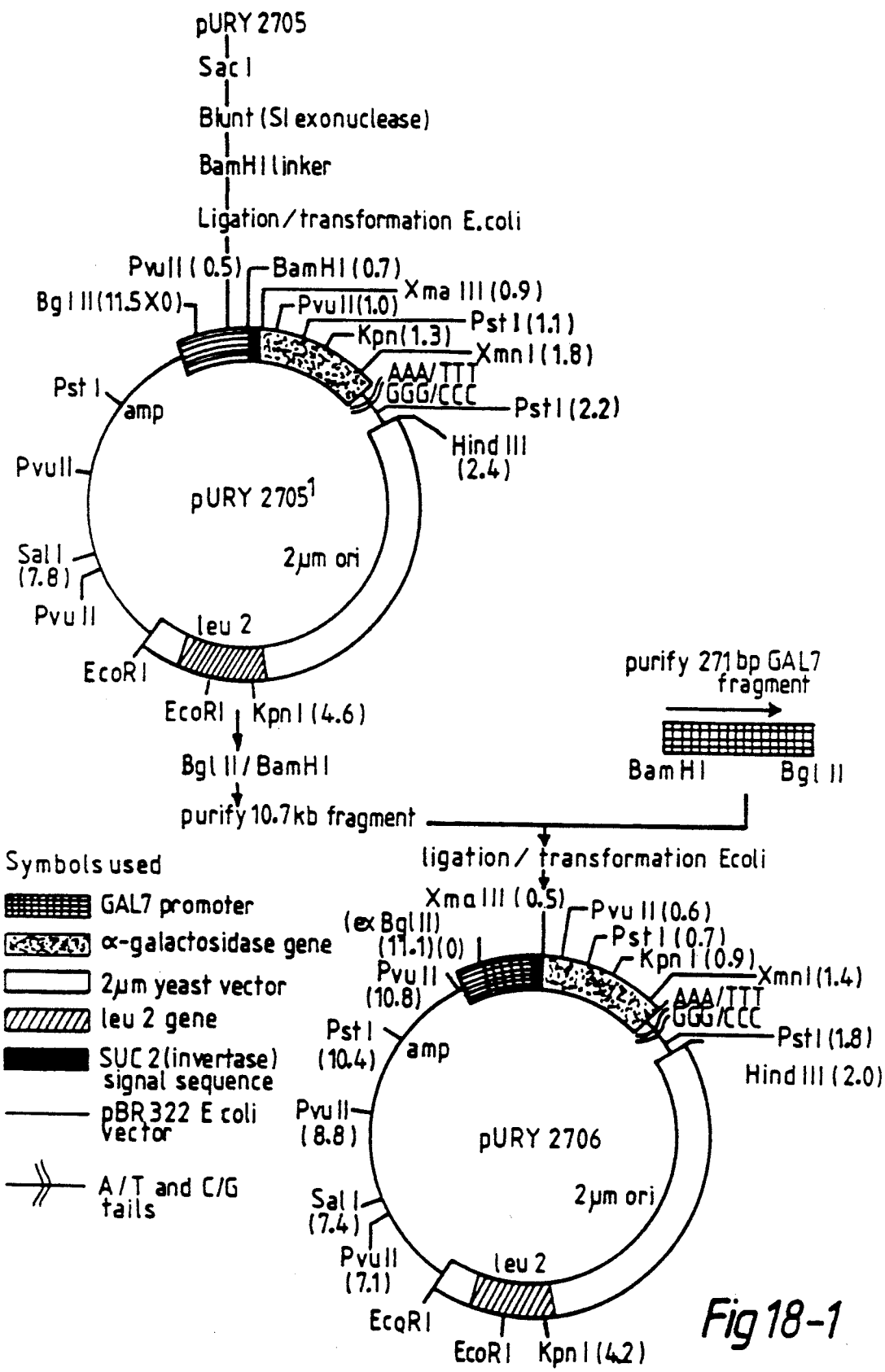
Figures 2C, 18:
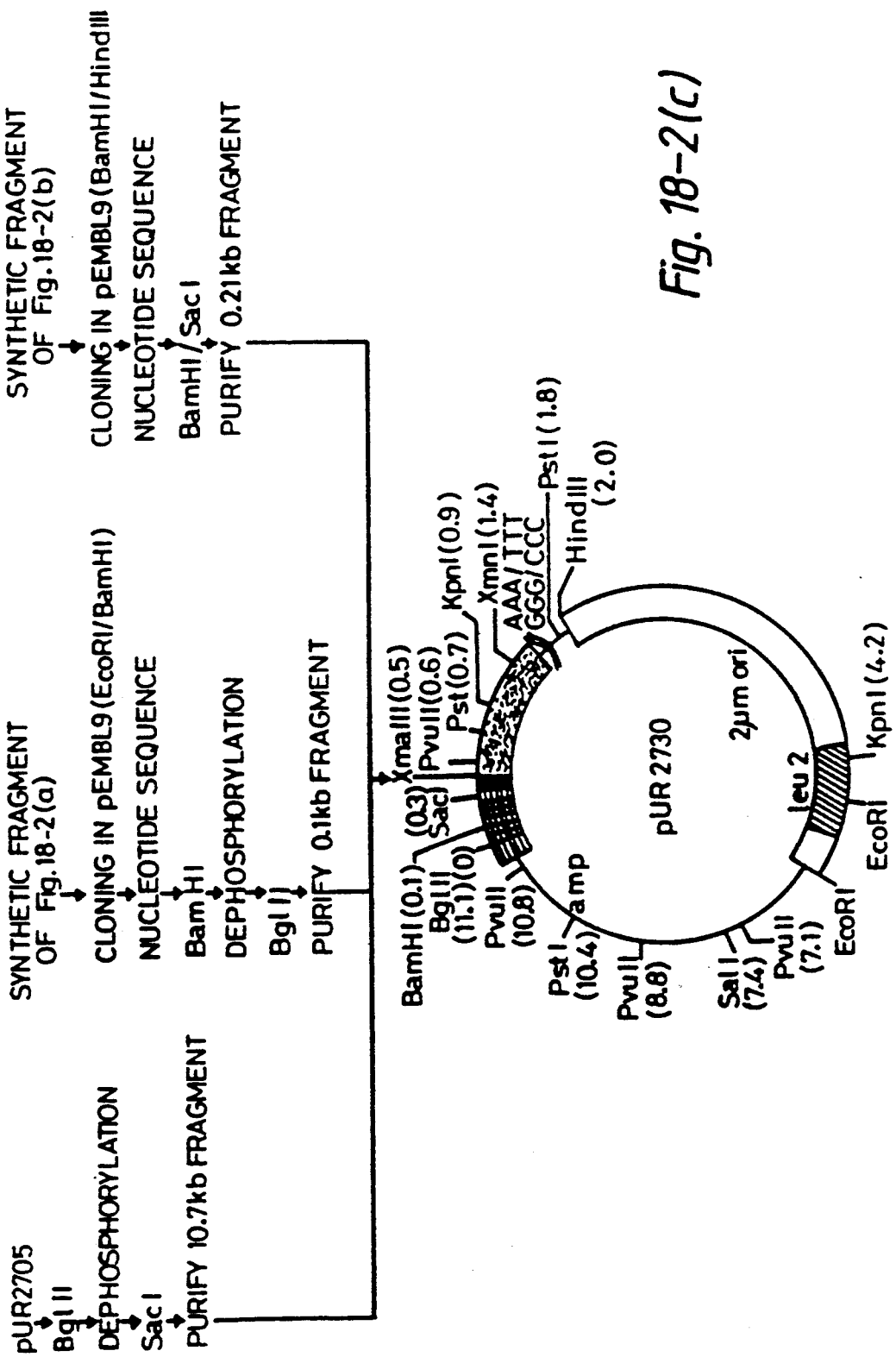
Figure 19:
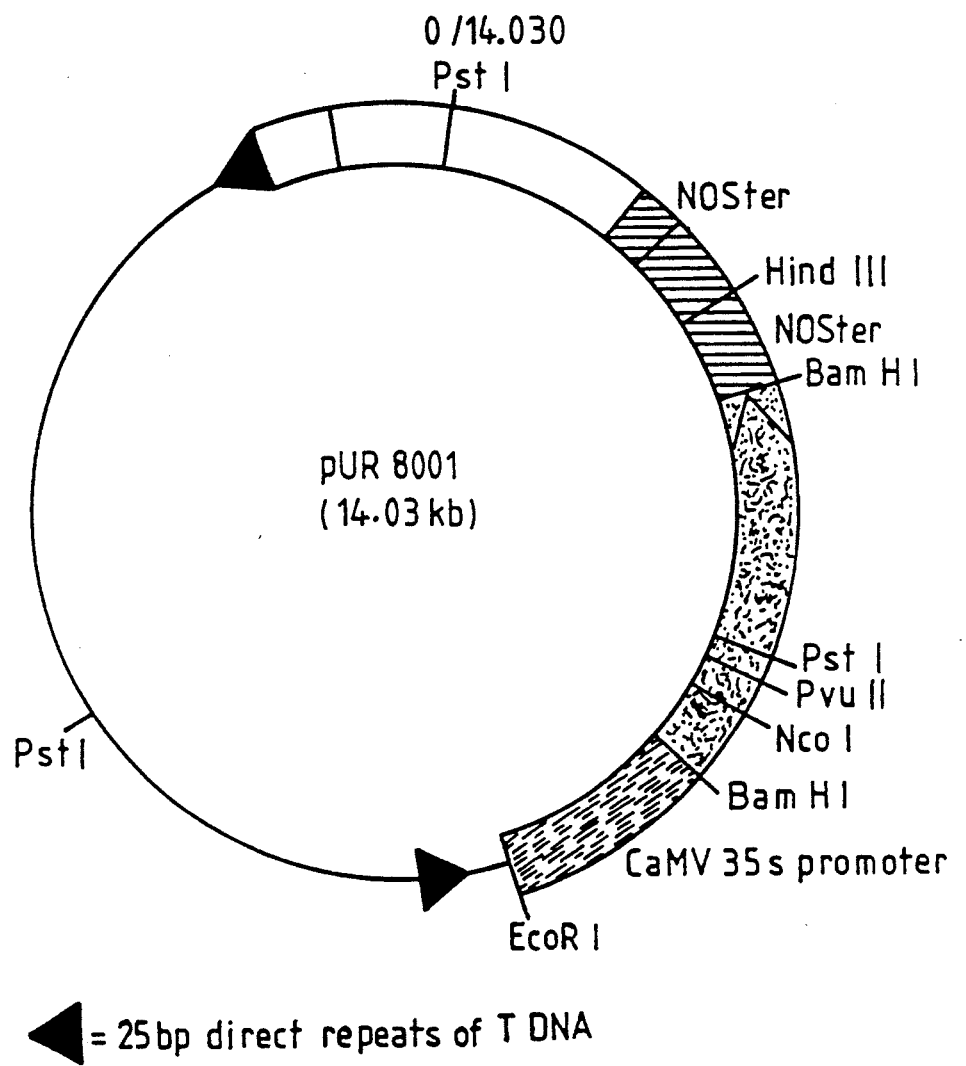

FIG. 18 (18-1 to 18-2)

Strategy for the production of plasmids pUR2706 and pUR2730

A detailed description is given in Example 9.

FIG. 19

Plant expression vector pUR8001

A detailed description of the various steps is given in Example 11. Unless otherwise indicated, the symbols used are the same as those shown in FIG. 7.

FIG. 20

Enzyme assays on tobacco plants and tissues transformed with pUR8001

Extracts of the various plant cell preparations were analysed for the presence of alpha-galactosidase using the artificial substrate of 4-methylumbelliferyl-alpha-D-galactopyranoside.

Next to preparations from cells transformed with the alpha-galactosidase-encodeing plasmid pUR8001, cells with the vector B in 6 were used as the control. For details, see Example 11.

FIG. 21

Western blot analysis of Nicotiana with pUR8001

A detailed description of the procedure is given in Example 11.
lane 1: extract germinating guar endosperm
lane 2: extract callus with Bin 6 (control)
lane 3: extract callus with pUR8001 (C1)
lane 4: extract callus with pUR8001 (F11)
lane 5: extract callus with pUR8001 (B1).

The arrows indicate the position of the molecular weight markers. From top to bottom: 92 Kd, 68 Kd, 43 Kd and 25 Kd.

We claim:

1. An expression system comprising:
   (i) a vector, and
   (ii) a nucleotide sequence encoding a mature protein both having α-galactosidase activity and being capable of decreasing the galactose content of galactomannans by splitting off 1-6 linked α-D-galactopyranosyl units attached to a main chain of 1-4 linked β-D-mannopyranosyl units, or a precursor of such a protein, wherein said precursor is a pre- form of the protein, a prepro- form of the protein, or a fusion form of the protein which upon cleavage results in the mature protein,
   wherein the nucleotide sequence is insufficiently complementary to the complement of the sequence of FIG. 6 to hybridize thereto, yet still encodes a protein comprising the following amino acid sequence:

AENGLGQTPPMGWNSWNHFGCDINE

NVVRETADAMVSTGLAALGYQYINL

DDCWAELNRDSEGNMVPNAAAFPSG

IKALADYVHSKGLKLGVYSDAGNQT

CSKRMPGSLGHEEQDAKTFASWGVD

YLKYDNCENLGISVKERYPPMGKAL

LSSGRPIFFSMCEWGWEDPQIWAKS

IGNSWRTTGDIEDNWNSMTSIADSN

DKWASYAGPGGWNDPDMLEVGNGGM

TTEEYRSHFSIWALAKAPLLVGCDI

RAMDDTTHELISNAEVIAVNQDKLG

VQGKKVKSTNDLEVWAGPLSDNKVA

VILWNRSSSRATVTASWSDIGLQQG

-continued
TTVDARDLWEHSTQSLVSGEISAEI

DSHACKMYVLTPRS, wherein said nucleotide sequence is operably linked to a regulatory sequence present in said vector, which regulatory sequence facilitates expression of said nucleotide sequence.

2. The expression system according to claim 1 further comprising:
   a translation stop codon operably linked at the 3' end of said nucleotide sequence, optionally followed by a transcription termination sequence; and
   a nucleotide sequence that facilitates integration of said nucleotide sequence into the genome of a host cell or an origin or replication.

3. The expression system according to claim 1 wherein said nucleotide sequence encodes said precursor form of said protein.

4. The expression system according to claim 1 wherein said nucleotide sequence encodes said mature form of said protein and a translation initiation ATG-triplet is operably linked at the 5' end of said nucleotide sequence.

5. The expression system according to claim 1 further comprising a marker that confers a selectable trait.

6. A transformed host cell comprising said expression system according to claim 1.

7. The transformed cell according to claim 6 wherein said cell is a plant cell.

8. The transformed cell according to claim 6 wherein said cell is a microorganism.

9. The transformed cell according to claim 8 wherein said microorganism is selected from the group consisting of bacteria, mould and yeast.

10. The transformed cell according to claim 6 wherein said cell is of a genus selected from the group consisting of Saccharomyces, Kluyveromyces, Bacillus, Hansenula, Pichia, Aspergillus, Solanaces and Nicotiana.

11. The transformed cell according to claim 6 wherein said cell is selected from the group consisting of *Saccharomyces cerevisiae, Saccharamyces carlsbergensis, Kluyveramyces marxianus* var. *lactis, Bacillus subtilis, Hansenula polymorpha, Pichia pastoris* and *Nictiana tabacum*.

12. A process for producing a protein both having α-galactosidase activity and being capable of decreasing the galactose content of galactomannans by splitting off 1-6 linked alpha-D-galactopyranosyl units attached to a main chain of 1-4 linked beta-D-mannopyranosyl units comprising culturing said transformed cell according to claim 6 under conditions such that said protein is produced, and recovering said protein.

13. The process according to claim 12 wherein said nucleotide sequence encodes said precursor of said mature protein and said precursor protein includes a signal sequence so that said mature protein is secreted by said transformed cells.

* * * * *